US011453882B2

(12) United States Patent
Nicholson et al.

(10) Patent No.: US 11,453,882 B2
(45) Date of Patent: Sep. 27, 2022

(54) HETEROLOGOUS BIOSYNTHESIS OF NODULISPORIC ACID

(71) Applicant: VICTORIA LINK LIMITED, Wellington (NZ)

(72) Inventors: Matthew Joseph Nicholson, Canterbury (NZ); Sarah Adeline Kessans, Christchurch (NZ); Emily Jane Parker, Wellington (NZ); Leyla Yolanda Bustamante Rodriguez, Prebbleton (NZ); David Barry Scott, Palmerston North (NZ); Kyle Cornelius Van de Bittner, Wellington (NZ); Craig John Van Dolleweerd, Prebbleton (NZ)

(73) Assignee: Victoria Link Limited

( * ) Notice: Subject to any disclaimer, the term of this patent is extended or adjusted under 35 U.S.C. 154(b) by 0 days.

(21) Appl. No.: 16/651,065

(22) PCT Filed: Sep. 28, 2018

(86) PCT No.: PCT/IB2018/057528
§ 371 (c)(1),
(2) Date: Mar. 26, 2020

(87) PCT Pub. No.: WO2019/064243
PCT Pub. Date: Apr. 4, 2019

(65) Prior Publication Data
US 2020/0299700 A1    Sep. 24, 2020

(30) Foreign Application Priority Data

Sep. 29, 2017  (AU) ................................ 2017903956

(51) Int. Cl.
*C12N 15/52* (2006.01)
*C12N 15/80* (2006.01)
*C12P 17/18* (2006.01)
*A01N 63/30* (2020.01)
*A01N 63/50* (2020.01)

(52) U.S. Cl.
CPC ............. *C12N 15/52* (2013.01); *A01N 63/30* (2020.01); *A01N 63/50* (2020.01); *C12N 15/80* (2013.01); *C12P 17/18* (2013.01)

(58) Field of Classification Search
CPC ......... C12N 15/52; C12N 15/80; C12P 17/18; C12P 17/188; C12P 17/182; A01N 63/50; A01N 63/30
See application file for complete search history.

(56) References Cited

U.S. PATENT DOCUMENTS

2007/0218461 A1    9/2007  Bryan et al.

OTHER PUBLICATIONS

Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Van de Bittner et al., Heterologous biosynthesis of Nodulisporic acid F. JACS., 2018, vol. 140: 582-585. (Year: 2018).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Guo et al., Protein tolerance to random amino acid change. PNAS., 2004, vol. 101 (25): 9205-9210. (Year: 2004).*
Kimchi-Sarfaty et al., A "Silent" polymorphism in the MDR1 gene changes substrate specificity. SCIENCE, 2007, vol. 315: 525-528. (Year: 2007).*
Nackley et al., Human Catechol-O-Methytransferase haplotypes modulate protein expression by altering mRNA secondary structure. SCIENCE, 2006, vol. 314: 1930-1933. (Year: 2006).*
Sauna et al., Silent polymorphisms speak: How they affect pharmacogenomics and the treatment of cancer. Cancer Res., 2007, vol. 67(20): 9609-9612. (Year: 2007).*

(Continued)

*Primary Examiner* — Ganapathirama Raghu
(74) *Attorney, Agent, or Firm* — McAndrews, Held & Malloy, Ltd.

(57) ABSTRACT

Nodulisporic acids (NAs) comprise a group of indole diterpenes known for their potent insecticidal activities; however, biosynthesis of NAs by its natural producer, *Hypoxylon pulicicidum* (*Nodulisporium* sp.) is exceptionally difficult to achieve. The identification of genes responsible for NA production could enable biosynthetic pathway optimization to provide access to NAs for commercial applications. Obtaining useful quantities of NAs using published fermentations methods is challenging, making gene knockout studies an undesirable method to confirm gene function. Alternatively, heterologous gene expression of *H. pulicicidum* genes in a more robust host species like *Penicillium paxilli* provides a way to rapidly identify the function of genes that play a role in NA biosynthesis. In this work, we identified the function of four secondary-metabolic genes necessary for the biosynthesis of nodulisporic acid F (NAF) and reconstituted these genes in the genome of *P. paxilli* to enable heterologous production of NAF in this fungus.

15 Claims, 15 Drawing Sheets

Spec

(56) References Cited

OTHER PUBLICATIONS

International Search Report and Written Opinion corresponding to International Patent Application No. PCT/IB2018/057528 dated Dec. 13, 2018.

Nicholson M.J et al. "Molecular Cloning and Functional Analysis of Gene Clusters for the Biosynthesis of Indole-Diterpenes in Penicillium crustosum and P. janthinellum", Toxins, 2015, vol. 7, pp. 2701-2722, DOI: 10.33990/toxins7082701 Abstract, Results, Discussion.

Bills, G.F. et al. "*Hypoxylon pulicicidum* sp. nov. (*Ascomycota, Xylariales*), a Pantropical Insecticide-Producing Endophyte" PLoS One. 2012; 7(10): e46687, DOI: 10.1371/journal.pone.0046687 Abstract, Figure 1, Table 1, p. 16, "Morphology and Culture Studies" and "Fermentation for Detection of Nodulisporic Acids".

Protein Sequence, Hypoxylon pulicicidum strain MF5954 hypothetical protein, cytochrome P450 oxygenase (nodW). Genbank MG 182145.1 (Accession No. MGI82145), Published: IO—Jan. 2018 Whole Document.

Nucleotide Sequence, cytochrome P450 oxygenase [Hypoxylon pulicicidum], GenBank: AUM60065.1 (Accession No. AUM60065), Published: IO—Jan. 2018 Whole Document.

Nucleotide Sequence, cytochrome P450 oxygenase [Hypoxylon pulicicidum], GenBank: AUM60066.1 (Accession No. AUM60066), Published: IO—Jan. 2018 Whole Document.

Nucleotide Sequence, cytochrome P450 oxygenase [Hypoxylon pulicicidum], GenBank: AUM60053.1, Published: 10—Jan. 2018 Whole Document.

Van de Bittner, K.C., et al., "Heterologous Biosynthesis of Nodulisporic Acid F", 1. Am. Chern. Soc., Dec. 28, 2017, 140(2), pp. 582-585, DOI: 10.1021/jacs.7bI0909 Whole Document.

Nicholson M. et ai, "Draft Genome Sequence of the Filamentous Fungus Hypoxylon pulicicidum ATCC 74245", Genome Announcements, Il—Jan. 2018, vol. 6, No. 2, e01380-17, DOI:I0.1128/genomeA.01380-17.

\* cited by examiner (A) Simplest MIDAS format (B) Extended MIDAS format (C) Fully-enabled MIDAS format

HETEROLOGOUS BIOSYNTHESIS OF NODULISPORIC ACID

FIELD OF THE INVENTION

This invention generally relates to novel polypeptides that catalyze at least one biochemical reaction leading to the production of a nodulisporic acid (NA), polynucleotides encoding such polypeptides, methods of making such polypeptides and polynucleotides, and methods of using such polypeptides and polynucleotides to produce at least one NA by heterologous expression in a permissive host.

BACKGROUND

Filamentous fungi produce a diverse repertoire of interesting and useful chemical compounds. Members of one such class of compounds, the indole diterpenes (IDTs), are of particular interest due to their wide range of chemical diversity and concomitant bioactivities, which include anti-MRSA,[1] anti-cancer,[2,3] anti-H1N1,[4] insecticidal[5] and tremorgenic[6] activities. NAs (FIG. 1) are a group of notably bioactive quasi-paspaline-like IDTs produced by *Hypoxylon pulicicidum*, formerly classified as *Nodulisporium* sp.[7] Nodulisporic acid A (NAA) 10 is of particular significance because it exhibits highly potent insecticidal activity against blood-feeding arthropods while exhibiting no observable adverse effects on mammals.[5,8]

NAs are especially difficult to biosynthesize from the natural producer, *H. pulicicidum*. Reported NA biosynthesis methods require that *H. pulicicidum* be grown for 21 days in complete darkness in highly nutrient rich media.[9] Due to the difficulty of NAA 10 biosynthesis in *H. pulicicidum*, obtaining useful quantities of NAA 10 using published fermentations methods is challenging, and production of commercial quantities of NAA 10 essentially unachievable. Accordingly, attempts have been made to chemically synthesize NAA 10 resulting in mechanisms for the synthesis of nodulisporic acid F (NAF) 5a[10] and nodulisporic acid D 7a,[11] but full synthesis of NAA 10 has not been achieved.[12] Consequently there is a need in the art for new methods of NAA 10 synthesis and/or biosynthesis that will provide useful quantities of NAA 10.

It is an object of the present invention to provide a polynucleotide encoding at least one enzyme in the NAA 10 biosynthesis pathway of *H. pulicicidum* and/or to provide a method of using such a vector to produce at least one indole diterpene compound that is a NA and/or to produce a precursor to NAA 10 in a heterologous host and/or to at least provide the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In one aspect the invention relates to an isolated polypeptide comprising an amino acid sequence selected from the group consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In another aspect the invention relates to an isolated polynucleotide encoding a polypeptide comprising an amino acid sequence selected from the group consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In another aspect the invention relates to an isolated polynucleotide comprising at least 70% nucleic acid sequence identity to a nucleic acid sequence selected from the group consisting of nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO: 13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

In another aspect the invention relates to a transcription unit (TU) comprising at least one isolated polynucleotide according to the invention.

In another aspect the invention relates to a vector that encodes an isolated polypeptide according to the invention.

In another aspect the invention relates to a vector comprising an isolated nucleic acid sequence or a TU according to the invention.

In another aspect the invention relates to an isolated host cell comprising an isolated polypeptide, isolated polynucleotide, TU and/or vector according to the invention.

In another aspect the invention relates to a method of making at least one NA comprising heterologously expressing at least one polypeptide, isolated nucleic acid sequence, TU or vector according to the invention in an isolated host cell.

In another aspect the invention relates to at least one NA made by a method of the invention.

In another aspect the present invention relates to an isolated polypeptide or functional fragment or variant thereof from *Hypoxylon* spp. that catalyzes a biochemical reaction in the biosynthetic pathway leading from 3-geranylgeranyl indole (GGI) 2 to NAA 10.

In another aspect the present invention relates to an isolated polynucleotide encoding at least one polypeptide or functional variant or fragment thereof from *Hypoxylon* spp. that catalyzes a biochemical reaction in the biosynthetic pathway leading from GGI 2 to NAA 10.

In another aspect the invention relates to a method of making at least one *Hypoxylon* spp. polypeptide or functional variant or fragment thereof comprising heterologously expressing an isolated nucleic acid sequence or vector according to the invention in an isolated host cell.

In another aspect the invention relates to a method of making at least one NA comprising heterologously expressing in an isolated host cell, at least one polypeptide that catalyzes a biochemical reaction in the biosynthetic pathway leading from GGI 2 to NAA 10.

In another aspect the invention relates to an isolated host cell that expresses at least one heterologous polypeptide that catalyzes the transformation of a substrate in the biosynthetic pathway leading from GGI 2 to the formation of NAA 10.

In another aspect the invention relates to an isolated host cell that produces by heterologous expression, at least one polypeptide involved in the biosynthetic pathway leading from GGI 2 to NAA 10.

In another aspect the invention relates to a method of producing at least one NA comprising contacting a carbohydrate comprising substrate with a recombinant cell transformed with a nucleic acid that results in an increased level of activity of a polypeptide selected from the group consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof compared to the cell prior to transformation, such that the substrate is metabolized to at least one NA.

In another aspect the invention relates to an isolated strain of *Hypoxylon pulicicidum* that comprises at least one heterologous nucleic acid sequence encoding an enzyme in a biosynthetic pathway leading to NAA10.

In another aspect the invention relates to an isolated strain of *Hypoxylon pulicicidum* that expresses at least two different GGPPS enzymes.

In another aspect the invention relates to an isolated strain of *Hypoxylon pulicicidum* that comprises a genetic modification that leads to an increased biosynthesis of NAA 10.

In another aspect the invention relates to a method of making NAA 10 comprising expressing at least one heterologous nucleic acid sequence in *Hypoxylon pulicicidum*, wherein the at least one heterologous nucleic acid sequence encodes an enzyme in a biosynthetic pathway leading to NAA 10.

Various embodiments of the different aspects of the invention as discussed above are also set out below in the detailed description of the invention, but the invention is not limited thereto.

Other aspects of the invention may become apparent from the following description which is given by way of example only and with reference to the accompanying drawings.

BRIEF DESCRIPTION OF THE DRAWINGS

The invention will now be described with reference to the figures in the accompanying drawings.

DETAILED DESCRIPTION OF THE INVENTION

Definitions

Figure 1:
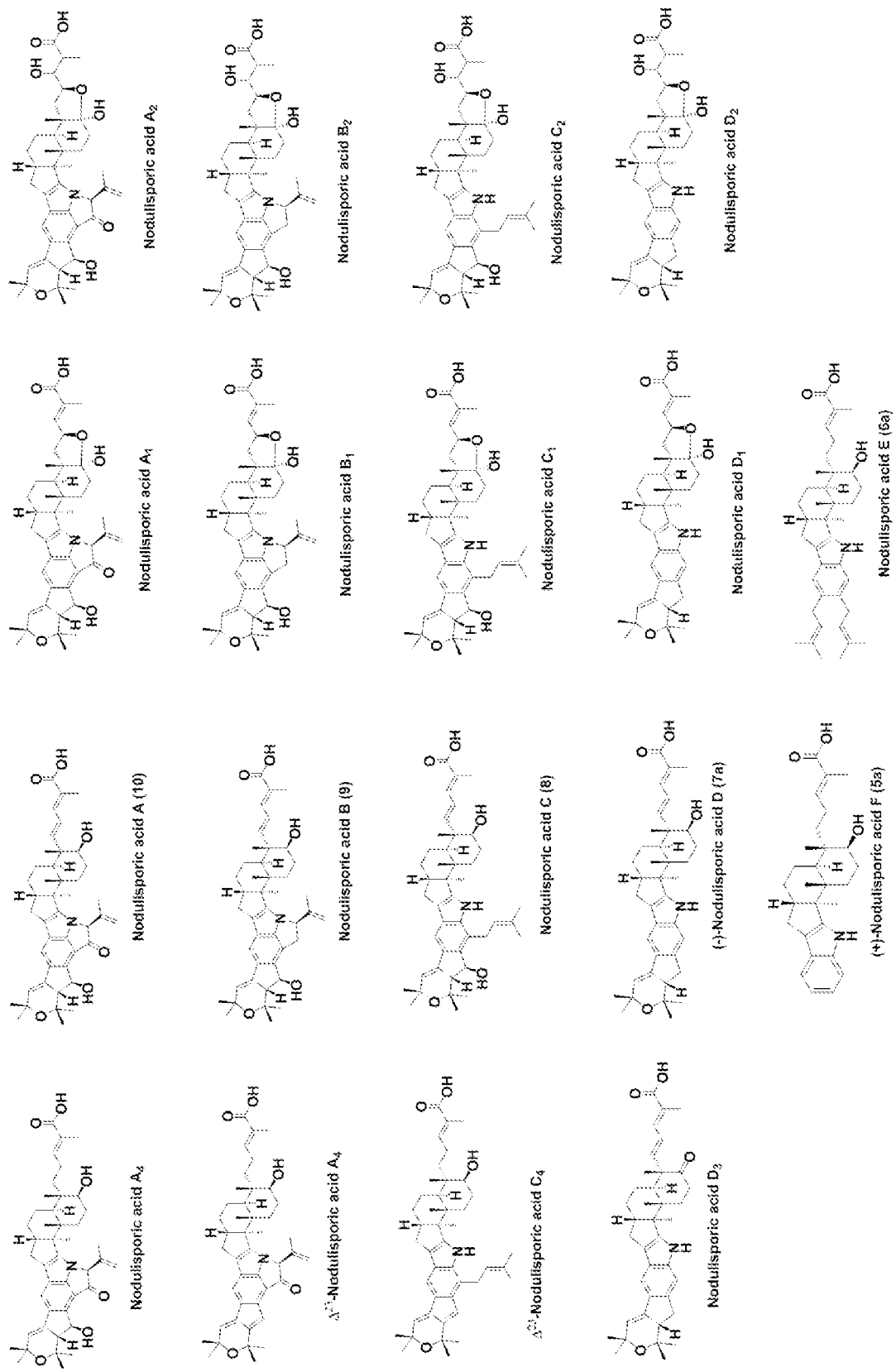
FIG. 1: Collection of known nodulisporic acids (NAs).

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

The term "consisting essentially of" as used herein means the specified materials or steps and those that do not materially affect the basic and novel characteristic(s) of the claimed invention.

The term "consisting of" as used herein means the specified materials or steps of the claimed invention, excluding any element, step, or ingredient not specified in the claim.

The terms "recognition site" and "restriction site" are used interchangeably herein and mean the same thing. These terms as used herein with reference to a restriction enzyme mean the nucleic acid sequence or sequences of a polynucleotide that define the binding site on the polynucleotide for a given restriction enzyme.

The term "indole diterpene (IDT) compound" or "indole diterpenoid" refers to any compound derived from an indole containing precursor, preferably indole-3-glycerol phosphate 1b, and geranylgeranyl pyrophosphate (GGPP) 1a.

In some embodiments an IDT compound is selected from the group consisting of GGI 2, emindole SB 4a, and NAF 5a.

The term "genetic construct" refers to a polynucleotide molecule, usually double-stranded DNA, which has been conjugated to another polynucleotide molecule. In one non-limiting example a genetic construct is made by inserting a first polynucleotide molecule into a second polynucleotide molecule, for example by restriction/ligation as known in the art. In some embodiments, a genetic construct comprises a single polynucleotide module, at least two polynucleotide modules, or a series of multiple polynucleotide modules assembled into a single contiguous polynucleotide molecule (also referred to herein as a "multigene construct"), but not limited thereto.

The term "genetic construct" refers to a polynucleotide molecule, usually double-stranded DNA, which has been conjugated to another polynucleotide molecule. In one non-limiting example a genetic construct is made by inserting a first polynucleotide molecule into a second polynucleotide molecule, for example by restriction/ligation as known in the art.

In some embodiments, a genetic construct comprises a single polynucleotide module, at least two polynucleotide modules, or a series of multiple polynucleotide modules assembled into a single contiguous polynucleotide molecule (also referred to herein as a "multigene construct"), but not limited thereto.

A genetic construct may contain the necessary elements that permit transcription of a polynucleotide molecule, and, optionally, for translating the transcript into a polypeptide. A polynucleotide molecule comprised in and/or by the gene construct may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "transcription unit" (TU) as used herein refers to a polynucleotide comprising a sequence of nucleotides that code for a single RNA molecule including all the nucleotide sequences necessary for transcription of the single RNA molecule, including a promoter, an RNA-coding sequence, and a terminator, but not limited thereto.

The term "transcription unit module" (TUM) as used herein refers to a polynucleotide comprising a sequence of nucleotides that encode a single RNA molecule, or parts thereof; or that encode a protein coding sequence (CDS), or parts thereof; or that encode sequence elements, or parts thereof, that control transcription of that RNA molecule; or that encode sequence elements or parts thereof that control translation of the CDS. Such sequence elements may include, but are not limited to, promoters, untranslated regions (UTRs), terminators, polyadenylation signals, ribosome binding sites, transcriptional enhancers and translational enhancers.

The term "multigene construct" as used herein means a genetic construct that is a polynucleotide comprising at least two TUs.

The term "marker" as used herein means a nucleic acid sequence in a polynucleotide that encodes a selectable marker or scorable marker.

The term "selectable marker" as used herein refers to a TU, which when introduced into a cell, confers at least one trait on the cell that allows the cell to be selected based on the presence or absence of that trait. In one embodiment the cell is selected based on survival under conditions that kill cells not comprising the at least one selectable marker.

The term "scorable marker" as used herein refers to a TU, which when introduced into a cell, confers at least one trait on the cell that allows the cell to be scored based on the presence or absence of that trait. In one embodiment the cell comprising the TU is scored by identifying the cell phenotypically from a plurality of cells.

The term "genetic element" as used herein refers to any polynucleotide sequence that is not a TU or does not form part of a TU. Such polynucleotide sequences may include, but are not limited to origins of replication for plasmids and viruses, centromeres, telomeres, repeat sequences, sequences used for homologous recombination, site-specific recombination sequences, and sequences controlling DNA transfer between organisms.

The term "vector" as used herein refers to any type of polynucleotide molecule that may be used to manipulate genetic material so that it can be amplified, replicated, manipulated, partially replicated, modified and/or expressed, but not limited thereto. In some embodiments a vector may be used to transport a polynucleotide comprised in that vector into a cell or organism.

The term "source vector" as used herein refers to a vector into which polynucleotide sequences of interest can be cloned. In some embodiments the polynucleotide sequences are TUs and TUMs as described herein. In some embodiments a source vector is selected from the group consisting of plasmids, bacterial artificial chromosomes (BACs), phage artificial chromosomes (PACs), yeast artificial chromosomes (YACs), bacteriophage, phagemids, and cosmids. In some embodiments, a source vector comprising a polynucleotide sequence of interest is termed an entry clone. In some embodiments the entry clone can serve as a shuttle or destination vector for receiving further polynucleotide sequences.

The term "shuttle vector" as used herein refers to a vector into which polynucleotide sequences of interest can be cloned and from which they can be manipulated. In some embodiments the polynucleotide sequences are TUs and TUMs as described herein. In some embodiments a shuttle vector is selected from the group consisting of plasmids, BACs, PACs, YACs, bacteriophage, phagemids, and cosmids. In some embodiments, a shuttle vector comprising a polynucleotide sequence of interest can serve as a destination vector for receiving further polynucleotide sequences.

The term "destination vector" as used herein refers to a vector into which polynucleotide sequences of interest can be cloned. In some embodiments the polynucleotide sequences are TUs and TUMs as described herein. In some embodiments a destination vector is selected from the group consisting of plasmids, BACs, PACs, YACs, bacteriophage, phagemids, and cosmids. In some embodiments, a destination vector comprising a polynucleotide sequence of interest is an entry clone. In some embodiments the entry clone can serve as a destination vector for receiving further polynucleotide sequences.

The term "polynucleotide(s)," as used herein, means a single or double-stranded deoxyribonucleotide or ribonucleotide polymer of any length, and include as non-limiting examples, coding and non-coding sequences of a gene, sense and antisense sequences, exons, introns, genomic DNA, cDNA, pre-mRNA, mRNA, rRNA, siRNA, miRNA, tRNA, ribozymes, recombinant polynucleotides, isolated and purified naturally occurring DNA or RNA sequences, synthetic RNA and DNA sequences, nucleic acid probes, primers, fragments, genetic constructs, vectors and modified polynucleotides. Reference to nucleic acids, nucleic acid molecules, nucleotide sequences and polynucleotide sequences is to be similarly understood.

The term "gene" as used herein refers to gene the biologic unit of heredity, self-reproducing and located at a definite position (locus) on a particular chromosome. In one embodiment the particular chromosome is a eukaryotic or bacterial chromosome. The term bacterial chromosome is used interchangeably herein with the term bacterial genome.

The term "gene cluster" as used herein refers to a group of genes located closely together on the same chromosome whose products play a coordinated role in a specific aspect of cellular primary or secondary metabolism. In one example a gene cluster comprises a group of CDSs the products of which all participate in a series of biochemical reactions that comprise the biosynthetic pathway or array that produces a given metabolite, particularly a secondary metabolite.

The term "secondary metabolite" as used herein refers to compounds that are not involved in primary metabolism, and therefore differ from the more prevalent macromolecules such as proteins and nucleic acids that make up the basic machinery of life.

The terms "under conditions wherein the . . . enzyme is active" and "under conditions wherein the . . . enzymes are active", and grammatical variations thereof when used in reference to enzyme activity mean that the enzyme will perform it's expected function; e.g., a restriction endonuclease will cleave a nucleic acid at an appropriate restriction site, and a DNA ligase will covalently join two polynucleotides together.

The term "endogenous" as used herein refers to a constituent of a cell, tissue or organism that originates or is produced naturally within that cell, tissue or organism. An "endogenous" constituent may be any constituent including but not limited to a polynucleotide, a polypeptide including a non-ribosomal polypeptide, a fatty acid or a polyketide, but not limited thereto.

The term "exogenous" as used herein refers to any constituent of a cell, tissue or organism that does not originate or is not produced naturally within that cell, tissue or organism. An exogenous constituent may be, for example, a polynucleotide sequence that has been introduced into a cell, tissue or organism, or a polypeptide expressed in that cell, tissue or organism from that polynucleotide sequence.

"Naturally occurring" as used herein with reference to a polynucleotide sequence according to the invention refers to a primary polynucleotide sequence that is found in nature. A synthetic polynucleotide sequence that is identical to a wild polynucleotide sequence is, for the purposes of this disclosure, considered a naturally occurring sequence. What is important for a naturally occurring polynucleotide sequence is that the actual sequence of nucleotide bases that comprise the polynucleotide is found or known from nature.

For example, a wild type polynucleotide sequence is a naturally occurring polynucleotide sequence, but not limited thereto. A naturally occurring polynucleotide sequence also refers to variant polynucleotide sequences as found in nature that differ from wild type. For example, allelic variants and naturally occurring recombinant polynucleotide sequences due to hybridization or horizontal gene transfer, but not limited thereto.

"Non-naturally occurring" as used herein with reference to a polynucleotide sequence according to the invention refers to a polynucleotide sequence that is not found in nature. Examples of non-naturally occurring polynucleotide sequences include artificially produced mutant and variant polynucleotide sequences, made for example by point mutation, insertion, or deletion, but not limited thereto. Non-naturally occurring polynucleotide sequences also include chemically evolved sequences. What is important for a non-naturally occurring polynucleotide sequence according to the invention is that the actual sequence of nucleotide bases that comprise the polynucleotide is not found or known from nature.

The term, "wild type" when used herein with reference to a polynucleotide refers to a naturally occurring; non-mutant form of a polynucleotide. A mutant polynucleotide means a polynucleotide that has sustained a mutation as known in the art, such as point mutation, insertion, deletion, substitution, amplification or translocation, but not limited thereto.

The term, "wild type" when used herein with reference to a polypeptide refers to a naturally occurring, non-mutant form of a polypeptide. A wild type polypeptide is a polypeptide that is capable of being expressed from a wild type polynucleotide.

The term "coding sequence" or "open reading frame" (ORF) refers to the sense strand of a genomic DNA sequence or a cDNA sequence that is capable of producing a transcription product and/or a polypeptide under the control of appropriate regulatory sequences. The CDS is identified by the presence of a 5' translation start codon and a 3' translation stop codon. When inserted into a genetic construct or an expression cassette, a "coding sequence" (CDS) is capable of being expressed when it is operably linked to a promoter sequence and/or other regulatory elements.

"Operably-linked" means that the sequence to be expressed is placed under the control of regulatory elements.

"Regulatory elements" as used herein refers to any nucleic acid sequence element that controls or influences the expression of a polynucleotide insert from a vector, genetic construct or expression cassette and includes promoters, transcription control sequences, translation control sequences, origins of replication, tissue-specific regulatory elements, temporal regulatory elements, enhancers, polyadenylation signals, repressors and terminators. Regulatory elements can be "homologous" or "heterologous" to the polynucleotide insert to be expressed from a genetic construct, expression cassette or vector as described herein. When a genetic construct, expression cassette or vector as described herein is present in a cell, a regulatory element can be "endogenous", "exogenous", "naturally occurring" and/or "non-naturally occurring" with respect to cell.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate the transcription of a polynucleotide sequence. Promoters comprise cis-initiator elements which specify the transcription initiation site and conserved boxes. In one non-limiting example, bacterial promoters may comprise a "Pribnow box" (also known as the −10 region), and other motifs that are bound by transcription factors and promote transcription. Promoters can be homologous or heterologous with respect to polynucleotide sequence to be expressed. When the polynucleotide sequence is to be expressed in a cell, a promoter may be an endogenous or exogenous promoter. Promoters can be constitutive promoters, inducible promoters or regulatable promoters as known in the art.

"Homologous" as used herein with reference to polynucleotide regulatory elements, means a polynucleotide regulatory element that is a native and naturally-occurring polynucleotide regulatory element. A homologous polynucleotide regulatory element may be operably linked to a polynucleotide of interest such that the polynucleotide of interest can be expressed from a TU, genetic element or vector according to the invention.

"Homologous" as used herein with reference to polynucleotide or polypeptide in a host organism means that the polynucleotide or polypeptide is a native and naturally-occurring polynucleotide or polynucleotide within that host organism. A homologous polynucleotide may be operably linked to a homologous or heterologous regulatory element so that a homologous polypeptide may be expressed from a TU, genetic element or vector comprising the homologous polynucleotide as described herein.

"Introduced Homologous" as used herein with reference to polynucleotide or polypeptide in a host organism means that the polynucleotide or polypeptide is a native and naturally-occurring polynucleotide or polynucleotide within that host organism that has been introduced into the organism by experimental techniques. A introduced homologous polynucleotide may be operably linked to a homologous or heterologous regulatory element so that a homologous polypeptide may be expressed from a TU, genetic element or vector comprising the homologous polynucleotide as described herein.

"Heterologous" as used herein with reference to polynucleotide regulatory elements, means a polynucleotide regulatory element that is not a native and naturally-occurring polynucleotide regulatory element. A heterologous polynucleotide regulatory element is not normally associated with the CDS to which it is operably linked. A heterologous regulatory element may be operably linked to a polynucleotide of interest such that the polynucleotide of interest can be expressed from a, vector, genetic construct or expression cassette according to the invention. Such promoters may include promoters normally associated with other genes, ORFs or coding regions, and/or promoters isolated from any other bacterial, viral, eukaryotic, or mammalian cell.

"Heterologous" as used herein with reference to a polynucleotide or polypeptide in a host organism means a polynucleotide or polypeptide that is not a native and naturally-occurring polynucleotide or polypeptide in that host organism. A heterologous polynucleotide may be operably linked to a heterologous or homologous regulatory element so that a heterologous polypeptide may be expressed from a TU, genetic element or vector comprising the heterologous polynucleotide as described herein.

The terms "heterologously expressing" and "heterologous expression" mean the expression of a heterologous polypeptide in a host cell.

A "biochemical reaction in the biosynthetic pathway leading from GGI 2 to NAA 10" means one of the specific reactions catalyzed by one of the specific enzymes involved in transforming the substrate molecule GGI 2 through the following intermediates: mono-expoxidized GGI 3a, emindole SB 4a, NAF 5a, NAE 6a, NAD 7a, NAC 8, NAB 9, to NAA 10, and does not include similar enzymes within a host cell that may have similar functions but that do not act on the particular named intermediates above.

A "functional variant or fragment thereof" of a polypeptide is a subsequence of the polypeptide that performs a function that is required for the biological activity or binding of that polypeptide and/or provides the three dimensional structure of the polypeptide. The term may refer to a polypeptide, an aggregate of a polypeptide such as a dimer or other multimer, a fusion polypeptide, a polypeptide fragment, a polypeptide variant, or functional polypeptide derivative thereof that is capable of performing the polypeptide activity.

"Isolated" as used herein with reference to polynucleotide or polypeptide sequences describes a sequence that has been removed from its natural cellular environment. An isolated molecule may be obtained by any method or combination of methods as known and used in the art, including biochemical, recombinant, and synthetic techniques. The polynucleotide or polypeptide sequences may be prepared by at least one purification step.

"Isolated" when used herein in reference to a cell or host cell describes to a cell or host cell that has been obtained or removed from an organism or from its natural environment and is subsequently maintained in a laboratory environment as known in the art. The term encompasses single cells, per se, as well as cells or host cells comprised in a cell culture and can include a single cell or single host cell.

The term "isolated host cell" as used herein with reference to a fungal host cell encompasses single cells of unicellular fungi and the hyphae and mycelia of filamentous fungi including septate and non-septate forms.

The term "recombinant" refers to a polynucleotide sequence that is removed from sequences that surround it in its natural context and/or is recombined with sequences that are not present in its natural context. A "recombinant" polypeptide sequence is produced by translation from a "recombinant" polynucleotide sequence.

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the polypeptides useful in the invention have biological activities that are the same or similar to those of a corresponding wild type molecule; i.e., the parent polypeptides or polynucleotides.

In certain embodiments, variants of the polypeptides described herein have biological activities that are similar, or that are substantially similar to their corresponding wild type molecules. In certain embodiments the similarities are similar activity and/or binding specificity.

In certain embodiments, variants of polypeptides described herein have biological activities that differ from their corresponding wild type molecules. In certain embodiments the differences are altered activity and/or binding specificity.

The term "variant" with reference to polynucleotides and polypeptides encompasses all forms of polynucleotides and polypeptides as defined herein.

Variant polynucleotide sequences preferably exhibit at least 50%, at least 60%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, and preferably at least 99% identity to a sequence of the present invention. Identity is found over a comparison window of at least 8 nucleotide positions, preferably at least 10 nucleotide positions, preferably at least 15 nucleotide positions, preferably at least 20 nucleotide positions, preferably at least 27 nucleotide positions, preferably at least 40 nucleotide positions, preferably at least 50 nucleotide positions, preferably at least 60 nucleotide positions, preferably at least 70 nucleotide positions, preferably at least 80 nucleotide positions, preferably over the entire length of a polynucleotide used in or identified according to a method of the invention.

Polynucleotide variants also encompass those which exhibit a similarity to one or more of the specifically identified sequences that is likely to preserve the functional equivalence of those sequences and which could not reasonably be expected to have occurred by random chance.

Polynucleotide sequence identity and similarity can be determined readily by those of skill in the art.

Variant polynucleotides also encompasses polynucleotides that differ from the polynucleotide sequences described herein but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

The term "variant" with reference to polypeptides also encompasses naturally occurring, recombinantly and synthetically produced polypeptides. Variant polypeptide sequences preferably exhibit at least 35%, preferably at least 40%, preferably at least 50%, preferably at least 60%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, and preferably at least 99% identity to a sequence of the present invention. Identity is found over a comparison window of at least 2 amino acid positions, preferably at least 3 amino acid positions, preferably at least 4 amino acid positions, preferably at least 5 amino acid positions, preferably at least 7 amino acid positions, preferably at least 10 amino acid positions, preferably at least 15 amino acid positions, preferably at least 20 amino acid positions, preferably over the entire length of a polypeptide used in or identified according to a method of the invention.

Polypeptide variants also encompass those which exhibit a similarity to one or more of the specifically identified sequences that is likely to preserve the functional equivalence of those sequences and which could not reasonably be expected to have occurred by random chance.

Polypeptide sequence identity and similarity can be determined readily by those of skill in the art.

A variant polypeptide includes a polypeptide wherein the amino acid sequence differs from a polypeptide herein by one or more conservative amino acid or non-conservative substitutions, deletions, additions or insertions which do not affect the biological activity of the peptide.

Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine.

Analysis of evolved biological sequences has shown that not all sequence changes are equally likely, reflecting at least in part the differences in conservative versus non-conservative substitutions at a biological level. For example, certain amino acid substitutions may occur frequently, whereas others are very rare. Evolutionary changes or substitutions in amino acid residues can be modelled by a scoring matrix also referred to as a substitution matrix. Such matrices are used in bioinformatics analysis to identify relationships between sequences and are known to the skilled worker.

Other variants include peptides with modifications which influence peptide stability. Such analogs may contain, for example, one or more non-peptide bonds (which replace the peptide bonds) in the peptide sequence. Also included are analogs that include residues other than naturally occurring L-amino acids, e.g. D-amino acids or non-naturally occurring synthetic amino acids, e.g. beta or gamma amino acids and cyclic analogs.

Substitutions, deletions, additions or insertions may be made by mutagenesis methods known in the art. A skilled worker will be aware of methods for making phenotypically silent amino acid substitutions. See for example Bowie et al., 1990, Science 247, 1306.

A polypeptide as used herein can also refer to a polypeptide that has been modified during or after synthesis, for example, by biotinylation, benzylation, glycosylation, phosphorylation, amidation, by derivatization using blocking/ protecting groups and the like. Such modifications may increase stability or activity of the polypeptide.

The terms "modulate(s) expression", "modulated expression" and "modulating expression" of a polynucleotide or polypeptide, are intended to encompass the situation where genomic DNA corresponding to a polynucleotide to be expressed according to the invention is modified thus leading to modulated expression of a polynucleotide or polypeptide of the invention. Modification of the genomic DNA may be through genetic transformation or other methods known in the art for inducing mutations. The "modulated expression" can be related to an increase or decrease in the amount of messenger RNA and/or polypeptide produced and may also result in an increase or decrease in the activity of a polypeptide due to alterations in the sequence of a polynucleotide and polypeptide produced.

The terms "modulate(s) activity", "modulated activity" and "modulating activity" of a polynucleotide or polypeptide, are intended to encompass the situation where genomic DNA corresponding to a polynucleotide to be expressed according to the invention is modified thus leading to modulated expression of a polynucleotide or modulated expression or activity of polypeptide of the invention. Modification of the genomic DNA may be through genetic transformation or other methods known in the art for inducing mutations. The "modulated activity" can be related to an increase or decrease in the amount of messenger RNA and/or polypeptide produced and may also result in an increase or decrease in the functional activity of a polypeptide due to alterations in the sequence of a polynucleotide and polypeptide produced.

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

DETAILED DESCRIPTION

Figure 2:
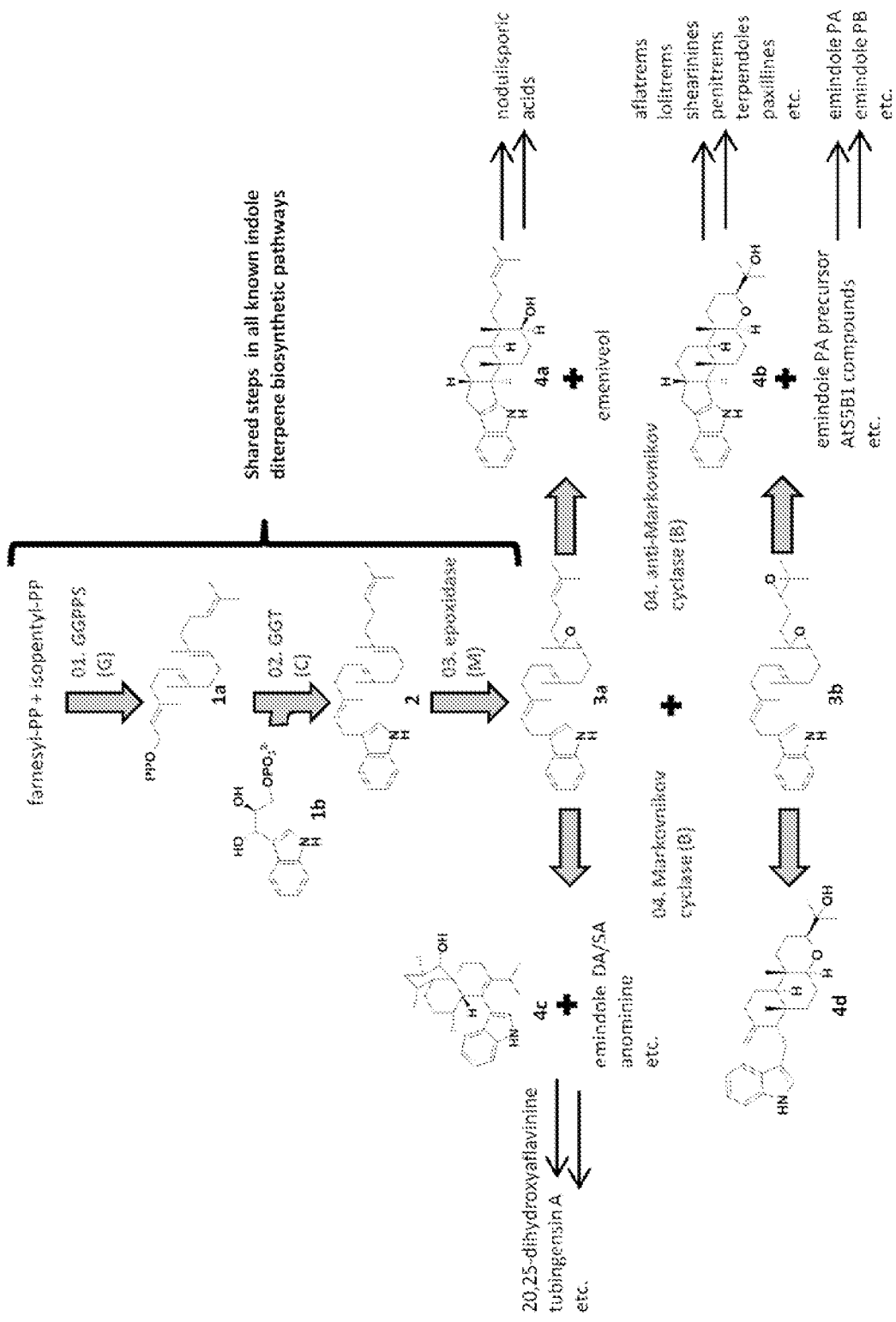
FIG. 2: Branch points in the biosynthetic pathway of indole diterpenes (IDTs) that give rise to the diverse array of IDT structures. Arrows represent enzymatic steps in IDT biosynthesis.
Figure 3:
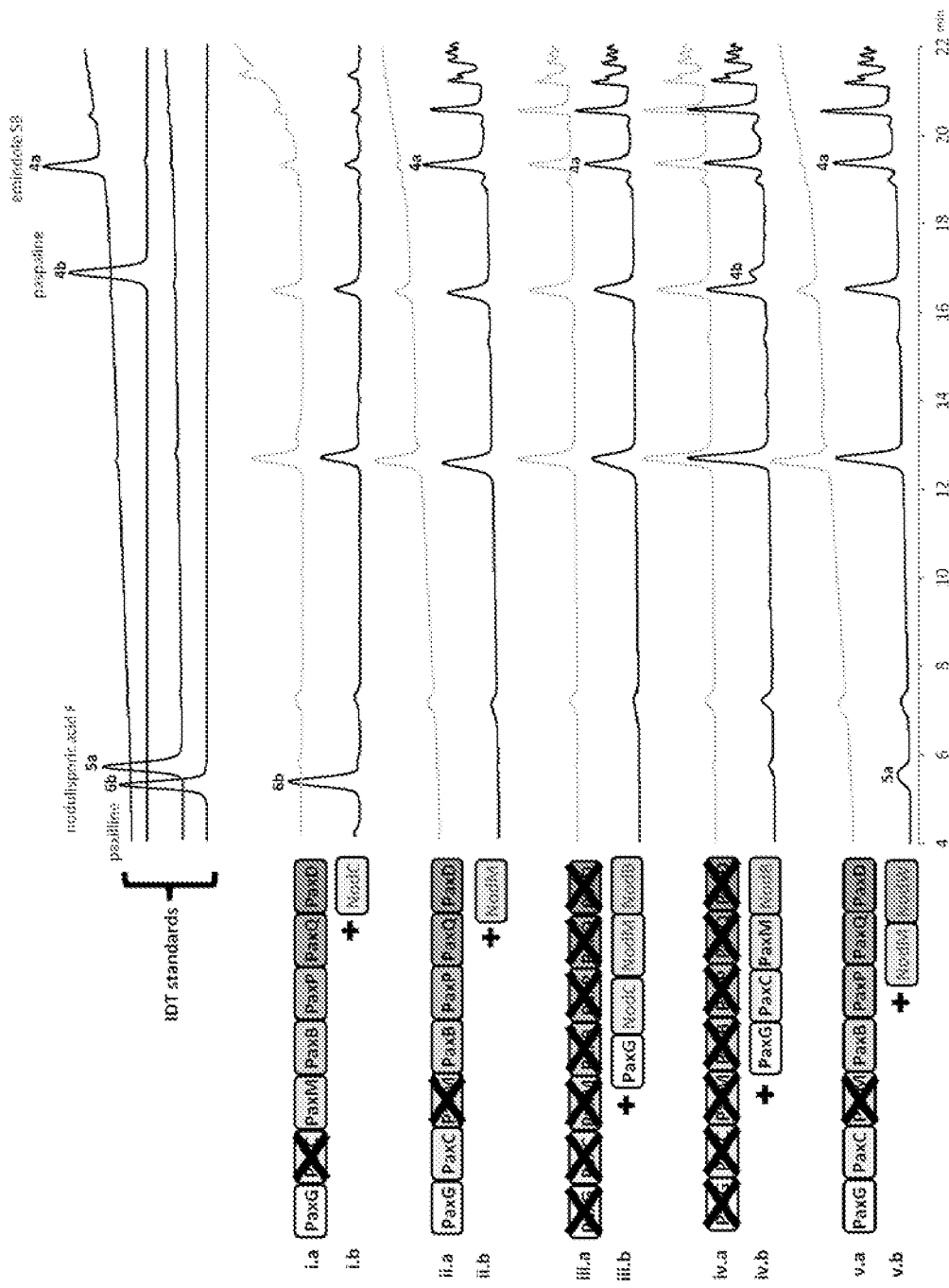
FIG. 3: HPLC analysis (271 nm) of extracts of *P. paxilli* knockout (KO) strains (in gray ( . . . )) expressing different *H. pulicicidum* (Nod) enzymes and/or *P. paxilli* (Pax) enzymes (in black (■)). A black X covers the enzyme(s) that are not expressed in the *P. paxilli* KO strains (traces i.a, ii.a, iii.a, iv.a, and v.a). The enzyme(s) that have been newly expressed in the *P. paxilli* KO strain are depicted below the corresponding KO strain and next to their UV traces (i.b, ii.b, iii.b, iv.b, and v.b). Notably there is a compound that elutes at the same retention time as emindole SB 4*a*, but emindole SB 4*a* is only present in three traces (ii.b, iii.b, and v.b) as confirmed by corresponding 406.31±0.01 m/z EICs (FIGS. 5, 6, and 9). Traces correspond to fungal extracts as follows: i.a=PN2290, i.b=pKV27:PN2690, ii.a=PN2257, ii.b=pKV63:PN2257, iii.a=PN2250, iii.b=pSK66:PN2250, iv.a=PN2250, iv.b=pKV74:PN2250, v.a=PN2257, v.b=pKV64:PN2257.
Figure 4:
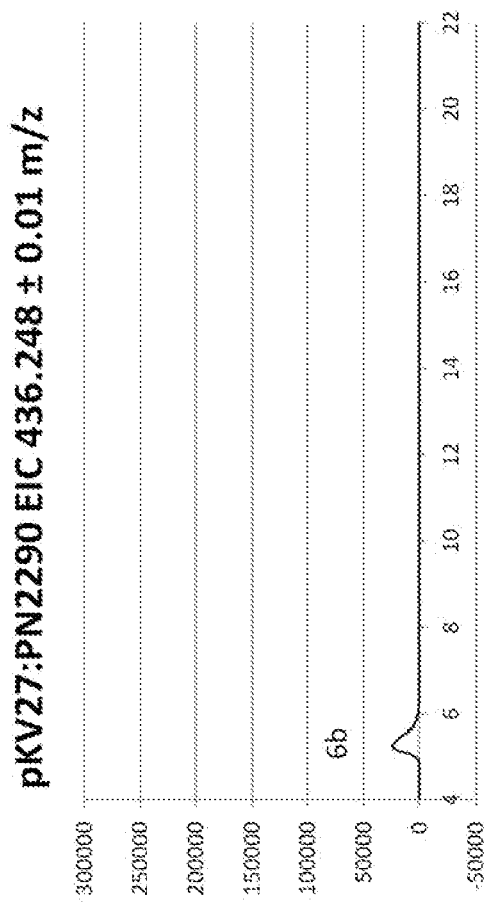
FIG. 4: Extracted ion chromatogram for pKV27:PN2290 (nodC:ΔpaxC) showing MS peak for paxilline 6*b* (5.3 min, 436.248±0.01 m/z).
Figure 5:
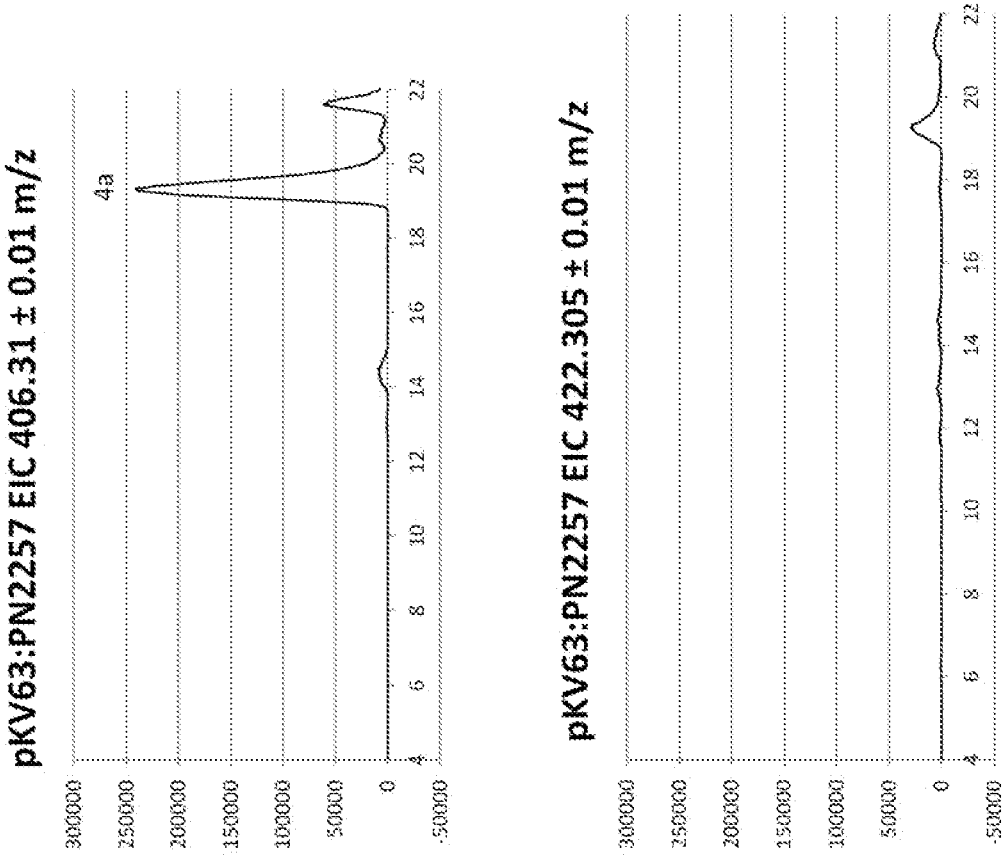
FIG. 5: Extracted ion chromatograms for pKV63:PN2257 (nodM:ΔpaxM) showing MS peak for emindole SB 4*a* (19.3 min, 406.31±0.01 m/z) but not paspaline 4*b* (17.6 min, 422.305±0.01 m/z).
Figure 6:
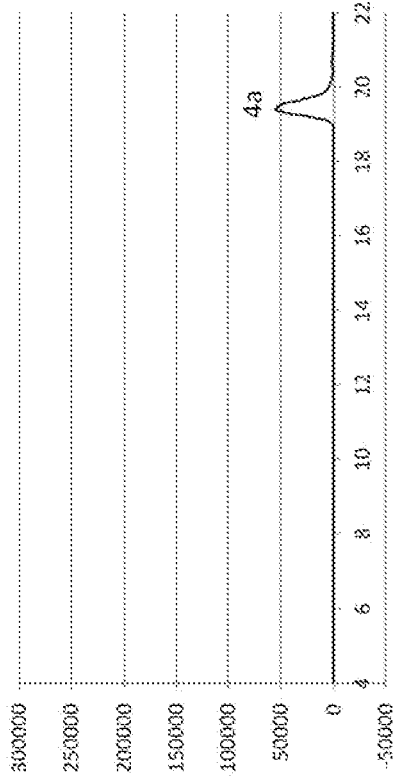
FIG. 6: Extracted ion chromatograms for pSK66:PN2250 (paxG, nodC, nodM, and nodB:ΔPAX cluster) showing MS peak for emindole SB 4*a* (19.3 min, 406.31±0.01 m/z) but not paspaline 4*b* (17.6 min, 422.305±0.01 m/z).
Figure 6:
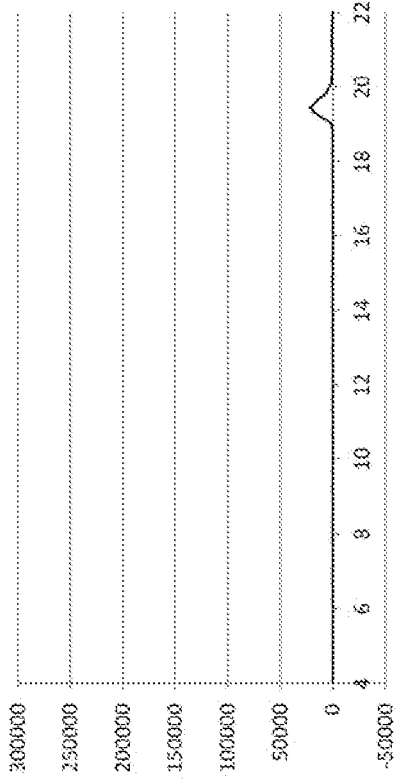
Figure 7:
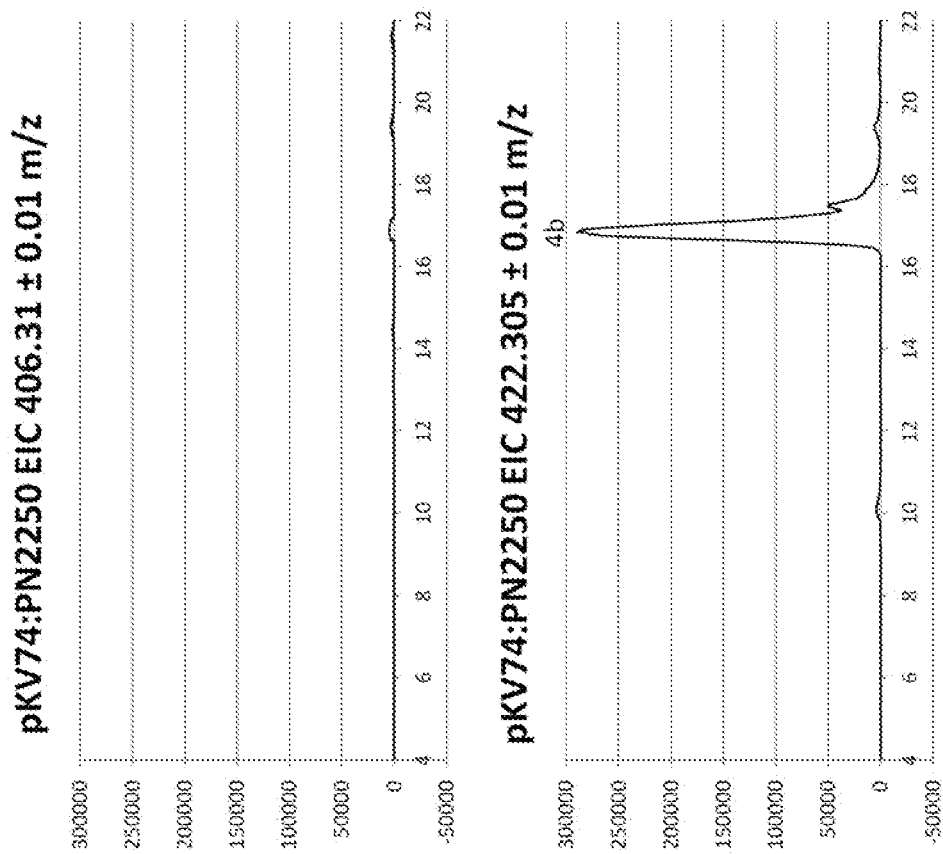
FIG. 7: Extracted ion chromatogram for pKV74:PN2250 (paxG, paxC, paxM, nodB:ΔPAX cluster) showing MS peak for paspaline 4*b* (17.6 min, 422.305±0.01 m/z) but not emindole SB 4*a* (19.3 min, 406.31±0.01 m/z).
Figure 8:
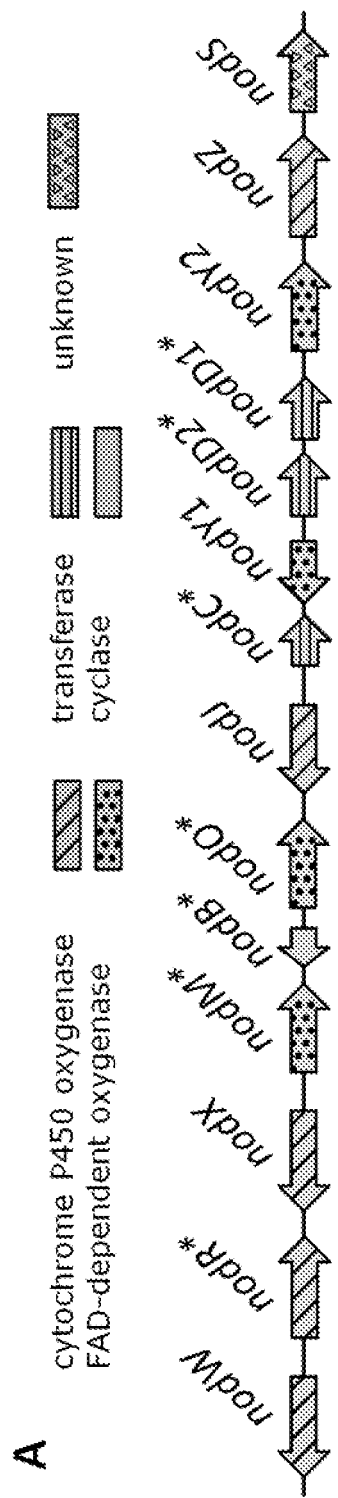
FIG. 8: Depiction of the predicted NA gene cluster from *H. pulicicidum* (A) and the NAF 5*a* biosynthetic pathway (B). Arrows represent individual genes and arrow decorations represent gene function. Figure is not to exact scale and does not include exon/intron structure. Notably the gene cluster lacks a GGPPS responsible for the first secondary-metabolic step in IDT synthesis.
Figure 8:
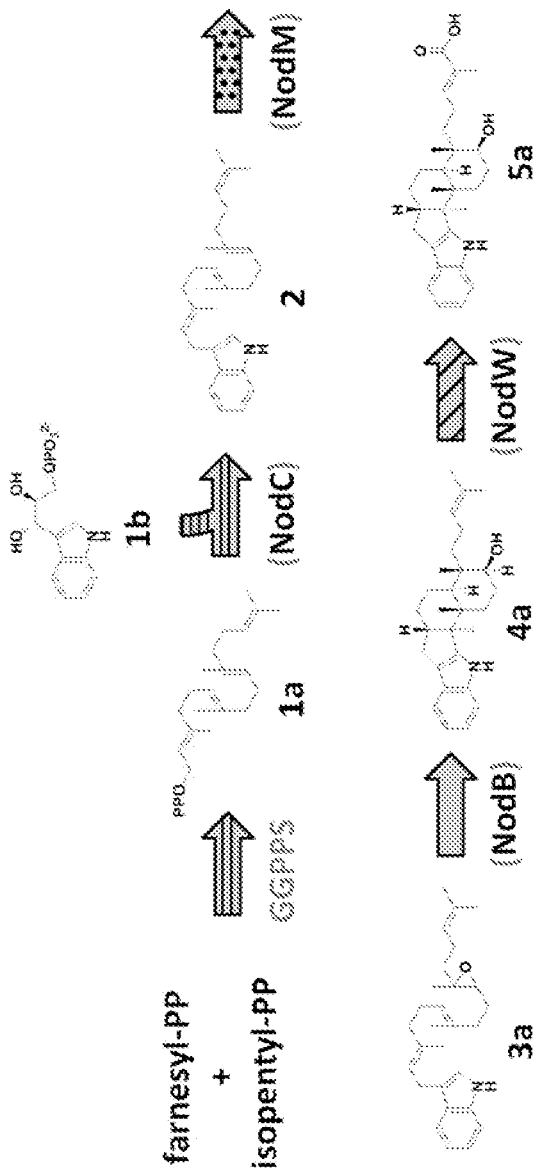
Figure 9:
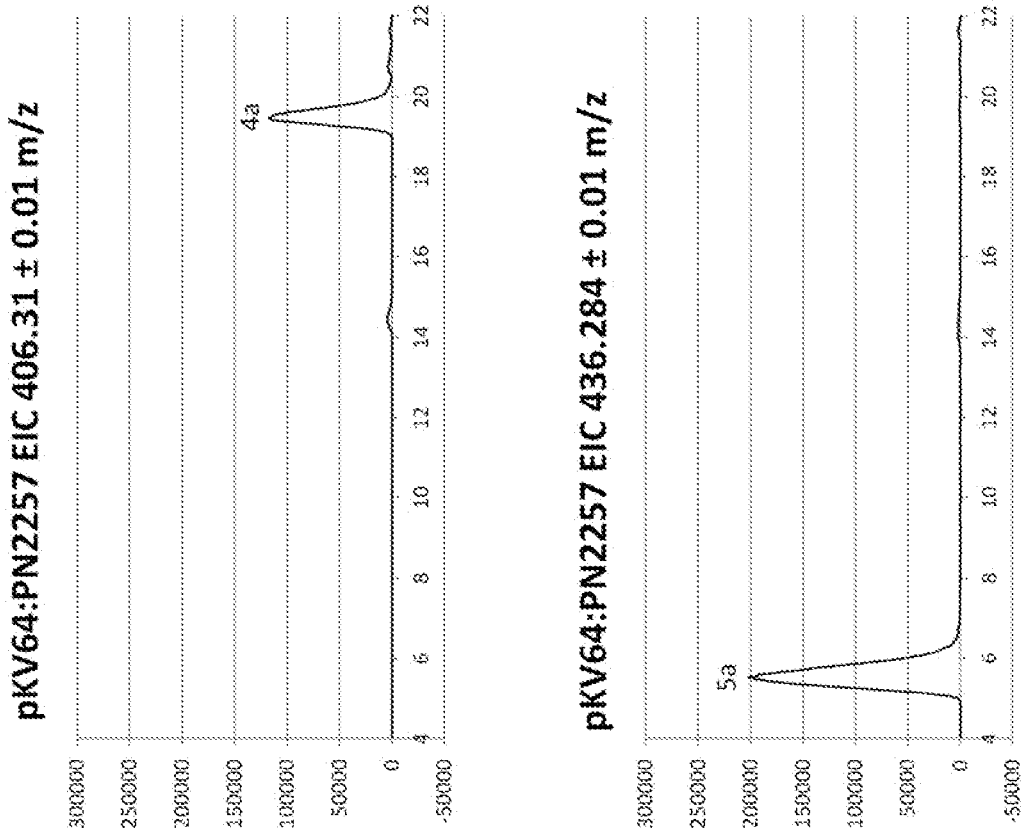
FIG. 9: Extracted ion chromatograms for pKV64:PN2257 (nodM and nodW:ΔpaxM) showing MS peaks for emindole SB 4*a* (19.3 min, 406.31±0.01 m/z) and NAF 5*a* (6.2 min, 436.284±0.01 m/z).
Figure 10:
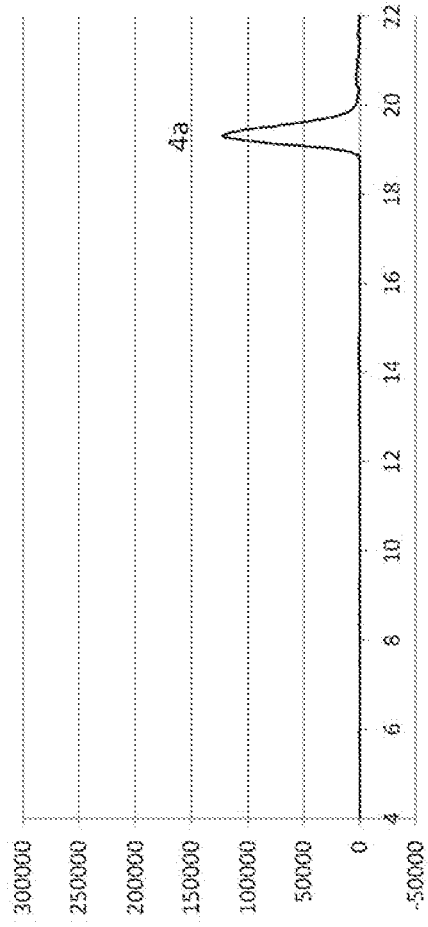
FIG. 10: Extracted ion chromatograms for pSK68: PN2250 (paxG, nodC, nodM, nodB, and nodW:ΔPAX cluster) showing MS peaks for emindole SB 4*a* (19.3 min, 406.31±0.01 m/z) and NAF 5*a* (6.2 min, 436.284±0.01 m/z).
Figure 10:
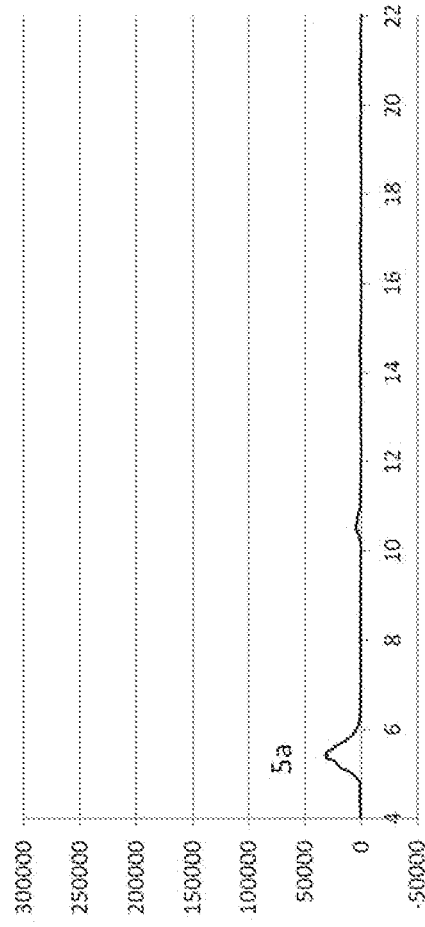

Since the identification of the biosynthetic pathway for the IDT paxilline $6b^{6,13-16}$ in *Penicillium paxilli*, gene functionality in seven other IDT biosynthetic pathways has been elucidated.[7-22] These IDT pathways share homologous genes that encode enzymes for the first three steps in IDT biosynthesis (FIG. 2): (I) a geranylgeranyl pyrophosphate synthase (GGPPS), converts farnesyl pyrophosphate and isopentyl pyrophosphate into GGPP 1a, (II) a geranylgeranyl transferase (GGT), catalyzes the indole condensation of GGPP 1a and indole-3-glycerol phosphate 1b to make GGI 2, and (III) a regioselective flavin adenine dinucleotide (FAD) dependent epoxidase, creates the single and/or double epoxidized-GGI products 3a/3b. At the fourth enzymatic step, involving IDT cyclization, the pathways diverge into four key branches giving rise to mono/di-oxygenated anti-Markovnikov-derived cyclic cores like emindole SB 4a and paspaline 4b, or mono/di-oxygenated Markovnikov-derived cyclic cores like aflavinine 4c and the emindole DB 4d. These cyclic cores are often further modified with decorative enzymes that create the bioactive diversity seen across IDTs.

NAs are bioactive IDTs produced by *Hypoxylon pulicicidum*, with NAA 10 being of particular significance due to its highly potent insecticidal activity against blood-feeding arthropods and lack of mammalian toxicity.[5,8] However, as described herein, the production of NAA 10 by direct synthesis has not been achieved, and the biosynthetic production of this compound in quantities that would be useful at even a small scale commercial level would be difficult to achieve, if at all.

Accordingly, the present invention generally relates to a series of isolated genes from the fungus, *H. pulicicidum*, which combined, form a gene cluster that mediates the production of NAs, and to the use of that gene cluster to direct the heterologous expression of NAs in an isolated host cell, preferably an isolated fungal cell. Using a recently developed technique for manipulating gene sequences termed the Modular Idempotent DNA Assembly System (MIDAS), the inventors have reconstituted the biosynthetic pathway for NAF 5*a* from *H. pulicicidum* in an alternate fungal host, *Penicillium paxilli*. The MIDAS platform and method of using the MIDAS platform are described herein, and related patent application AU2017903955, the entirety of which is incorporated herein by reference.

The inventors analyzed the genomic sequence of *H. pulicicidum* and identified a cluster comprising 15 predicted coding sequences (CDSs): nodW cDNA (SEQ ID NO:2) and genomic DNA (SEQ ID NO:1), nodR cDNA (SEQ ID NO:5) and genomic DNA (SEQ ID NO:4), nodX cDNA (SEQ ID NO:8) and genomic DNA (SEQ ID NO:7), nodM cDNA (SEQ ID NO:11) and genomic DNA (SEQ ID NO:10), nodB cDNA (SEQ ID NO:14) and genomic DNA (SEQ ID NO:13), nodO cDNA (SEQ ID NO:17) and genomic DNA (SEQ ID NO:16), nodJ cDNA (SEQ ID NO:20) and genomic DNA (SEQ ID NO:19), nodC cDNA (SEQ ID NO:23) and genomic DNA (SEQ ID NO:22), nodY1 cDNA (SEQ ID NO:26) and genomic DNA (SEQ ID NO:25), nodD2 cDNA (SEQ ID NO:29) and genomic DNA (SEQ ID NO:28), nodD1 cDNA (SEQ ID NO:32) and genomic DNA (SEQ ID NO:31), nodY2 cDNA (SEQ ID NO:35) and genomic DNA (SEQ ID NO:34), nodZ cDNA (SEQ ID NO:38) and genomic DNA (SEQ ID NO:37), nodS cDNA (SEQ ID NO:49) and genomic DNA (SEQ ID NO:48), nodI cDNA (SEQ ID NO:55) and genomic DNA (SEQ ID NO:54) that are expected to encode enzymes necessary for the biosynthesis of NAA 10.

The boundaries of this cluster were determined by identifying flanking genes that have high similarity and syntenic organisation compared with an equivalent genomic locus in another *Hypoxylon* strain that does not produce nodulisporic acids. Details of these predicted genes in the cluster and their proposed function are shown in Table 1. Seven of the cluster genes are homologous to those found in other IDT biosynthetic gene clusters (Tables 2-6). The protein product of the seven predicted genes that are homologous to IDT biosynthesis genes from other fungi have at least 35% amino acid identity to their homologues in the PAX cluster of *P. paxilli*, the JAN cluster of *P. janthinellum*, and/or the PEN cluster of *P. crustosum* and include a GGT (NodC (SEQ ID NO:24)), two FAD-dependent oxidases (NodM (SEQ ID NO:12) and NodO (SEQ ID NO:18)), an IDT cyclase (NodB (SEQ ID NO:15)), two prenyl transferases (NodD2 (SEQ ID NO:30), and NodD1 (SEQ ID NO:33)), and one cytochrome P450 oxygenase (NodR (SEQ ID NO:6)). The other seven putative ORFs were predicted to encode four cytochrome P450 oxygenases (NodW (SEQ ID NO:3), NodX (SEQ ID NO:9), NodJ (SEQ ID NO:21), and NodZ (SEQ ID NO:39)), a pair of paralogous FAD-dependent oxygenases (NodY1 (SEQ ID NO:27), and NodY2 (SEQ ID NO:36)), and two gene products that may be involved in NA biosynthesis with unknown functions (NodS (SEQ ID NO:50), and NodI (SEQ ID NO:56)). Similar to the TER gene cluster from *Chaunopycnis alba* (*Tolypodadium album*) responsible for terpendole biosynthesis,[17] the NOD cluster does not appear to contain a secondary metabolite-specific GGPPS gene. Notably, the inventors identified only one GGPPS-encoding gene in the genome of *H. pulicicidum* and the amino acid sequence of its predicted protein product, its exon/intron structure, and its location outside of the identified cluster strongly suggest that it is responsible for primary metabolic function similar to ggs1 in *P. paxilli*.[3]

To confirm the function of gene products and directly establish their respective roles in NAA 10 biosynthesis the inventors constructed a series of plasmids harbouring various combinations of these genes, which they then transformed into in appropriate *P. paxilli* hosts (Table 7) for heterologous production of NAA 10 precursors. Accordingly, CDSs of the *H. pulicicidum* genes of interest were amplified (see Table 8 for primers) and cloned into a MIDAS Level-1 destination vector, pML1 (Table 9). At MIDAS Level-2, the cloned CDSs were placed under the control of heterologous promoter (ProUTR) and transcriptional terminator (UTRterm) modules to generate full-length TUs (Table 10), which were then used to generate the multi-gene plasmids (Table 11). The inventors used a repertoire of *P. paxilli* knockout strains (Table 7) to carry out functional complementations and pathway reconstitution to determine the functions of genes in the NOD cluster. Following transformation of *P. paxilli* hosts with multi-gene plasmids, the inventors determined the chemical phenotypes of the transformants initially by normal-phase thin-layer chromatography (TLC, results not shown) and subsequently by reversed-phase liquid chromatography-mass spectrometry (LC-MS) analysis of fungal extracts. The inventors purified the newly expressed metabolites, as determined by high resolution mass spectrometry (HRMS), by semi-preparative reversed-phase high-performance liquid chromatorgraphy (HPLC) and subjected compounds to nuclear magnetic resonance (NMR) spectorscopic analysis ($^1$H, $^{13}$C, and HSQC, HMBC, COSY) for final identification.

Using this methodology, the inventors identified that nodC (cDNA (SEQ ID NO:23) and genomic DNA (SEQ ID NO:22)) is a functional ortholog of paxC (cDNA (SEQ ID NO:43) and genomic DNA (SEQ ID NO:42)), and that NodC (SEQ ID NO:24) mediates the production of GGI 2, the second step in IDT biosynthesis, in *H. pulicicidum* (FIG. 3, trace i.b, FIG. 4). NodC (SEQ ID NO:24) shares 52.3% amino acid sequence identity with PaxC (SEQ ID NO:44) from *P. paxilli* (Table 2). The inventors also identified that nodM (cDNA (SEQ ID NO:11) and genomic DNA (SEQ ID NO:10)), is a homolog of paxM (cDNA (SEQ ID NO:46) and genomic DNA (SEQ ID NO:45)), and that NodM (SEQ ID NO:12) is a GGI 2 mono-epoxidase that catalyzes the production of monoepoxidized-GGI 3*a* (FIG. 3, trace ii.b, FIG. 5). NodM (SEQ ID NO:12) shares 48.6% sequence identity with PaxM (SEQ ID NO:47) from *P. paxilli* (Table 3). Notably, the inventors showed that NodM (SEQ ID NO:12) is specifically a mono-epoxidase, unlike PaxM (SEQ ID NO:47), which is a mono- or di-epoxidase. The inventors further confirmed that NodB (SEQ ID NO:15) from *H. pulicicidum* acts as the IDT cyclase that cyclizes the monoepoxidized-GGI product 3*a* to form emindole SB 4*a* (FIG. 3, trace iii.b, FIG. 6) and that nodB (cDNA (SEQ ID NO:14) and genomic DNA (SEQ ID NO:13)) is a functional ortholog of paxB (cDNA (SEQ ID NO:52) and genomic DNA (SEQ ID NO:51)) from *P. paxilli* (FIG. 3, trace iv.b, FIG. 7). NodB (SEQ ID NO:15) from *H. pulicicidum* shares 63% identity with PaxB (SEQ ID NO:53) from *P. paxilli* (Table 4).

The dedicated NAA 10 core is NAF 5*a*, generated by oxidation of the terminal methyl carbon, C5", of emindole SB 4*a* (FIG. 8B). Accordingly the inventors confirmed the identity of this oxidase as a P450 oxygenase encoded by *H. pulicicidum* nodW (cDNA (SEQ ID NO:2) and genomic DNA (SEQ ID NO:1)) by co-expression of nodW (cDNA (SEQ ID NO:2) and genomic DNA (SEQ ID NO:1)) with nodM (cDNA (SEQ ID NO:11) and genomic DNA (SEQ ID NO:10)) into a paxM (cDNA (SEQ ID NO:46) and genomic DNA (SEQ ID NO:45)) deletion background (PN2257) resulting in the production of NAF 5*a* (FIG. 3, trace v.b, FIG. 9).

To confirm that only five genes are essential for the production of NAF 5*a* in *P. paxilli*, and to establish that no other *P. paxilli* IDT genes from the PAX cluster in the paxM KO strain (PN2257) were contributing to NAF 5*a* production, the inventors assembled a multigene construct comprising paxG (genomic DNA (SEQ ID NO:40)) from *P. paxilli*, and nodC (genomic DNA (SEQ ID NO:22)), nodM (genomic DNA (SEQ ID NO:10)), nodB (genomic DNA (SEQ ID NO:13)), and nodW (genomic DNA (SEQ ID NO:1)) from *H. pulicicidum*. This multigene construct was transformed into a *P. paxilli* PAX gene cluster knockout strain (PN2250). As expected, expression of the five genes showed that NAF 5*a* was produced (FIG. 10) and indicated that these five genes are indeed required to biosynthesize NAF 5*a*.

Based on the work described herein the inventors disclose the use of heterologous expression to identify the first five steps that deliver the NAA 10 core compound, NAF 5*a*. In particular, the inventors have confirmed the function of four previously unknown genes from *H. pulicicidum*: nodC (cDNA (SEQ ID NO:23) and genomic DNA (SEQ ID NO:22)), nodM (cDNA (SEQ ID NO:11) and genomic DNA (SEQ ID NO:10)), nodB (cDNA (SEQ ID NO:14) and genomic DNA (SEQ ID NO:13)), and nodW (cDNA (SEQ ID NO:2) and genomic DNA (SEQ ID NO:1)), and discovered a second filamentous fungal species, *H. pulicicidum*, that does not appear to have a secondary metabolic GGPPS gene but can still produce IDTs. Without wishing to be bound by theory, the inventors believe that *H. pulicicidum* relies upon its primary metabolic GGPPSs to provide the GGPP for IDT synthesis. The lack of a secondary-metabolic GGPPS may explain why *H. pulicicidum* produces such low quantities of NAs. The low quantities of NAs produced by *H. pulicicidum* is a challenge for both resolving the biosynthetic details and for usage of the compounds or their derivatives. Using the efficient gene reassembly of MIDAS and heterologous expression in *P. paxilli* the inventors have overcome both these issues. Furthermore, the inventors demonstrated that *P. paxilli*, with its far more favourable growth conditions, is a suitable host for heterologous expression studies, which enabled the inventors to confirm the function of genes more quickly and easily than would have been possible had they relied on the biosynthetic machinery of *H. pulicicidum.*

Elucidation of the biosynthetic mutes for heterologous production of NAF 5a in *P. paxilli* provides a reasonable expectation of success in being able to fully identify the gene products from *H. pulicicidum* that are responsible for the 'decoration' steps that lead to the production of fully functionalized NAA 10. This reasonable expectation comes from the identification, by the inventors, of the nucleic acid CDSs that are predicted to encode the enzymes required for prenylation to form nodulisporic acid E 6*a*, and for oxidations, to form nodulisporic acid D 7*a*. Each of these nucleic acid sequences has been putatively identified from the *H. pulicicidum* biosynthetic gene cluster described herein. Overall, the inventors work described herein confirms that heterologous expression of IDT genes in a heterologous host is a viable method that can be employed to produce natural products that are difficult to obtain in other ways, and that could be useful across many industries.

Polypeptides

Accordingly, in one aspect the invention relates to an isolated polypeptide comprising an amino acid sequence selected from the group consisting of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

Preferably the functional variant or fragment thereof comprises at least 70%, preferably at least 75%, preferably at least 80%, preferably at least 85%, preferably at least 90%, preferably at least 95%, preferably at least 99% amino acid sequence identity to an amino acid sequence selected from the group consisting of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56).

Preferably the isolated polypeptide comprising NodW (SEQ ID NO:3) or a functional variant or fragment thereof has oxygenase activity, preferably cytochrome P450 oxygenase activity.

Preferably the isolated polypeptide comprising NodR (SEQ ID NO:6) or a functional variant or fragment thereof has oxygenase activity, preferably cytochrome P450 oxygenase activity.

Preferably the isolated polypeptide comprising NodX (SEQ ID NO:9) or a functional variant or fragment thereof has oxygenase activity, preferably cytochrome P450 oxygenase activity.

Preferably the isolated polypeptide comprising NodM (SEQ ID NO:12) or a functional variant or fragment thereof has oxygenase activity, preferably FAD-dependent oxygenase activity.

Preferably the isolated polypeptide comprising NodB (SEQ ID NO:15) or a functional variant or fragment thereof has cyclase activity, preferably IDT cyclase activity.

Preferably the isolated polypeptide comprising NodO (SEQ ID NO:18) or a functional variant or fragment thereof has oxygenase activity, preferably FAD-dependent oxygenase activity.

Preferably the isolated polypeptide comprising NodJ (SEQ ID NO:21) or a functional variant or fragment thereof has oxygenase activity, preferably cytochrome P450 oxygenase activity.

Preferably the isolated polypeptide comprising NodC (SEQ ID NO:24) or a functional variant or fragment thereof has transferase activity, preferably GGT activity.

Preferably the isolated polypeptide comprising NodY1 (SEQ ID NO:27) or a functional variant or fragment thereof has oxygenase activity, preferably FAD-dependent oxygenase activity.

Preferably the isolated polypeptide comprising NodD2 (SEQ ID NO:30) or a functional variant or fragment thereof has transferase activity, preferably prenyl transferase activity.

Preferably the isolated polypeptide comprising NodD1 (SEQ ID NO:33) or a functional variant or fragment thereof has transferase activity, preferably prenyl transferase activity.

Preferably the isolated polypeptide comprising NodY2 (SEQ ID NO:36) or a functional variant or fragment thereof has oxygenase activity, preferably FAD-dependent oxygenase activity.

Preferably the isolated polypeptide comprising NodZ (SEQ ID NO:39) or a functional variant or fragment thereof has oxygenase activity, preferably cytochrome P450 oxygenase activity.

In one embodiment the isolated polypeptide comprises SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In one embodiment the isolated polypeptide consists essentially of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In one embodiment the isolated polypeptide consists of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

Polynucleotides

In another aspect the invention relates to an isolated polynucleotide encoding a polypeptide comprising an amino acid sequence selected from the group consisting of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

Preferably the functional variant or fragment thereof comprises at least 70%, preferably at least 75%, preferably at least 80%, preferably at least 85%, preferably at least 90%, preferably at least 95%, preferably at least 99% amino acid sequence identity to an amino acid sequence selected from the group consisting of SEQ ID NO: NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) a functional variant or fragment thereof.

Preferably the isolated polynucleotide encodes a polypeptide comprising NodW (SEQ ID NO:3) or a functional variant or fragment thereof having oxygenase activity, preferably cytochrome P450 oxygenase activity.

Preferably the isolated polynucleotide encodes a polypeptide comprising NodR (SEQ ID NO:6) or a functional variant or fragment thereof having oxygenase activity, preferably cytochrome P450 oxygenase activity.

Preferably the isolated polynucleotide encodes a polypeptide comprising NodX (SEQ ID NO:9) or a functional variant or fragment thereof having oxygenase activity, preferably cytochrome P450 oxygenase activity.

Preferably the isolated polynucleotide encodes a polypeptide comprising NodM (SEQ ID NO:12) or a functional variant or fragment thereof having oxygenase activity, preferably FAD-dependent oxygenase activity.

Preferably the isolated polynucleotide encodes a polypeptide comprising NodB (SEQ ID NO:15) or a functional variant or fragment thereof having cyclase activity, preferably IDT cyclase activity.

Preferably the isolated polynucleotide encodes a polypeptide comprising NodO (SEQ ID NO:18) or a functional variant or fragment thereof having oxygenase activity, preferably FAD-dependent oxygenase activity.

Preferably the isolated polynucleotide encodes a polypeptide comprising NodJ (SEQ ID NO:21) or a functional variant or fragment thereof having oxygenase activity, preferably cytochrome P450 oxygenase activity.

Preferably the isolated polynucleotide encodes a polypeptide comprising NodC (SEQ ID NO:24) or a functional variant or fragment thereof having transferase activity, preferably GGT activity.

Preferably the isolated polynucleotide encodes a polypeptide comprising NodY1 (SEQ ID NO:27) or a functional variant or fragment thereof having oxygenase activity, preferably FAD-dependent oxygenase activity.

Preferably the isolated polynucleotide encodes a polypeptide comprising NodD2 (SEQ ID NO:30) or a functional variant or fragment thereof having transferase activity, preferably prenyl transferase activity.

Preferably the isolated polynucleotide encodes a polypeptide comprising NodD1 (SEQ ID NO:33) or a functional variant or fragment thereof having transferase activity, preferably prenyl transferase activity.

Preferably the isolated polynucleotide encodes a polypeptide comprising NodY2 (SEQ ID NO:36) or a functional variant or fragment thereof having oxygenase activity, preferably FAD-dependent oxygenase activity.

Preferably the isolated polynucleotide encodes a polypeptide comprising NodZ (SEQ ID NO:39) or a functional variant or fragment thereof having oxygenase activity, preferably cytochrome P450 oxygenase activity.

In one embodiment the isolated polynucleotide encodes a polypeptide comprising NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In one embodiment the isolated polynucleotide encodes a polypeptide consisting essentially of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In one embodiment the isolated polynucleotide encodes a polypeptide consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof.

In another aspect the invention relates to an isolated polynucleotide comprising at least 70% nucleic acid sequence identity to a nucleic acid sequence selected from the group consisting of nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO: 13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

Preferably the isolated polynucleotide comprises at least 75%, preferably at least 80%, preferably at least 85%, preferably at least 90%, preferably at least 95%, preferably at least 99% nucleic acid sequence identity to a nucleic acid sequence selected from the group consisting of SEQ ID NO: nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO:13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

In one embodiment the isolated polynucleotide comprises a nucleic acid sequence selected from the group consisting of nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO:13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

In one embodiment the isolated polynucleotide consists essentially of a nucleic acid sequence selected from the group consisting of nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO:13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

In one embodiment the isolated polynucleotide consists of a nucleic acid sequence selected from the group consisting of nodW cDNA (SEQ ID NO:2), nodW genomic DNA (SEQ ID NO:1), nodR cDNA (SEQ ID NO:5), nodR genomic DNA (SEQ ID NO:4), nodX cDNA (SEQ ID NO:8), nodX genomic DNA (SEQ ID NO:7), nodM cDNA (SEQ ID NO:11), nodM genomic DNA (SEQ ID NO:10), nodB cDNA (SEQ ID NO:14), nodB genomic DNA (SEQ ID NO:13), nodO cDNA (SEQ ID NO:17), nodO genomic DNA (SEQ ID NO:16), nodJ cDNA (SEQ ID NO:20), nodJ genomic DNA (SEQ ID NO:19), nodC cDNA (SEQ ID NO:23), nodC genomic DNA (SEQ ID NO:22), nodY1 cDNA (SEQ ID NO:26), nodY1genomic DNA (SEQ ID NO:25), nodD2 cDNA (SEQ ID NO:29), nodD2 genomic DNA (SEQ ID NO:28), nodD1 cDNA (SEQ ID NO:32), nodD1 genomic DNA (SEQ ID NO:31), nodY2 cDNA (SEQ ID NO:35), nodY2 genomic DNA (SEQ ID NO:34), nodZ cDNA (SEQ ID NO:38), nodZ genomic DNA (SEQ ID NO:37), nodS cDNA (SEQ ID NO:49), nodS genomic DNA (SEQ ID NO:48), nodI cDNA (SEQ ID NO:55), and nodI genomic DNA (SEQ ID NO:54).

The nucleic acid molecules of the invention or otherwise described herein are preferably isolated. They can be isolated from a biological sample using a variety of techniques known to those of ordinary skill in the art. By way of example, such polynucleotides can be isolated through use of the polymerase chain reaction (PCR) as known in the art. The nucleic acid molecules of the invention can be amplified using primers, as defined herein, derived from the polynucleotide sequences of the invention.

Further methods for isolating polynucleotides include use of all, or portions of, a polynucleotide of the invention as hybridization probes. The technique of hybridizing labeled polynucleotide probes to polynucleotides immobilized on solid supports such as nitrocellulose filters or nylon membranes, can be used to screen genomic or cDNA libraries. Similarly, probes may be coupled to beads and hybridized to the target sequence. Isolation can be effected using known art protocols such as magnetic separation. The choice of appropriately stringent hybridization and wash conditions is believed to be within the skill of those in the art.

Polynucleotide fragments may be produced by techniques well-known in the art such as restriction endonuclease digestion and oligonucleotide synthesis.

A partial polynucleotide sequence may be used as a probe, in methods well-known in the art to identify the corresponding full length polynucleotide sequence in a sample. Such methods include PCR-based methods, 5'RACE and hybridization-based method, computer/database-based methods as known in the art. Detectable labels such as radioisotopes, fluorescent, chemiluminescent and bioluminescent labels may be used to facilitate detection. Inverse PCR also permits acquisition of unknown sequences, flanking the polynucleotide sequences disclosed herein, starting with primers based on a known region as known and used in the art. The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized as known in the art. Primers and primer pairs which allow amplification of polynucleotides of the invention, also form a further aspect of this invention.

Variants (including orthologues) may be identified by the methods described. Variant polynucleotides may be identified using PCR-based methods as known in the art.

Typically, the polynucleotide sequence of a primer, useful to amplify variants of polynucleotide molecules by PCR, may be based on a sequence encoding a conserved region of the corresponding amino acid sequence.

Further methods for identifying variant polynucleotides include use of all, or portions of the specified polynucleotides as hybridization probes to screen genomic or cDNA libraries as described above. Typically probes based on a sequence encoding a conserved region of the corresponding amino acid sequence may be used. Hybridization conditions may also be less stringent than those used when screening for sequences identical to the probe.

In another aspect the invention relates to a TU comprising at least one isolated polynucleotide as described herein. In one embodiment the TU is comprised in vector, preferably an expression vector. In one embodiment the vector is selected from the group consisting of plasmids, BACs, (PACs), YACs, bacteriophage, phagemids, and cosmids. Preferably the vector is a plasmid.

In another aspect the invention relates to a vector that encodes an isolated polypeptide or functional variant or fragment thereof according to the invention.

In another aspect the invention relates to a vector comprising an isolated nucleic acid sequence according to the invention.

In one embodiment the isolated nucleic acid sequence is comprised in a TU.

In one embodiment the vector is selected from the group consisting of plasmids, BACs, PACs, YACs, bacteriophage, phagemids, and cosmids. Preferably the vector is a plasmid. In one embodiment the vector is an expression vector.

A TU comprising a polynucleotide of the invention can be incorporated into any suitable vector capable of expressing that polynucleotide or, where applicable, an encoded polypeptide of the invention in vitro or in a host cell. Preferably the vector is an expression vector. Examples of suitable expression vectors include, but not limited to, plasmid DNA vectors, viral DNA vectors (such as adenovirus and adeno-associated virus), or viral RNA vectors (such as a retroviral vectors). In some embodiments the plasmid and/or phage vectors may be selected from the following vectors or variants thereof including pUC18, pU19, Mp18, Mp19, ColE1, PCR1 and pKRC; lambda gt10 and M13 plasmids such as pBR322, pACYC184, pT127, RP4, p1J101, SV40 and BPV. Also included are vectors such as, but not limited to, cosmids, YACS, BACs shuttle vectors such as pSA3, PAT28 transposons (such as described in U.S. Pat. No. 5,792,294) and the like.

Suitable viral vectors include, but are not limited to vectors derived from adenovirus (AV); adeno-associated virus (AAV); retroviruses (e.g., lentiviruses (LV), Rhabdoviruses, murine leukemia virus); herpes virus, and the like. Viral vectors employed herein can be appropriately modified by pseudotyping with envelope proteins or other surface antigens from other viruses, or by substituting different viral capsid proteins, as known and used in the art.

In one embodiment the expression vector comprises at least one, preferably at least two, preferably at least three, preferably at least four, preferably at least five, preferably at least six, preferably at least seven, preferably at least eight, preferably at least nine, preferably at least 10 isolated polynucleotides as described herein.

In one embodiment the expression vector comprises at least one, preferably at least two, preferably at least three, preferably at least four, preferably at least five, preferably at least six, preferably at least seven, preferably at least eight, preferably at least nine, preferably at least 10 TUs as described herein.

In one embodiment the vector is a component in a cloning system. In one embodiment the cloning system is useful for making a gene construct comprising at least one TU.

In one embodiment the vector is comprised in a vector set, the vector set being part of a cloning system. In one embodiment the cloning system is useful for making a gene construct comprising at least one TU.

In one embodiment the cloning system is useful for making a gene construct comprising at least one TU.

In one embodiment the gene construct is a multigene construct comprising at least two TUs. In one embodiment the multigene construct comprises at least three, preferably at least four, preferably at least five, preferably at least six, preferably at least seven, preferably at least eight, preferably at least nine, preferably at least ten TUs.

The TUs described herein may comprise one or more of the disclosed polynucleotide sequences and/or polynucleotides encoding the disclosed polypeptides, of the invention.

The TU can constructed to drive expression of at least one polypeptide involved in the biosynthesis of NAA10, either in vitro or in vivo. In one embodiment, the TU comprises a polynucleotide of the invention operatively linked to 5' or 3' untranslated regulatory sequences. The design of a particular TU will depend on various factors including the host cells in which the operatively linked polynucleotide is to be expressed and the desired level of polynucleotide expression.

Likewise, the selection of various promoters, enhancers and/or other genetic elements for a TU will depend on various factors including the host cells and expression levels discussed above. In one embodiment, the TU comprises a homologous promoter operatively linked to a polynucleotide of the invention. In another embodiment, the expression cassette comprises a heterologous promoter operatively linked to a polynucleotide of the invention. In one embodiment, the homologous or heterologous promoter is an inducible, repressible or regulatable promoter. A suitable promoter may be chosen and used under the appropriate conditions to direct high-level expression of a polynucleotide of the invention. Many such elements are described in the literature and are available through commercial suppliers.

By way of example only, promoters useful in the expression cassettes can be any suitable eukaryotic or prokaryotic promoter. In one embodiment, the eukaryotic promoter can be a eukaryotic RNA polymerase I (pol I), RNA polymerase II (pol II), or RNA polymerase III (pol III). Expression levels of an operably linked polynucleotide in a particular cell type will be determined by the nearby presence (or absence) of specific gene regulatory sequences (e.g., enhancers, silencers and the like). Any suitable promoter/enhancer combination (see: Eukaryotic Promoter Data Base EPDB) can be used to drive expression of a polynucleotide of the invention.

Additional promoters useful in expression cassettes include β-lactamase, alkaline phosphatase, tryptophan, and tac promoter systems which are all well known in the art. Yeast promoters include 3-phosphoglycerate kinase, enolase, hexokinase, pyruvate decarboxylase, glucokinase, and glyceraldehydrate-3-phosphanate dehydrogenase but are not limited thereto.

Prokaryotic promoters useful in expression cassettes include constitutive promoters as known in the art (such as the int promoter of bacteriophage lamda and the bla promoter of the beta-lactamase gene sequence of pBR322) and regulatable promoters (such as lacZ, recA and gal). A ribosome binding site upstream of the CDS may also be required for expression.

Enhancers useful in a TU include SV40 enhancer, cytomegalovirus early promoter enhancer, globin, albumin, insulin and the like.

In one embodiment, a TU may be driven by a T3, T7 or SP6 cytoplasmic expression system.

The choice of a particular promoter/enhancer/cell type combination for protein expression is within the ordinary skill of those in the art of molecular biology (see, for example, Sambrook et al. (1989) which is incorporated herein by reference).

In another aspect the invention relates to an isolated host cell comprising an isolated polypeptide, isolated polynucleotide, TU and/or isolated vector according to the invention.

In one embodiment the isolated host cell is a prokaryotic or eukaryotic cell. Prokaryotes most commonly employed as host cells are strains of *Escherichia coli* (*E. coli*). Other prokaryotic hosts include *Pseudomonas, Bacillus, Serratia,*

*Klebsiella, Streptomyces, Listeria, Salmonella* and Mycobacteria but are not limited thereto.

In one embodiment the eukaryotic cell is an animal cell, a plant cell, a fungal cell or a protist cell. In one embodiment the animal cell is an insect cell or a mammalian cell. In one embodiment the fungal cell is a single cell of a unicellular fungal host strain. In one embodiment the fungal cell comprises fungal hyphae or the mycelia of a fungal host strain.

In one embodiment the fungal cell, hyphae or mycelia of the fungal host strain are from the genus *Aspergillus, Trichoderma, Neurospora, Fusarium, Mortierella, Chrysosporium, Candida, Geotrichum, Yarrowia, Eremothecium, Trichoplusia, Ashbya, Hansenula, Pichia, Kluveromyces, Schizzosaccharomyces, Monascus, Talaromyces, Cryptonectria, Endothia, Tolypocladium, Hypocrea, Gibberella, Acremonium, Agaricus, Pleurotus, Penicillium, Volvariella, Flammulina, Lentinula, Auricularia, Ganoderma,* (*Rhizo*)*mucor, Riopus*, or *Saccharomyces*, preferably *Penicillium, Aspergillus, Saccharomyces, Pichia, Tricoplusia*, and *Spondoptera*. Preferably the fungal cell is from *Saccharomyces*. Preferably the fungal hyphae or mycelia is from *Penicillium*, preferably *P. paxilli*.

In another aspect the invention relates to a method of making at least one NA comprising heterologously expressing at least one polypeptide, isolated nucleic acid sequence, TU or vector according to the invention in an isolated host cell.

In one embodiment the NA is selected from the group of NAs depicted in FIG. 1. Preferably the NA is NAF 5*a* or NAA 10, preferably NAA 10.

In one embodiment the polypeptide is a polypeptide or functional variant or fragment according to the invention.

Specifically contemplated as embodiments within this aspect of the invention are various embodiments set out herein with regards to any other aspect of the invention that relate to heterologous expression (including choice of appropriate regulatory sequences), expression cassettes, genetic elements, TUs, multigene constructs, host cells, and vectors.

In a particular embodiment, heterologous expression of the polypeptide comprises expression of at least one polynucleotide according to the invention or at least one TU encoding at least one polypeptide of the invention, from at least one vector as described herein in an isolated fungal host cell or in the mycelia of an isolated fungal strain as described herein. In one embodiment the polypeptide is NodR (SEQ ID NO:6) NodX (SEQ ID NO:9), or NodZ (SEQ ID NO:39), preferably the polypeptide is an enzyme that catalyzes a biological transformation from NAB 9 to NAA 10. In one embodiment the fungal cell or strain is a cell or strain of *Penicillium*, preferably *P. paxilli*.

In one embodiment the TU is comprised in a multigene construct comprising at least two, at least three, at least four, at least five, at least six, at least seven, at least eight, at least nine and/or at least 10 polynucleotides encoding polypeptides according to the invention.

In another aspect the invention relates to at least one NA made by a method of the invention. In one embodiment the NA is selected from the group of NAs depicted in FIG. 1. Preferably the NA is NAF 5*a* or NAA 10, preferably NAA 10.

In another aspect the present invention relates to an isolated polypeptide or functional variant or fragment thereof from *Hypoxylon* spp. that catalyzes a biochemical reaction in the biosynthetic pathway leading from GGI 2 to NAA 10.

In another aspect the present invention relates to an isolated polynucleotide encoding at least one polypeptide from *Hypoxylon* spp. that catalyzes a biochemical reaction in the biosynthetic pathway leading from GGI 2 to NAA 10.

In one embodiment the isolated polypeptide is an oxygenase, preferably a cytochrome P450 oxygenase or a FAD-dependent oxygenase. Preferably the cytochrome P450 oxygenase is NodW (SEQ ID NO:3), NodR (SEQ ID NO:6), NodX (SEQ ID NO:9), NodJ (SEQ ID NO:21), or NodZ (SEQ ID NO:39). Preferably the FAD dependent oxygenase is NodM (SEQ ID NO:12), NodO (SEQ ID NO:18), NodY1 (SEQ ID NO:27), or NodY2 (SEQ ID NO:36). In one embodiment the isolated polypeptide is a transferase, preferably a GGT, or a prenyl transferase. Preferably the GGT is NodC (SEQ ID NO:24). Preferably the prenyl transferases are NodD1 (SEQ ID NO:33), or NodD2 (SEQ ID NO:30). In one embodiment the isolated polypeptide is a IDT cyclase. Preferably the IDT cyclase is NodB (SEQ ID NO:15). In one embodiment the isolated polypeptide is NodS (SEQ ID NO:50). In one embodiment the isolated polypeptide is NodI (SEQ ID NO:56).

In one embodiment the isolated polypeptide catalyzes a biochemical reaction in the biosynthetic pathway leading from GGI 2 to NAF 5*a*. Preferably the isolated polypeptide is a GGT, a FAD-dependent oxygenase, an IDT cyclase, or a cytochrome P450 oxygenase.

Preferably the GGT is NodC (SEQ ID NO:24). Preferably the FAD-dependent oxygenase is NodM (SEQ ID NO:12). Preferably the IDT cyclase is NodB (SEQ ID NO:15). Preferably the cytochrome P450 oxygenase is NodW (SEQ ID NO:3).

In one embodiment the isolated polypeptide or functional variant or fragment thereof is encoded by a nucleic acid according to the invention.

In another aspect the invention relates to a method of making at least one *Hypoxylon* spp. polypeptide or functional variant or fragment thereof comprising heterologously expressing an isolated nucleic acid sequence, TU or vector according to the invention in an isolated host cell.

In one embodiment the at least one *Hypoxylon* spp. polypeptide is a polypeptide according to the invention as contemplated herein for any other aspect of the invention.

In one embodiment the at least one *Hypoxylon* spp. polypeptide is a polypeptide comprising an amino acid sequence of SEQ ID NO: NodW (SEQ ID NO:3) or a functional variant or fragment thereof. Preferably the polypeptide consists essentially or consists of SEQ ID NO: NodW (SEQ ID NO:3). In one embodiment the isolated host cell comprises fungal mycelia of the genus *Penicillium*, preferably *P. paxilli*.

Specifically contemplated for this aspect of the invention are various embodiments set out for any other aspect of the invention that relate to the heterologous expression (including choice of appropriate regulatory sequences), genetic elements, TUs, multigene constructs, host cells, and vectors.

In another aspect the invention relates to a method of making at least one NA comprising heterologously expressing in an isolated host cell, at least one polypeptide that catalyzes a biochemical reaction in the biosynthetic pathway leading from GGI 2 to NAA 10.

In one embodiment the at least one polypeptide is an oxygenase, preferably a cytochrome P450 oxygenase or a FAD-dependent oxygenase. Preferably the cytochrome P450 oxygenase is NodW (SEQ ID NO:3), NodR (SEQ ID NO:6), NodX (SEQ ID NO:9), NodJ (SEQ ID NO:21), or NodZ (SEQ ID NO:39). Preferably the FAD dependent oxygenase is NodM (SEQ ID NO:12), NodO (SEQ ID NO:18), NodY1 (SEQ ID NO:27), or NodY2 (SEQ ID NO:36). In one embodiment the isolated polypeptide is a transferase, preferably a GGT, or a prenyl transferase. Preferably the GGT is NodC (SEQ ID NO:24). Preferably the prenyl transferases are NodD1 (SEQ ID NO:33), or NodD2 (SEQ ID NO:30). In one embodiment the isolated polypeptide is a IDT cyclase. Preferably the IDT cyclase is NodB (SEQ ID NO:15). In one embodiment the isolated polypeptide is NodS (SEQ ID NO:50). In one embodiment the isolated polypeptide is NodI (SEQ ID NO:56).

In one embodiment the at least one polypeptide catalyzes a biochemical reaction in the biosynthetic pathway leading from GGI 2 to NAF 5a. Preferably at least one polypeptide is a GGT, a FAD-dependent oxygenase, an IDT cyclase, or a cytochrome P450 oxygenase. Preferably the GGT is NodC (SEQ ID NO:24). Preferably the FAD-dependent oxygenase is NodM (SEQ ID NO:12). Preferably the IDT cyclase is NodB (SEQ ID NO:15). Preferably the cytochrome P450 oxygenase is NodW (SEQ ID NO:3).

In one embodiment the least one polypeptide comprises the amino acid sequence of SEQ ID NO: NodW (SEQ ID NO:3) or a functional variant or fragment thereof. Preferably the polypeptide consists essentially or consists of SEQ ID NO: NodW (SEQ ID NO:3). In one embodiment the isolated host cell comprises fungal mycelia of the genus *Penicillium*, preferably *P. paxilli*.

Specifically contemplated for this aspect of the invention are various embodiments set out for any other aspect of the invention that relate to the heterologous expression (including choice of appropriate regulatory sequences), genetic elements, TUs, multigene constructs, host cells, and vectors.

In another aspect the invention relates to an isolated host cell that expresses at least one heterologous polypeptide that catalyzes the transformation of a substrate in the biosynthetic pathway leading to the formation of NAA 10.

In one embodiment at least one heterologous polypeptide catalyzes the transformation of a substrate in the biosynthetic pathway leading to the formation of NAF 5a.

In one embodiment the substrate is selected from the group consisting of GGPP 1a, indole-3-glycerol phosphate 1b, GGI 2, mono-epoxidized GGI 3a, emindole SB 4a, NAF 5a, NAE 6a, NAD 7a, NAC 8, and NAB 9.

In one embodiment the transformation is selected from the group consisting of a condensation, an oxidation, or a cyclization.

In one embodiment the substrates that are transformed are GGPP 1a and indole-3-glycerol phosphate 1b, and the transformation is a condensation.

In one embodiment the substrate that is transformed is GGI 2 and the transformation is an oxidation.

In one embodiment the substrate that is transformed is mono-epoxidized GGI 3a and the transformation is a cyclization.

In one embodiment the substrate that is transformed is emindole SB 4a and the transformation is an oxidation.

In one embodiment the substrate that is transformed is NAF 5a and the transformation is a condensation.

In one embodiment the substrate that is transformed is NAE 6a and the transformation is an oxidation.

In one embodiment the substrate that is transformed is NAD 7a and the transformations are an oxidation and a condensation.

In one embodiment the substrate that is transformed is NAC 8 and the transformation is an oxidation.

In one embodiment the substrate that is transformed is NAB 9 and the transformation is an oxidation.

In another aspect the invention relates to an isolated host cell that produces, by heterologous expression, at least one polypeptide involved in the biosynthetic pathway leading to NAA 10.

In one embodiment the at least one polypeptide catalyzes a biochemical reaction in the biosynthetic pathway leading from GGI 2 to NAF 5a. Preferably at least one polypeptide is a GGT, a FAD-dependent oxygenase, an IDT cyclase, or a cytochrome P450 oxygenase. Preferably the GGT is NodC (SEQ ID NO:24). Preferably the FAD-dependent oxygenase is NodM (SEQ ID NO:12). Preferably the IDT cyclase is NodB (SEQ ID NO:15). Preferably the cytochrome P450 oxygenase is NodW (SEQ ID NO:3).

In some embodiments specifically contemplated for this aspect of the invention, the at least one polypeptide is a polypeptide involved in the biosynthetic pathway leading to NAA 10 as defined herein for any other aspect of the invention.

In one embodiment at least one polypeptide is a polypeptide or functional variant or fragment thereof of the invention. In one embodiment the polypeptide or functional variant or fragment thereof is encoded by a nucleic acid sequence of the invention.

In one embodiment the at least one polypeptide is involved in the biosynthetic pathway leading to NAF 5a. In one embodiment the least one polypeptide comprises the amino acid sequence of SEQ ID NO: NodW (SEQ ID NO:3) or a functional variant or fragment thereof. Preferably the polypeptide consists essentially or consists of SEQ ID NO: NodW (SEQ ID NO:3). In one embodiment the isolated host cell comprises fungal mycelia of the genus *Penicillium*, preferably *P. paxilli*.

Specifically contemplated for this aspect of the invention are various embodiments set out for any other aspect of the invention that relate to the heterologous expression (including choice of appropriate regulatory sequences), genetic elements, TUs, multigene constructs, host cells, and vectors.

In another aspect the invention relates to a method of producing at least one NA comprising contacting a carbohydrate comprising substrate with a recombinant cell transformed with a nucleic acid that results in an increased level or activity of a polypeptide selected from the group consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof compared to the cell prior to transformation, such that the substrate is metabolized to at least one NA.

In one embodiment the nucleic acid encodes at least one polypeptide that catalyzes a biochemical reaction in the biosynthetic pathway leading from GGI 2 to NAF 5a, preferably that catalyzes the biochemical reaction that leads from emindole SB 4a to NAF 5a.

In one embodiment the recombinant host cell is an isolated host cell of the invention as described herein.

In one embodiment the carbohydrate is comprised in a culture media. In one embodiment the culture media is CDYE or a variation thereof that supports the growth of the recombinant cell.

In one embodiment the nucleic acid encodes least one polypeptide that is an oxygenase, preferably a cytochrome P450 oxygenase or a FAD-dependent oxygenase. Preferably the cytochrome P450 oxygenase is NodW (SEQ ID NO:3), NodR (SEQ ID NO:6), NodX (SEQ ID NO:9), NodJ (SEQ ID NO:21), or NodZ (SEQ ID NO:39). Preferably the FAD dependent oxygenase is NodM (SEQ ID NO:12), NodO (SEQ ID NO:18), NodY1 (SEQ ID NO:27), or NodY2 (SEQ ID NO:36). In one embodiment the isolated polypeptide is a transferase, preferably a GGT, or a prenyl transferase. Preferably the GGT is NodC (SEQ ID NO:24). Preferably the prenyl transferases are NodD1 (SEQ ID NO:33), or NodD2 (SEQ ID NO:30). In one embodiment the isolated polypeptide is a IDT cyclase.

Preferably the IDT cyclase is NodB (SEQ ID NO:15). In one embodiment the isolated polypeptide is NodS (SEQ ID NO:50). In one embodiment the isolated polypeptide is NodI (SEQ ID NO:56).

In one embodiment the nucleic acid encodes at least one GGT, FAD-dependent oxygenase, IDT cyclase, or cytochrome P450 oxygenase. In one embodiment the nucleic acid codes at least two, preferably at least three, preferably all four of the GGT, FAD-dependent oxygenase, IDT cyclase, or cytochrome P450 oxygenase. Preferably the GGT is NodC (SEQ ID NO:24). Preferably the FAD-dependent oxygenase is NodM (SEQ ID NO:12). Preferably the IDT cyclase is NodB (SEQ ID NO:15). Preferably the cytochrome P450 oxygenase is NodW (SEQ ID NO:3).

In one embodiment a polypeptide selected from the group consisting of NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or a functional variant or fragment thereof comprises the amino acid sequence of a NodW (SEQ ID NO:3), NodR (SEQ ID NO:6), NodX (SEQ ID NO:9), NodM (SEQ ID NO:12), NodB (SEQ ID NO:15), NodO (SEQ ID NO:18), NodJ (SEQ ID NO:21), NodC (SEQ ID NO:24), NodY1 (SEQ ID NO:27), NodD2 (SEQ ID NO:30), NodD1 (SEQ ID NO:33), NodY2 (SEQ ID NO:36), NodZ (SEQ ID NO:39), NodS (SEQ ID NO:50), and NodI (SEQ ID NO:56) or functional variant or fragment thereof of the invention.

In one embodiment the polypeptide comprises the amino acid sequence of NodW (SEQ ID NO:3) or a functional variant or fragment thereof. Preferably the polypeptide consists essentially or consists of SEQ ID NO: NodW (SEQ ID NO:3). In one embodiment the isolated host cell comprises fungal mycelia of the genus *Penicillium*, preferably *P. paxilli*.

Specifically contemplated for this aspect of the invention are various embodiments set out for any other aspect of the invention that relate to the heterologous expression (including choice of appropriate regulatory sequences), genetic elements, TUs, multigene constructs, host cells, and vectors.

In one embodiment the at least one heterologous or introduced homologous nucleic acid sequence is at least one NAA 10 biosynthetic gene selected from the group consisting of nodW, nodR, nodX, nodM, nodB, nodO, nodJ, nodC, nodY1, nodD2, nodD1, nodY2, nodZ nodS, and nodI as described herein.

In one embodiment one of the two different GGPPS enzymes is produced in *H. pulicicidum* by heterologous expression.

In one embodiment one of the two different GGPPS enzymes is encoded by a second copy of a native *H. pulicicidum* gene that encodes a GGPPS enzyme.

In another aspect the invention relates to an isolated strain of *Hypoxylon* pulicicidum that comprises a genetic modification that leads to an increased biosynthesis of NAA 10.

In one embodiment the isolated strain comprises increased expression of at least one GGPPS enzyme as compared to a control strain of *H. pulicicidum*, preferably *H. pulicicidum* ATCC 74245.

In one embodiment the increased expression is increased expression of the native primary GGPPS gene of *H. pulicicidum* via modification of genetic regulatory elements.

In one embodiment modification of genetic regulatory elements comprises operatively linking the native primary GGPPS gene to an alternative or modified promoter.

In one embodiment modification of genetic regulatory elements comprises operatively linking a native primary GGPPS gene to a more robust native promoter. In one embodiment the native primary GGPPS gene is an introduced homologous gene.

In one embodiment the increased expression is the result of heterologous expression of biosynthetic genes that contribute to NAA 10 biosynthesis.

In one embodiment the increased expression is due to expression of heterologous genes in *H. pulicicidum* that have equivalent biochemical function to genes identified in the Nod cluster, wherein the Nod cluster is as described herein.

In one embodiment the increased expression is due to expression of heterologous genes in *H. pulicicidum* to remediate limitations in the supply of substrate compounds or biosynthetic intermediates that are necessary for NAA 10 biosynthesis.

In one embodiment the increased expression is due to heterologous expression in *H. pulicicidum* of any gene that encodes a GGT that catalyzes the condensation of GGPP 1*a* and indole-3-glycerol phosphate 1*b* to produce 3-geranylgeranyl indole 2.

In one embodiment the increased expression is due to heterologous expression in *H. pulicicidum* of any gene that encodes a GGPPS.

In one embodiment the increased expression is due to heterologous expression in *H. pulicicidum* of any gene that encodes a FAD-dependent oxidase that creates the single epoxidized-GGI product 3*a*.

In one embodiment the increased expression is due to heterologous expression in *H. pulicicidum* of any gene that encodes an enzyme that cyclises the single epoxidized-GGI 3*a* to produce emindole SB 4*a*.

In one embodiment the increased expression is due to heterologous expression in *H. pulicicidum* of any gene that encodes an oxidase that oxidises emindole SB 4*a* to produce a nodulisporic acid.

In one embodiment the increased expression is due to at least one genetic modification that leads to the increased expression of a NA biosynthetic gene selected from the group consisting of nodW, nodR, nodX, nodM, nodB, nodO, nodJ, nodC, nodY1, nodD2, nodD1, nodY2, nodZ, nodS and nodI as described herein.

In another aspect the invention relates to a method of making NAA 10 comprising expressing at least one heterologous nucleic acid sequence in *Hypoxylon pulicicidum*, wherein the at least one heterologous nucleic acid sequence encodes an enzyme in a biosynthetic pathway leading to NAA 10.

Specifically contemplated for this aspect of the invention are various embodiments set out for any other aspect of the invention that relate to the isolated strains of *Hypoxylon pulicicidum* as described herein including as relates to increased expression of NAA 10, and also including all embodiments set out regarding heterologous expression (including choice of appropriate regulatory sequences), genetic elements, TUs, multigene constructs, host cells, and vectors as described herein.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents; or such sources of information, in any jurisdiction, are prior art, or form part of the common general knowledge in the art.

The invention will now be illustrated in a non-limiting way by reference to the following examples.

EXAMPLES

Materials and Methods gDNA Isolation for Genome Sequencing and TUM Amplification Genomic DNA for genome sequencing and TUM amplification by PCR was isolated from *Penicillium paxilli* strain ATCC® 26601™ (PN2013)[24] and *Hypoxylon pulicicidum* strain ATCC® 74245®,[25] according to Byrd et al.[26] with modifications. Sterile 2.4% (w/v) Difco™ potato dextrose broth (Becton, Dickinson and Company, Maryland, U.S.A.) in Milli-Q® water was prepared in 25 mL aliquots in 125 mL Erienmeyer flasks and inoculated with 5×10$^6$ spores or ~1 cm$^2$ freshly ground mycelia (for non-sporulating strains). Cultures were incubated for 2-4 days at 22° C. with shaking (200 rpm). The fermentation broth was filtered through a sterile nappy liner and the mycelia were rinsed three times with sterile water. Mycelia was transferred to a sterile 15 mL centrifuge tube and flash frozen in liquid nitrogen for lyophilization for 24-48 hours. 15-20 mg freeze dried mycelia was placed in a mortar with liquid nitrogen and ground into a powder. The ground mycelia was transferred into a 2 mL tube and resuspended in 1 mL extraction buffer (150 mM EDTA, 50 mM Tris-HCl, and 1% (w/v) sodium lauroyl sarcosine). 1.6 mg proteinase K was added to the tube and contents were incubated at 37° C. for 30 min. The tube was centrifuged at 13,000 rpm for 10 min and the supernatant was transferred to a fresh 2 mL tube. 500 µL phenol and 500 µL chloroform were added to the tube and the contents were mixed by vortex before centrifugation for 10 min at 13,000 rpm. The aqueous phase was transferred to a fresh 2 mL tube and washed two more times with 500 µL phenol and 500 µL chloroform as previously described. The aqueous phase was then transferred to a fresh 2 mL tube and washed (vortex and centrifuge at 13,000 rpm for 10 min) with 1 mL chloroform. The aqueous phase was transferred to a fresh 2 mL tube and mixed with 1 mL chilled isopropanol. The DNA was precipitated overnight at −20° C. and pelleted at 13,000 rpm for 10 min. The supernatant was discarded and the DNA was resuspended in 1 mL 1 M NaCl. The tube was incubated for 10 min at room temperature and then centrifuged at 13,000 rpm for 10 min to pellet polysaccharides. The supernatant was transferred to a fresh tube and mixed with 1 mL isopropanol. The tube was incubated at room temperature for 10 min and DNA was pelleted by centrifugation at 13,000 rpm for 10 min. The supernatant was discarded and 1 mL chilled 70% ethanol was added to the pellet without resuspension. The tube was centrifuged for 2 min at 13,000 rpm and the supernatant was discarded. The tube was centrifuged for 1 min at 13,000 rpm and residual 70% ethanol was pipette off. The pellet was air dried at room temperature, resuspended in 50 µL Milli-Q® water and stored at −20° C.

MIDAS Design Overview

The MIDAS toolkit is based on the Golden Gate assembly technique,[27] which utilises the ability of Type IIS restriction enzymes to seamlessly join multiple DNA fragments together in a single reaction. MIDAS makes use of three Type IIS restriction enzymes, AarI, BsaI and BsmBI, which generate user-defined 4 bp overhangs upon cleavage. Through the appropriate choice of these user-defined overhangs, and the appropriate orientation of the Type IIS sites flanking each of the DNA fragments, multiple fragments can be assembled into a recipient plasmid (also called a destination vector) in an ordered (directional) fashion using a one-pot restriction-ligation reaction. The recipient plasmid contains a marker gene (typically the lacZa gene for blue/white screening) flanked by two divergently oriented recognition sites for a Type IIS enzyme; these elements, collectively called the 'Golden Gate cloning cassette', are replaced by the insert during the assembly reaction.

As with other recently described Golden Gate-based modular assembly techniques,[28-32] assembly of genes and multigene constructs using MIDAS is a hierarchical process. At the first level (MIDAS Level-1), functional modules (promoters, CDS, terminators, tags, etc.) are cloned into the Level-1 destination vector (pML1), where they form libraries of reusable, sequence-verified parts. The complementary design of the modules and destination vector ensures that, once cloned into pML1, these modules can be released from the vector by digestion with BsaI.

At the second level (Level-2), compatible sets of the sequence-verified Level-1 modules are released from pML1 and assembled into a Level-2 destination vector (pML2) using a BsaI-mediated Golden Gate reaction, leading to creation of a Level-2 plasmid containing a eukaryotic TU. Once again, the design rules ensure that each assembled TU can be released from the pML2 vector—this time by digestion either with AarI or BsmBI (depending on the pML2 vector in which the TU was assembled).

At Level-3, the TUs that were assembled at Level-2 are released from the pML2 plasmids and are sequentially assembled together in a Level-3 destination vector (pML3), using either AarI- or BsmBI-mediated Golden Gate reactions, to form functional multigene constructs, which can then be transformed into the desired expression host.

Level-1: Module Cloning

Figure 11:
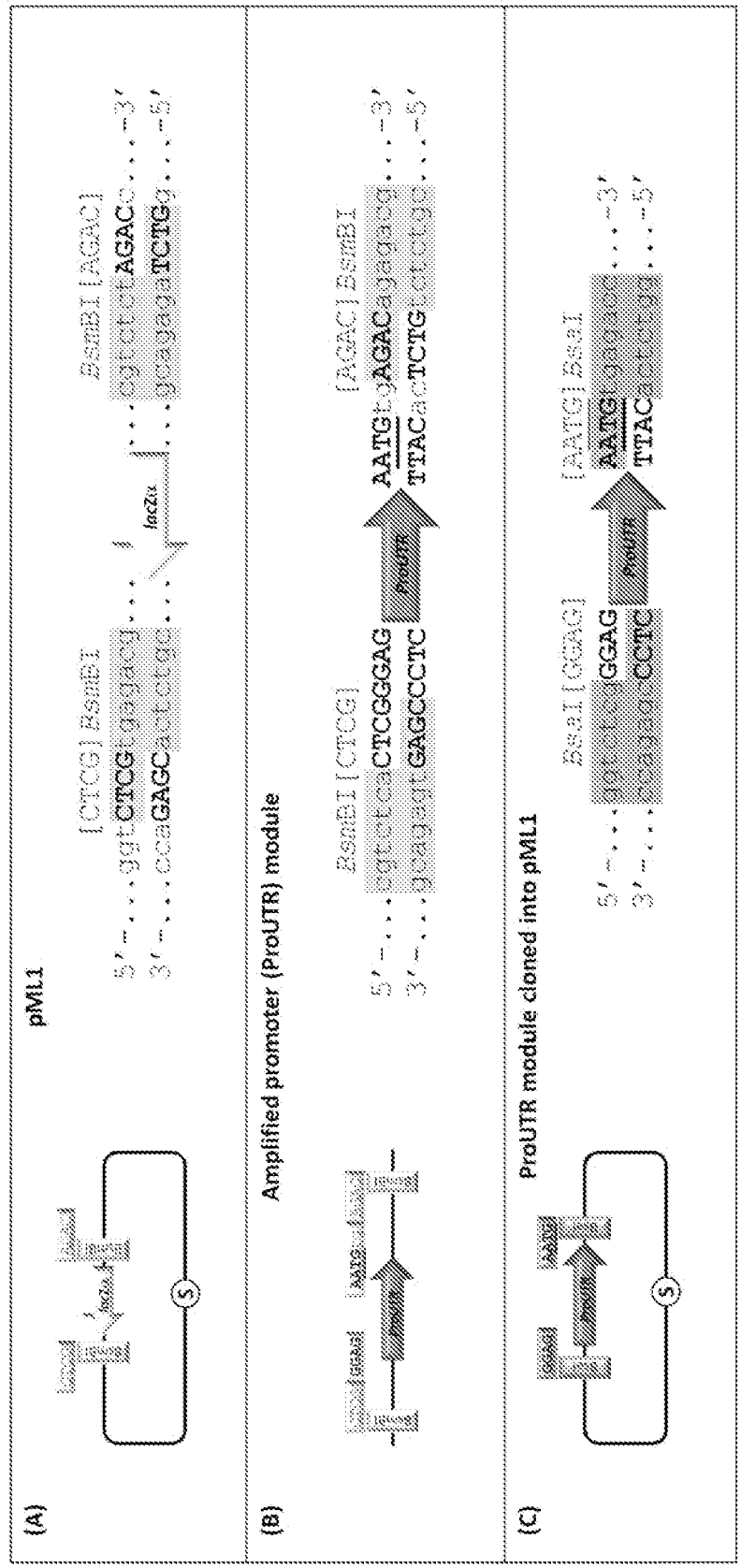
FIG. 11: Overview of MIDAS Level-1 cloning. (A) ggtctcgtgagacg (SEQ ID NO: 125); cgtctctagacc (SEO ID NO: 126); ccagagcactctgc (SEO ID NO: 127); gcagagatctgg (SEQ ID NO: 128); (B) cgtctcactcgggag (SEQ ID NO: 129); aatgtgagacagagacg (SEO ID NO: 130); gcagagtgagccctc (SEO ID NO: 131); ttacactctgtctctgc (SEO ID NO: 132); (C) ggtctcgggag (SEO ID NO: 133); aatgtgagacc (SEO ID NO: 134); ccagagcccctc (SEO ID NO: 135); ttacactctgg (SEO ID NO: 136)

At Level-1, functional TUMs are generated, either as a PCR product, or as a synthetic polynucleotide sequence (from a gene synthesis company), and are cloned into the Level-1 destination vector (pML1) by BsmBI-mediated Golden Gate cloning. In order to be cloned into the pML1 vector, the PCR primers are designed so that each amplified TUM is flanked by two convergent BsmBI sites, BsmBI [CTCG] and [AGAC]BsmBI, which upon restriction enzyme cleavage, generate sticky ends that are compatible with those of the BsmBI sites present in the pML1 destination vector. Thus, the Golden Gate cloning cassette present in pML1 consists of two divergent BsmBI sites flanking a lacZa scoreable marker: 5'-[CTCG]BsmBI-lacZa-BsmBI [AGAC]-3' (FIG. 11A).

To enable subsequent (i.e., Level-2) assembly of full-length TUs, each TUM is designed to be flanked by four module-specific nucleotides (NNNN) at the 5' end, and four module-specific nucleotides (NNNN) at the 3' end, which are included as part of the PCR primer sequences. The complementary design of the amplified modules and the pML1 vector ensures that, when amplified TUMs are cloned into pML1 using the BsmBI-mediated Golden Gate reaction, each TUM becomes flanked by convergent BsaI recognition sites, and the module-specific nucleotides (NNNN and NNNN) become the BsaI-specific 4 bp overhangs when the module is released from pML1 during the subsequent (i.e., Level-2) BsaI-mediated Golden Gate assembly of the full-length TU. Thus, the overall structure of each module in the PCR product (or synthetic polynucleotide) takes the form: 5'-BsmBI[CTCG]NNNN-TUM-NNNNtg[AGAC]BsmBI-3' (FIG. 11B), which becomes 5'-BsaI[NNNN]-TUM-[NNNN] BsaI-3' in pML1, following BsmBI-mediated cloning (FIG. 11C).

Figure 12:
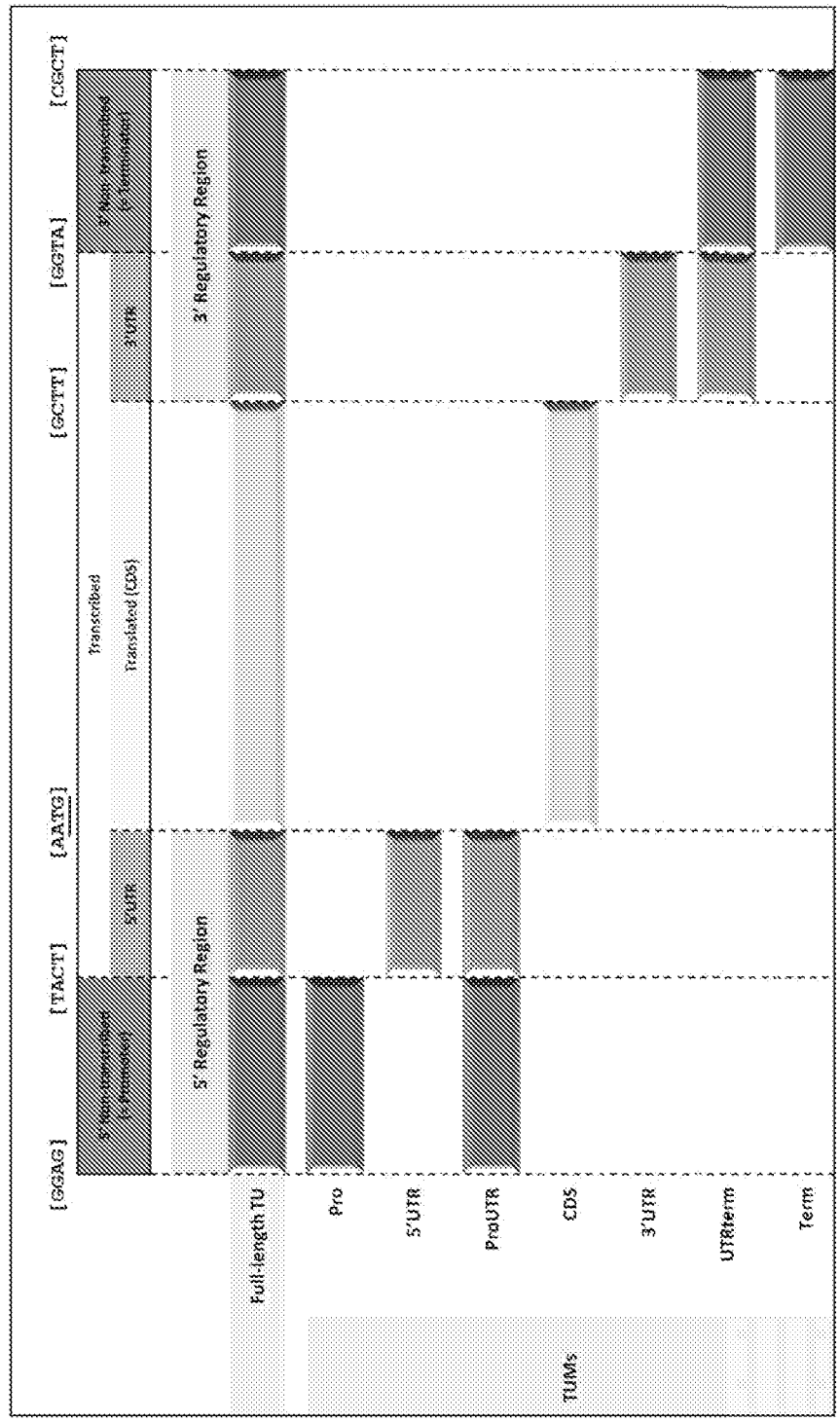
FIG. 12: MIDAS module address system.

As each TUM is defined by its flanking four nucleotides, these module-specific bases effectively form an address system for each TUM and they determine its position and orientation within the assembled TU. The developers of MoClo and GoldenBraid2.0 have already worked in concert to develop a common syntax or set of standard addresses for plant expression (referred to as 'fusion sites' in the MoClo system and 'barcodes' in GoldenBraid2.0) for a wide variety of TUMs to facilitate part exchangeability,[33] and this standard is also adopted here for MIDAS-based assembly of TUs for expression in filamentous fungi (FIG. 12).

Thus, for filamentous fungal expression, a ProUTR module (comprising a promoter, 5' untranslated region (UTR) and ATG initiation codon) would have GGAG as the module-specific 5' nucleotides, and AATG as the module-specific 3' nucleotides (i.e., 5'-GGAG-ProUTR-A<u>ATG</u>-3'), with the translation initiation codon underlined. Similarly, a CDS module would be flanked by AATG and GCTT (i.e., 5'-A<u>ATG</u>-CDS-GCTT-3'), while a UTRterm module (consisting of a 3'UTR and a 3' non-transcribed region, including the polyadenylation signal) would have the form 5'-GCTT-UTRterm-CGCT-3'. Considerations for the design of PCR primers for amplifying these three types of TUM are shown in Table 12.

Following the BsmBI-mediated assembly of TUMs in pML1, reactions are transformed into an *E. coli* strain such as DH5α (or equivalent) and spread onto LB plates supplemented with spectinomycin, IPTG and X-Gal. Plasmids harbouring a cloned TUM are identified by screening white colonies and confirmed by sequencing.

At MIDAS Level-1, it is important that all internal recognition sites for AarI, BsaI and BsmBI are masked or eliminated from the TUMs. The process of masking or removal of such forbidden sites—referred to as "domestication"—can be achieved by; (i) excluding these sites when ordering the sequences from a gene synthesis company, (ii) directed mutagenesis, or (iii) using masking oligonucleotides that form triplexes with the target DNA, thereby preventing restriction enzyme cleavage.[30] In the same way that Type IIS enzymes have previously been utilised for mutagenesis[34] and for Golden Gate domestication purposes,[27,35] we domesticated MIDAS modules by designing PCR primers (referred to as domestication primers) that overlap the internal Type IIS restriction site and which contain a single nucleotide mismatch that destroys the site. Because the PCR products are designed to be assembled together in MIDAS using a BsmBI-mediated Golden Gate reaction to form the full-length domesticated TUM in pML1, it is important that the MIDAS domestication primers be designed with BsmBI restriction sites that generate compatible overhangs at their 5' ends.

Level-2: TU Assembly

At Level-2, compatible sets of cloned and sequence-verified Level-1 TUMs (for example ProUTR, CDS and UTRterm modules) are assembled into a pML2 destination vector using a BsaI-mediated Golden Gate reaction, leading to creation of a Level-2 plasmid (pML2 entry clone) containing a complete (i.e., full-length) eukaryotic TU. The module address standard described earlier ensures that the assembly of a TU proceeds in an ordered, directional fashion, with the 3' end of one module being compatible with the 5' end of the next module.

The module-specific bases GGAG, located at the 5' end of ProUTR modules, and CGCT, at the 3' end of UTRterm modules, are compatible with the overhangs generated by BsaI digestion of the pML2 destination vectors, and these bases therefore define the outermost cloning boundaries of a Level-2 assembly.

In MIDAS, there are eight Level-2 (pML2) destination vectors into which a TU can be assembled, the choice of which depends on the desired configuration of TUs in the multigene plasmid produced at Level-3, namely: (i) the desired order in which TUs are added to the multigene assembly, (ii) the desired direction in which the multigene plasmid is assembled and (iii) the desired orientation of each TU in the multigene plasmid. These features are discussed further below.

The pML2 vectors are distinguished from one another by the arrangement of specific sequence features that are central to the operation of MIDAS. These sequence features, collectively called the MIDAS cassette (FIG. 13), define the Level-2 assembly of TUs and govern the assembly of multigene constructs produced at Level-3.

Each MIDAS cassette is defined by (i) having a Golden Gate cloning cassette with flanking, divergent BsaI recognition sites, (ii) differing arrangements of recognition sites for AarI and BsmBI and (iii) the presence or absence of a lacZα scoreable marker. These features are described in greater detail.

In contrast to the usual Golden Gate cloning cassette (which typically contains a lacZα gene for blue/white screening), the Golden Gate cloning cassettes in all eight pML2 vectors contain a mutant *E. coli* pheS gene (driven by the promoter of the *E. coli* gene for chloramphenicol acetyltransferase) flanked by divergent BsaI recognition sites. The Thr$^{251}$Ala/Ala$^{294}$Gly double mutant of the *E. coli* pheS gene used here confers high lethality to cells grown on LB media supplemented with the phenylalanine analogue 4-chloro-phenylalanine, 4CP.[36] During BsaI-mediated Level-2 assembly of TUs, the mutant pheS gene is eliminated from the pML2 vectors and can therefore be used as a negative selection marker.

Figure 13:
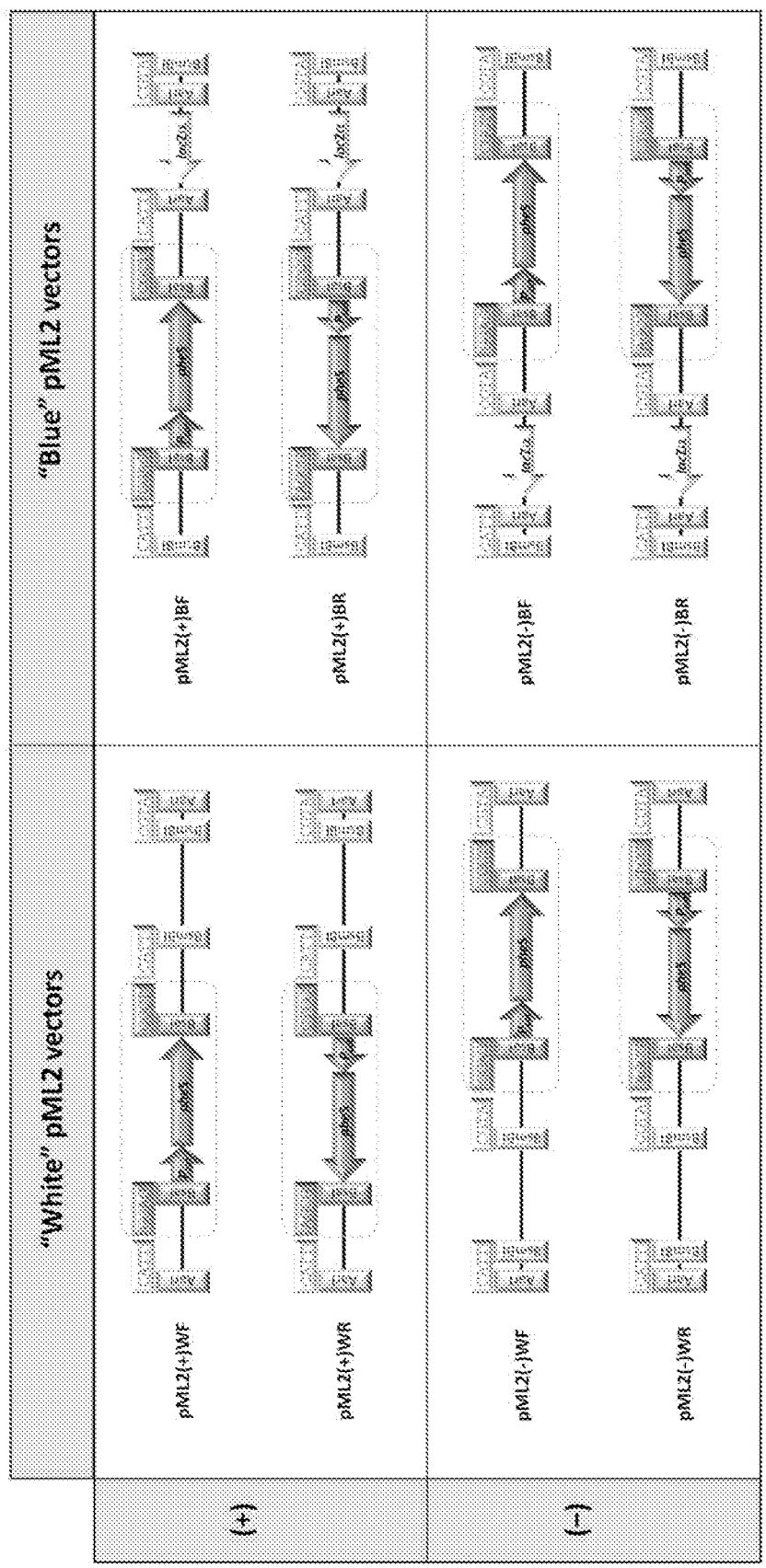
FIG. 13: Overview of MIDAS cassettes.

The eight pML2 vectors can be divided into two classes, "Blue" and "White", depending on the presence or absence, respectively, of a lacZα gene in the MIDAS cassette (see FIG. 13). There are four "Blue" pML2 vectors (indicated by the "B" in the plasmid name) and four "White" pML2 vectors (indicated by the "W" in the plasmid name). The "Blue" and "White" vectors also differ in the relative configuration of the AarI and BsmBI restriction sites in their MIDAS cassettes. Thus, in the "Blue" vectors, the entire MIDAS cassette is flanked by convergent BsmBI sites and nested within is the lacZα gene flanked by divergent AarI sites. In the "White" vectors, the enzyme configuration is switched (the entire MIDAS cassette is flanked by convergent AarI sites and nested within are two divergent BsmBI sites) and there is no lacZα gene. It is important to note that the lacZα chromogenic marker in the pML2 vectors is not used for blue/white screening during the Level-2 Golden Gate assembly of TUs (it is reserved for the Level-3 cloning), but the choice of "Blue" or "White" vector into which a TU should be assembled must be made during Level-2 assembly of TUs as this will determine the order in which that TU is added to the multigene construct at Level-3. Likewise, the AarI and BsmBI sites are also not used for Level-2 assembly of TUs; instead they are integral to the Level-3 assembly of multigene constructs. These considerations, including the differences between the (+) and (−) vectors, are discussed further below, under the Level-3 description.

The orientation (direction of transcription) of each TU can be freely defined by assembling each TU in either a pML2 "Forward" vector (indicated by "F" in the plasmid name) or a pML2 "Reverse" vector (indicated by "R" in the plasmid name). The pML2 "Reverse" vectors have their BsaI recognition sites (for Golden Gate assembly of TUs) switched relative to the BsaI fusion sites in the pML2 "Forward" vectors. Thus, pML2 "Forward" vectors have their pheS-based Golden Gate cassette oriented 5'-[GGAG]BsaI-pheSs ▶-BsaI[CGCT]-3', while the pML2 "Reverse" vectors have their BsaI recognition sites switched: 5'-[AGCG]BsaI-◀pheS-BsaI[CTCC]-3', where the arrowhead indicates the direction of transcription of the mutant pheS gene.

In contrast to the cloned Level-1 modules, the pML2 destination vectors confer kanamycin resistance, allowing efficient counter selection against Level-1 module backbones, while the mutant pheS gene provides powerful negative selection against any parental pML2 destination plasmids when E. coli DH5α cells (or equivalent) transformed with the assembly reactions are spread onto LB plates supplemented with kanamycin and 4CP.

Level-3: Assembly of Multigene Constructs

At MIDAS Level-3, TUs that were assembled in the pML2 plasmids are sequentially loaded (by binary assembly) into the Level-3 destination vector (pML3) to form the multigene construct.

Figure 14:
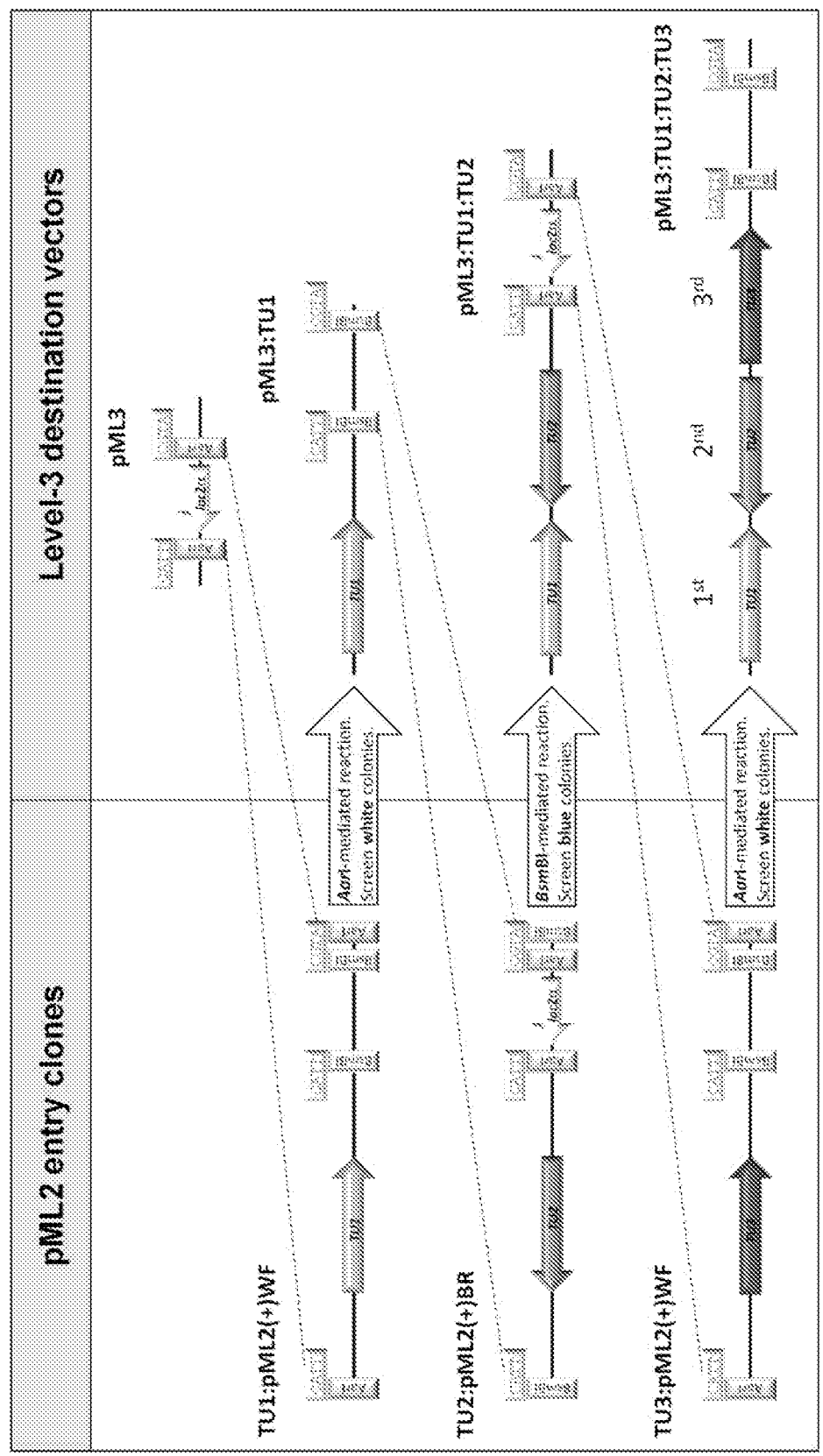
FIG. 14: Principle of MIDAS multigene assembly (level-3).

Assembly of multigene constructs at Level-3 is crucially dependent on the relative configuration of the AarI and BsmBI restriction sites in the MIDAS cassettes located in the "Blue" and "White" pML2 vectors; the nested and inverted configuration of these restriction sites in the White vectors compared to the Blue vectors is a defining feature of the MIDAS multigene assembly process. In the "Blue" vectors, the entire MIDAS cassette has flanking convergent BsmBI sites and nested within is a lacZa gene flanked by divergent AarI sites. In the "White" vectors, the enzyme configuration is inverted (the entire MIDAS cassette has flanking convergent AarI sites and nested within are two divergent BsmBI sites) and there is no lacZa gene. As illustrated in FIG. 14, the nesting and inversion of the restriction sites in the "Blue" and "White" vectors mean that TUs assembled into "White" MIDAS cassettes can be inserted into "Blue" MIDAS cassettes using AarI-mediated Golden Gate reactions and, conversely, TUs assembled into "Blue" MIDAS cassettes can be cloned into "White" MIDAS cassettes using BsmBI-mediated Golden Gate reactions. This cycle of cloning (i.e., alternating between "White" and "Blue" pML2 entry clones) can be repeated indefinitely.

The Golden Gate cloning cassette found in the Level-3 destination vector, pML3, consists of a lacZa gene flanked by divergent AarI sites: [CATT]AarI-lacZa-AarI[CGTA], so the MIDAS Level-3 assembly is always initiated (i.e., the first TU is always added) using an AarI-mediated Golden Gate reaction between pML3 and a TU that has been assembled into a pML2 "White" destination vector (FIG. 14). The plasmid generated is then used in a BsmBI-mediated Golden Gate reaction with a TU cloned into a pML2 "Blue" destination vector. Further TUs are added by following this approach of alternating between AarI- and BsmBI-mediated Golden Gate reactions using pML2 "White" and pML2 "Blue" entry clones, respectively. Thus, each plasmid generated by cloning a TU into the multigene construct becomes the destination vector for the next cycle of TU addition (FIG. 14).

Following each cloning cycle, E. coli DH5α cells (or equivalent) are transformed with the Golden Gate reactions, spread onto LB plates supplemented with spectinomycin, IPTG and X-Gal, and positive clones are identified by blue/white screening. Spectinomycin selects for cells that have taken up the Level-3 plasmid and counter selects against any pML2 plasmid backbones. Note that, whereas the lacZa chromogenic marker present in the pML2 "Blue" vectors was not previously utilised during Level-2 assembly of TUs, it is now, at the level of multigene assembly (Level-3), that it becomes used for blue/white screening. Thus, for TUs assembled into the multigene construct using AarI-mediated Golden Gate reactions, white colonies are picked for analysis, while TUs assembled into the multigene construct using BsmBI-mediated Golden Gate reactions are analysed by picking blue colonies (see Table 13).

Figure 15:
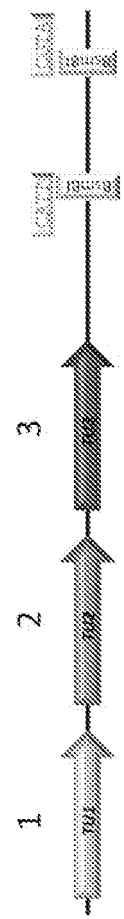
FIG. 15: Overview of MIDAS format.
Figure 15:
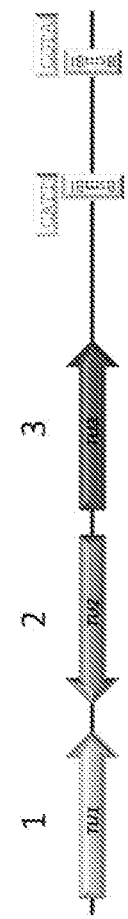
Figure 15:
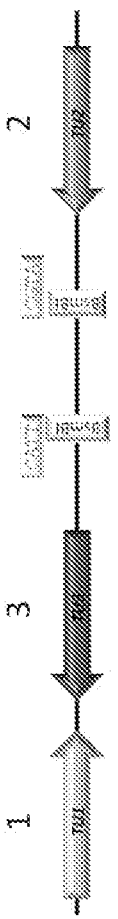

In its simplest configuration, MIDAS can achieve multigene assembly using only two pML2 destination vectors: one "White" vector and one "Blue" vector (FIG. 15A). The full set of eight pML2 vectors are provided to enable maximum user control over: (i) the order in which each TU is added to the growing multigene construct, (ii) the desired orientation (that is, the direction of transcription) of each TU and (iii) the polarity of assembly, i.e., the direction in which incoming TUs are loaded into the multigene construct.

Firstly, and as described earlier, the order of addition of each TU to the growing multigene construct is governed by the choice of "White" or "Blue" pML2 destination vector into which the TUs are assembled.

Secondly, and as described previously when discussing the Level-2 features, the orientation (direction of transcription) of a TU can be freely defined by the choice of "Forward" or "Reverse" pML2 vector into which the TU is assembled. Extending MIDAS to include the option of assembling TUs in either orientation expands the vector suite to four pML2 plasmids (see FIG. 13 and FIG. 15B).

Thirdly, the polarity of multigene assembly (i.e., the direction in which new TUs are added to the growing multigene assembly) can also be freely defined—in this case by assembling TUs in pML2 destination vectors of either "plus" (+) or "minus" (−) polarity (FIG. 13). The use of a pML2(+) entry clone for Level-3 assembly ensures that the TU added next will be added in the same direction as the direction of transcription of the Spec$^R$ gene found in pML3, i.e. the TU assembled next in the multigene construct will be added to the right of the TU that was added using the pML2(+) entry clone (as illustrated in FIG. 15A and FIG. 15B). In contrast, use of a pML2(−) entry clone for Level-3 assembly forces the next TU to be added in the direction opposite to that of the direction of transcription of the Spec$^R$ gene found in pML3, so that the next TU loaded into the multigene construct will be added to the left of the TU that was added using the pML2(−) entry clone. If, however, entry clones of both polarity (i.e., both pML2(+) and pML2(−) entry clones) are used to build the multigene construct, then this confers MIDAS with the ability to switch the direction in which new TUs are added to the Level-3 assembly, and for the hypothetical assembly shown in FIG. 15C all subsequently added TUs will be nested between TU3 and TU2.

Bacterial and Fungal Strains

Routine growth of *Escherichia coli* was performed at 37° C. in LB broth. Chemically competent *E. coli* HST08 Stellar cells (Clontech Laboratories, Inc.) were used for routine transformations and maintenance of plasmids. *Penicillium paxilli* strains used in this study are shown in Table 7.

Protocols for MIDAS Level-1 Module Cloning

PCR-amplified modules were purified using spin-column protocols and cloned into the MIDAS Level-1 plasmid, pML1, by BsmBI-mediated Golden Gate assembly. Typically, 1-2 μL (approximately 50-200 ng) of pML1 plasmid DNA from a miniprep was mixed with 1-2 μL of each purified PCR fragment, 1 μL of BsmBI (20 U/μL), 1 μL of T4 DNA Ligase (20 U/μL) and 2 μL of 10× T4 DNA Ligase buffer in a total reaction volume of 20 μL. Reactions were incubated at 37° C. for 1 to 3 hours and an aliquot (typically 2-3 μL) was transformed into 30 μL of *E. coli* HST08 Stellar competent cells by heat shock. Following the recovery period (i.e., addition of 250 μL SOC medium and incubation at 37° C. for 1 hour), aliquots of the transformation mix were spread onto LB agar plates supplemented with 50 μg/mL spectinomycin, 1 mM IPTG and 50 μg/mL X-Gal. Plates were incubated overnight at 37° C., and white colonies were chosen for analysis.

Protocols for MIDAS Level-2 TU Assembly

Using the modules cloned at Level-1, full-length TUs were assembled into MIDAS Level-2 plasmids by BsaI-mediated Golden Gate assembly. Typically, 40 fmol of pML2 plasmid DNA was mixed with 40 fmol of plasmid DNA of each Level-1 entry clone, 1 μL of BsaI-HF (20 U/μL), 1 μL of T4 DNA Ligase (20 U/μL) and 2 μL of 10× T4 DNA Ligase buffer in a total reaction volume of 20 μL. Reactions were incubated in a DNA Engine PTC-200 Peltier Thermal Cycler (Bio-Rad) using the following parameters: 45 cycles of (2 minutes at 37° C. and 5 minutes at 16° C.), followed by 5 minutes at 50° C. and 10 minutes at 80° C. Reactions were transformed as described for the Level-1 assembly and spread onto LB agar plates containing 75 μg/mL kanamycin and 1.25 mM 4CP. Following overnight incubation at 37° C., colonies were picked for analysis.

Protocols for MIDAS Level-3 Multigene Assembly

Full-length TUs assembled at Level-2, were used to create multigene assemblies in the Level-3 destination vector by alternating Golden Gate assembly using either AarI (for TUs cloned into pML2 "White" vectors) or BsmBI (for TUs cloned into pML2 "Blue" vectors). Typically, 40 fmol of Level-3 destination vector plasmid DNA was mixed with 40 fmol of Level-2 entry clone plasmid DNA, 1 μL of BsaI-HF (20 U/μL), 1 μL of T4 DNA Ligase (20 U/μL) and 2 μL of 10× T4 DNA Ligase buffer in a total reaction volume of 20 μL. Reactions were incubated in a DNA Engine PTC-200 Peltier Thermal Cycler (Bio-Rad) using the following parameters: 45 cycles of (2 minutes at 37° C. and 5 minutes at 16° C.), followed by 5 minutes at 37° C. and 10 minutes at 80° C. Reactions were transformed as described for the Level-1 assembly and spread onto LB agar plates supplemented with 50 μg/mL spectinomycin, 1 mM IPTG and 50 μg/mL X-Gal. Plates were incubated overnight at 37° C. For AarI-mediated assembly reactions, white colonies were chosen for analysis while, for BsmBI-mediated assembly reactions, blue colonies were selected.

Media and Reagents Used for Fungal Work.

CDYE (Czapex-Dox/Yeast extract) medium with trace elements was made with deionized water and contained 3.34% (w/v) Czapex-Dox (Oxoid Ltd., Hampshire, England), 0.5% (w/v) yeast extract (Oxoid Ltd., Hampshire, England), and 0.5% (v/v) trace element solution. For agar plates, Select agar (Invitrogen, California, U.S.A.) was added to 1.5% (w/v).

Trace element solution was made in deionized water and contained 0.004% (w/v) cobalt(II) chloride hexahydrate (Ajax Finechem, Auckland, New Zealand), 0.005% (w/v) copper(II) sulfate pentahydrate (Scharlau, Barcelona, Spain), 0.05% (w/v) iron(II) sulfate heptahydrate (Merck, Darmstadt, Germany), 0.014% (w/v) manganese(II) sulfate tetrahydrate, and 0.05% (w/v) zinc sulfate heptahydrate (Merck, Darmstadt, Germany). The solution was preserved with 1 drop of 12 M hydrochloric acid.

Regeneration (RG) medium was made with deionized water and contained 2% (w/v) malt extract (Oxoid Ltd., Hampshire, England), 2% (w/v) D(+)-glucose anhydrous (VWR International BVBA, Leuven, Belgium), 1% (w/v) mycological peptone (Oxoid Ltd., Hampshire, England), and 27.6% sucrose (ECP Ltd. Birkenhead, Auckland, New Zealand). Depending on whether the media was to be used for plates (1.5% RGA) or overlays (0.8% RGA), Select agar (Invitrogen, California, U.S.A.) was added to 1.5% or 0.8% (w/v), respectively.

Fungal Protocols—Protoplast Preparation

The preparation of fungal protoplasts for transformation was according to Yelton et al.[37] with modifications. Five 25 mL aliquots of CDYE medium with trace elements, in 100 mL Erlenmeyer flasks, were inoculated with $5\times10^6$ spores and incubated for 28 hours at 28° C. with shaking (200 rpm). The fermentation broth from all five flasks was filtered through a sterile nappy liner and the combined mycelia were rinsed three times with sterile water and once with OM buffer (10 mM $Na_2HPO_4$ and 1.2 M $MgSO_4.7H_2O$, brought to pH 5.8 with 100 mM $NaH_2PO_4.2H_2O$). Mycelia were weighed, resuspended in 10 mL of filter-sterilized Lysing Enzymes solution (prepared by resuspending Lysing Enzymes from Trichoderma harzianum (Sigma) at 10 mg/mL in OM buffer) per gram of mycelia, and incubated for 16 hours at 30° C. with shaking at 80 rpm. Protoplasts were filtered through a sterile nappy liner into a 250 mL Erlenmeyer flask. Aliquots (5 mL) of filtered protoplasts were transferred into sterile 15 mL centrifuge tubes and overlaid with 2 mL of ST buffer (0.6 M sorbitol and 0.1 M Tris-HCl at pH 8.0). Tubes were centrifuged at 2600×g for 15 minutes at 4° C. The white layer of protoplasts that formed between the OM and ST buffers in each tube was transferred (in 2 mL aliquots) into sterile 15 mL centrifuge tubes, gently washed by pipette resuspension in 5 mL of STC buffer (1 M sorbitol, 50 mM Tris-HCl at pH 8.0, and 50 mM $CaCl_2$) and centrifuged at 2600×g for 5 minutes at 4° C. The supernatant was decanted off and pelleted protoplasts from multiple tubes were combined by resuspension in 5 mL aliquots of STC buffer. The STC buffer wash was repeated three times until protoplasts were pooled into a single 15 mL centrifuge tube. The final protoplasts pellet was resuspended in 500 μL of STC buffer and protoplast concentration was estimated with a hemocytometer. The protoplast stock was diluted to give a final concentration of $1.25\times10^8$ protoplasts per mL of STC buffer. Aliquots of protoplasts (100 μL) were used immediately for fungal transformations and excess protoplasts were preserved in 8% PEG solution (80 μL of protoplasts were added to 20 μL of 40% (w/v) PEG 4000 in STC buffer) in 1.7 mL micro-centrifuge tubes and stored at −80° C.

Fungal Protocols—Transformation of *P. paxilli*

Fungal transformations—modified from Vollmer and Yanofsky[38] and Oliver et al.[39]—were carried out in 1.7 mL micro-centrifuge tubes containing 100 μL ($1.25\times10^7$) protoplasts, either freshly prepared in STC buffer, or stored in 8% PEG solution (as described above). A solution containing 2 μL of spermidine (50 mM in H$_2$O), 5 μL heparin (5 mg/mL in STC buffer), and 5 μg of plasmid DNA (250 μg/mL) was added to the protoplasts and, following incubation on ice for 30 minutes, 900 μL of 40% PEG solution (40% (w/v) PEG 4000 in STC buffer) was added. The transformation mixture was incubated on ice for a further 15-20 minutes, transferred to 17.5 mL of 0.8% RGA medium (prewarmed to 50° C.) in sterile 50 mL tubes, mixed by inversion, and 3.5 mL aliquots were dispensed onto 1.5% RGA plates. Following overnight incubation at 25° C., 5 mL of 0.8% RGA (containing sufficient geneticin to achieve a final concentration of 150 μg per mL of solid media) was overlaid onto each plate. Plates were incubated for a further 4 days at 25° C. and spores were picked from individual colonies and streaked onto CDYE agar plates supplemented with 150 μg/mL geneticin. Streaked plates were incubated at 25° C. for a further 4 days. Spores from individual colonies were suspended in 50 μL of 0.01% (v/v) triton X-100 and 5×5 μL aliquots of the spore suspension was transferred onto new CDYE agar plates supplemented with 150 μg/mL geneticin. Sporulation plates were incubated at 25° C. for 4 days and spore stocks were prepared as follows. Colony plugs from the sporulation plates were suspended in 2 mL of 0.01% (v/v) triton X-100, and 800 μL of suspended spores were mixed with 200 μL of 50% (w/v) glycerol in a 1.7 mL micro-centrifuge tube. Spore stocks were used to inoculate 50 mL of CDYE media, flash frozen in liquid nitrogen and stored at −80° C.

Indole Diterpene Production and Extraction

Fungal transformants were grown in 50 mL of CDYE medium with trace elements for 7 days at 28° C. in shaker cultures (≥200 rpm), in 250 mL Erlenmeyer flasks capped with cotton wool. Mycelia were isolated from fermentation broths by filtration through nappy liners, transferred to 50 mL centrifuge tubes (Lab Serv®, Thermo Fisher Scientific) and indole diterpenes were extracted by vigorously shaking the mycelia (2200 rpm) in 2-butanone for ≥45 minutes.

Thin-Layer Chromatography

The 2-butanone supernatant (containing extracted indole diterpenes) was used for thin-layer chromatography (TLC) analysis on solid phase silica gel 60 aluminium plates (Merck). Indole diterpenes were chromatographed with 9:1 chloroform:acetonitrile or 8:2 dichloromethane:acetonitrile and visualized with Ehrlich's reagent (1% (w/v) p-dimethylaminobenzaldehyde in 24% (v/v) HCl and 50% ethanol).

Liquid Chromatography-Mass Spectrometry

Samples were prepared for liquid chromatography-mass spectrometry (LC-MS) from those transformants that tested positive by TLC. Accordingly, a 1 mL sample of the 2-butanone supernatant (containing extracted indole diterpenes) was transferred to a 1.7 mL micro-centrifuge tube and the 2-butanone was evaporated overnight. Contents were resuspended in 100% acetonitrile and filtered through a 0.2 μm membrane into an LC-MS vial. LC-MS samples were chromatographed on a reverse phase Thermo Scientific Accucore 2.6 μm C18 (50×2.1 mm) column attached to an UltiMate® 3000 Standard LC system (Dionex, Thermo Fisher Scientific) run at a flow rate of 0.200 mL/minute and eluted with aqueous solutions of acetonitrile containing 0.01% formic acid using a multistep gradient method (Table 14). Mass spectra were captured through in-line analysis on a maXis™ II quadrupole-time-of-flight mass spectrometer (Bruker).

Large Scale Indole Diterpene Purification for NMR Analysis

Fungal transformants that produced high levels of novel indole diterpenes were grown in ≥1 litre of CDYE medium with trace elements, as described under "Indole diterpene production and extraction". Mycelia were pooled into 1 litre Schott bottles containing stir bars. 2-butanone was added and indole diterpenes were extracted overnight with stirring (≥700 rpm). Extracts were filtered through Celite® 545 (J. T. Baker®) and dry loaded onto silica with rotary evaporation for crude purification by silica column prior to a final purification by semi-preparative HPLC. A 1 mL aliquot of crude extract was injected onto a semi-preparative reversed phase Phenomenex 5 μm C18(2) 100 Å (250×15 mm) column attached to an UltiMate® 3000 Standard LC system (Dionex, Thermo Fisher Scientific) run at a flow rate of 8.00 mL/minute. Multistep gradient methods were optimized for the purification of different sets of indole diterpenes. The purity of each indole diterpene was assessed by LC-MS and the structure was identified by NMR.

NMR

NMR samples were prepared in deuterated chloroform. Compounds were analysed by standard one-dimensional proton and carbon-13 NMR, two-dimensional correlation spectroscopy (COSY), heteronuclear single quantum correlation spectroscopy (HSQC), and heteronuclear multiple bond correlation spectroscopy (HMBC).

Tables 1-14 referenced in this specification are set out below:

TABLE 1

Functional assignment of predicted genes in the putative nodulisporic acid gene cluster.

| Gene | Size of encoded protein (aa) | Predicted function [Specific Function] | Most notable BLASTp match | | |
|---|---|---|---|---|---|
| | | | Organism | E-value % identity/% coverage | Protein name and accession number |
| nodI | 1664 | WD40 domain protein | Hypoxylon sp. CO27-5 | 0 36% ID/80% | OTA80149 |
| nodW | 608 | Cytochrome P450 oxygenase [terminal-C dioxygenase] | Aspergillus aculeatus | 9.00E−153 44% ID/97% | XP_020058732 |
| nodR* | 511 | Cytochrome P450 oxygenase | Penicillium simplicissimum | 3.00E−108 36% ID/97% | PtmU/BAU61563 |
| nodX | 593 | Cytochrome P450 oxygenase | Hypoxylon sp. | 0 62% ID/70% | OTA78491 |
| nodM* | 463 | FAD-dependent oxygenase [IDT mono-epoxidase] | Aspergillus flavus | 5.00E−173 55% ID/93% | AtmD/Q672V4 |
| nodB* | 243 | IDT cyclase [IDT cyclase] | Penicillium crustosum | 9.00E−119 68% ID/99% | PenB/AGZ20190 |
| nodO* | 448 | FAD-dependent oxygenase | Penicillium janthinellum | 2.00E−160 60% ID/97% | JanO/AGZ20488 |

TABLE 1-continued

Functional assignment of predicted genes in the putative nodulisporic acid gene cluster.

| Gene | Size of encoded protein (aa) | Predicted function [Specific Function] | Organism | E-value % identity/% coverage | Protein name and accession number |
|---|---|---|---|---|---|
| nodJ | 514 | Cytochrome P450 oxygenase | *Aspergillus clavatus* | 3.00E−148 42% ID/99% | XP_001270361 |
| nodC* | 326 | Geranylgeranyl transferase [Geranylgeranyl transferase] | *Penicillium crustosum* | 2.00E−136 66% ID/83% | PenC/AGZ20189 |
| nodY1 | 431 | FAD-dependent oxygenase | *Penicillium oxalicum* | 2.00E−71 34% ID/99% | OxaD/AOC80388 |
| nodD2* | 434 | prenyl transferase | *Penicillium janthinellum* | 1.00E−144 48% ID/96% | JanD/AGZ20478 |
| nodD1* | 431 | prenyl transferase | *Penicillium janthinellum* | 1.00E−155 53% ID/94% | JanD/AGZ20478 |
| nodY2 | 461 | FAD-dependent oxygenase | *Aspergillus alliaceus* | 3.00E−105 42% ID/98% | AspB/P0DOW1 |
| nodZ | 477 | Cytochrome P450 oxygenase | *Penicillium flavigenum* | 7.00E−166 48% ID/96% | OQE14847 |
| nodS | 535 | Not stated | *Hypoxylon* sp. CO27-5 | 9.00E−139 46% ID/94% | OTA93952 |

Naming of genes in IDT clusters has followed the A. nidulans naming convention where genes are given a name with a with a three letter prefix in lower case that designates species, followed by a single letter suffix in upper case that designates gene function written in italic font (e.g. paxC). Naming of the corresponding protein product follows the same rules except that the initial letter of the prefix is upper case and the entire name is written in normal (non-italic) font (e.g. PaxC is the protein product of paxC). Thus, a nod name was assigned to each *H. pulicicidum* gene in the NAA 10 gene cluster. *H. pulicicidum* genes that share homology (>35% amino acid identity of predicted translational products) with genes found in known IDT pathways are followed by an asterisk (*) and, with the exception of nodR, were given letters corresponding to known confirmed genes (e.g. the protein encoded by nodC shares 52.8% amino acid identity with the protein product of paxC). The genes that do not share homology with known IDT genes were assigned letters that are not shared with any of the confirmed IDT genes. Notably, the cluster contains two sets of paralogous genes (share >40% amino acid identity with each other), which we have distinguished using numbers (i.e. nodD1/nodD2 and nodY1/nodY2). Closest matches were identified using BLASTp (protein-protein BLAST) against the non-redundant protein sequence database with 'expect threshold' set at 10 and 'word size' set at 6. The BLOSUM62 scoring matrix was applied with a gap opening penalty of 11 and a gap extension penalty of 1 with conditional compositional score matrix adjustment.

TABLE 2

Similarity matrix of geranylgeranyl transferases ('C' enzymes).

| Enzyme | PaxC | NodC | LtmC | AtmC | JanC | PenC |
|---|---|---|---|---|---|---|
| PaxC | 100 | *52.3* | *35.3* | *54.3* | *70.9* | *60.5* |
| NodC | 66.7 | 100 | *38.8* | *55.1* | *55.4* | *54.4* |
| LtmC | 54 | 61.7 | 100 | *40.2* | *36.4* | *39.5* |
| AtmC | 69.9 | 70.5 | 61.5 | 100 | *58.3* | *63.6* |
| JanC | 79.5 | 70.3 | 55.5 | 74.1 | 100 | *66.7* |
| PenC | 73.4 | 70.5 | 59.1 | 78 | 79.2 | 100 |

Numbers in italics represent % identity scores. Numbers in bold represent % similarity scores for amino acid residues.

TABLE 3

Similarity matrix of 3-gernaylkgeranylindole epoxidases ('M' enzymes).

| Enzyme | LtmM | NodM | AtmM | PenM | JanM | PaxM |
|---|---|---|---|---|---|---|
| LtmM | 100 | *37.3* | *38.2* | *36.8* | *36.9* | *37.9* |
| NodM | 57.2 | 100 | *48.3* | *51.2* | *52.9* | *48.6* |
| AtmM | 56.3 | 63.4 | 100 | *48.3* | *47.9* | *48.9* |
| PenM | 54.8 | 66 | 62.8 | 100 | *61.6* | *60.6* |
| JanM | 54.7 | 67 | 61.6 | 75.1 | 100 | *66.7* |
| PaxM | 56.6 | 65.8 | 64.4 | 74 | 79.9 | 100 |

Numbers in italics represent % identity scores and numbers in bold represent % similarity scores for amino acid residues.

TABLE 4

Similarity matrix of indole diterpene cyclases ('B' enzymes).

| Enzyme | PaxB | NodB | LtmB | AtmB | JanB | PenB |
|---|---|---|---|---|---|---|
| PaxB | 100 | *63* | *49.6* | *62.1* | *77* | *72.4* |
| NodB | 78.2 | 100 | *48.8* | *64.2* | *65.4* | *67.9* |
| LtmB | 65.6 | 63.5 | 100 | *48.8* | *51.6* | *52* |
| AtmB | 77 | 78.2 | 65.2 | 100 | *67.5* | *70.8* |
| JanB | 87.2 | 77.8 | 66.4 | 79.8 | 100 | *78.2* |
| PenB | 87.7 | 80.2 | 66.4 | 82.3 | 86.4 | 100 |

Numbers in italics represent % identity scores and numbers in bold represent % similarity scores for amino acid residues.

TABLE 5

Similarity matrix of indole diterpene prenyl transferases ('D' and 'E' enzymes compared to NodD1 and NodD2).

| Enzyme | NodD2 | PaxD | NodD1 | JanD | AtmD | LtmE | PenD | PenE |
|---|---|---|---|---|---|---|---|---|
| NodD2 | 100 | *42.3* | *44.7* | *45* | *31.6* | *11.3* | *32.6* | *23.3* |
| PaxD | 61.9 | 100 | *44.9* | *65.8* | *31.3* | *11.4* | *31.4* | *24.3* |
| NodD1 | 60.7 | 63.6 | 100 | *49.2* | *29.2* | *11.2* | *29.7* | *22.7* |
| JanD | 63.1 | 80.6 | 65.6 | 100 | *30.5* | *11.7* | *31.9* | *25.2* |
| AtmD | 49.6 | 49.4 | 47.6 | 50.2 | 100 | *11.2* | *28.6* | *25.2* |
| LtmE | 20 | 20.7 | 21 | 21.6 | 19.5 | 100 | *10.8* | *11.6* |
| PenD | 54.4 | 53.5 | 50.7 | 51.9 | 48.1 | 20.9 | 100 | *24.3* |
| PenE | 41.1 | 40.5 | 40.2 | 41.3 | 37.4 | 21.7 | 41.3 | 100 |

Numbers in italics represent % identity scores and bold numbers represent % similarity scores for amino acid residues.

TABLE 6

Similarity matrix of indole diterpene FAD dependent oxidative cyclases ('O' enzymes).

| Enzyme | PenO | JanO | NodO | PaxO |
|---|---|---|---|---|
| PenO | 100 | *42.9* | *44.9* | *40.3* |
| JanO | 59.3 | 100 | *50.7* | *71.9* |
| NodO | 61.9 | 69.2 | 100 | *48.7* |
| PaxO | 56.9 | 84 | 67 | 100 |

Numbers in italics represent % identity scores and numbers in bold represent % similarity scores for amino acid residues.

TABLE 7

Table of fungal species used in this study.

| *Hypoxylon pulicicidum* (*Nodulisporium* sp.) strain | Description | Indole diterpene phenotype Nodulisporic acid A | Source [reference(s)] |
|---|---|---|---|
| ATCC ® 74245 ™ | Wild type | + | ATCC [25] |

| *Penicillium paxilli* strain | Description | Indole diterpene phenotype Paspaline | Paxilline | Source [reference(s)] |
|---|---|---|---|---|
| PN2013 (ATCC ®26601 ™) | Wild type | + | + | Barry Scott, Massey University [24] |
| PN2250 (CY2) | PN2013/Deletion of entire PAX locus (ΔPAX); Hyg$^R$ | − | − | Barry Scott, Massey University [15] |
| PN2257 | PN2013/ΔpaxM::P$_{glcA}$-hph-T$_{trpC}$; Hyg$^R$ | − | − | Barry Scott, Massey University [15] |
| PN2290 | PN2013/ΔpaxC::P$_{trpC}$-hph; Hyg$^R$ | − | − | Barry Scott, Massey University [28] |

TABLE 8

PCR primers for amplification of transcription unit modules (TUMs).

| TUM | Primer name | Primer sequence (5' to 3') |
|---|---|---|
| | | *Hypoxylon pulicicidum* primers |
| | | nodW |
| nodW$_{CDS}$ | P4502 frag 1 F | cgatgtacgtctca*CTCG* AATG actttagctattttaggcatcagttgcc (SEQ ID NO: 57) |
| | P4502 frag 1 R | actgctcgtctca*ACT*Cccgctgcgagccgct (SEQ ID NO: 58) |
| | P4502 frag 2 F | acgtaccgtctccGAGTccggtcctggtggagtgatc (SEQ ID NO: 59) |
| | P4502 frag 2 R | gaccttcgtctctGTCTca AAGC ctaagttatgcccagatatttccag (SEQ ID NO: 60) |
| | | nodM |
| nodM$_{CDS}$ | nodM frag1 F | cgatgtacgtctca*CTCG*AATGtctacccctgagttcaagg (SEQ ID NO: 61) |
| | nodM frag1 R | cagtcacgtctcaACGCctctcaagaacgatgtgggaaattc (SEQ ID NO: 62) |
| | nodM frag2 F | gtgcatcgtctcaGCGTagtgtaatcgcaccagag (SEQ ID NO: 63) |
| | nodM frag2 R | gaccttcgtctctGTCTca AAGC ctatgaagcgatgtctctaatatggagtaac (SEQ ID NO: 64) |
| | | nodB |
| nodB$_{CDS}$ | nodB F | cgatgtacgtctca*CTCG*AATGgatggattcgatcgttccaatg (SEQ ID NO: 65) |
| | nodB R | gaccttcgtctctGTCTca AAGC ttattgagccttccgcgcattg (SEQ ID NO: 66) |
| | | nodC |
| nodC$_{CDS}$ | nodC frag1 F | cgatgtacgtctca*CTCG*AATGtccttaggtttacagtgcttgg (SEQ ID NO: 67) |
| | nodC frag1 R | cattgacgtctcgGTCAcgtcgccaaaccagcga (SEQ ID NO: 68) |

TABLE 8 -continued

PCR primers for amplification of transcription unit modules (TUMs).

| TUM | Primer name | Primer sequence (5' to 3') |
|---|---|---|
| | nodC frag2 F | gtcacgcgtctctTGACggcctcactagctttcc<br>(SEQ ID NO: 69) |
| | nodC frag2 R | gaccttcgtctctGTCTca AAGC tcaatgcgtaagatcgagtttctcctttct<br>(SEQ ID NO: 70) |

Penicillium paxilli primers paxG

| | | |
|---|---|---|
| paxG$_{ProUTR}$ | PpaxG F | cgatgtacgtctcaCTCGGGAGattcacgacctgtgactagtcaa<br>(SEQ ID NO: 71) |
| | PpaxG R | gaccttcgtctctGTCTca CATT ggcgtcgaacttgatgaagttttc<br>(SEQ ID NO: 72) |
| paxG$_{CDS}$ | paxG frag1 F | cgatgtacgtctcaCTCGAATGtcctacatccttgcagaag<br>(SEQ ID NO: 73) |
| | paxG frag1 R | cttctacgtctcgTACTgttctaatcgtgcttggtg<br>(SEQ ID NO: 74) |
| | paxG frag2 F | gcacgacgtctccAGTAcaggtgctagaagatgacgttgac<br>(SEQ ID NO: 75) |
| | paxG frag2 R | aggcgccgtctccACCAatctctttcaatcttgcttgttgga<br>(SEQ ID NO: 76) |
| | paxG frag3 F | gattgacgtctctTGGTgaccccgcgcctt<br>(SEQ ID NO: 77) |
| | paxG frag3 R | gtcgaccgtctctTTCCctagtatattggaagctcccg<br>(SEQ ID NO: 78) |
| | paxG frag4 F | tccaatcgtctcgGGAAaccctaagtcgacttagtgcg<br>(SEQ ID NO: 79) |
| | paxG frag4 R | gaccttcgtctctGTCTca AAGC ttaaactcttcctttctcattagtaggg<br>(SEQ ID NO: 80) |
| PaXG$_{UTRterm}$ | TpaxG F | cgatgtacgtctcaCTCGGCTTtcaatcgtgctgcatttctctt<br>(SEQ ID NO: 81) |
| | TpaxG R | gaccttcgtctctGTCTca AGCG tcactcccgagcaatattgct<br>(SEQ ID NO: 82) | paxC

| | | |
|---|---|---|
| paxC$_{ProUTR}$ | PpaxC F2 | cgatgtacgtctcaCTCGGGAGacaacaaaaagatcagccaatgg<br>(SEQ ID NO: 83) |
| | PpaxC R2 | gaccttcgtctctGTCTca CATT aaaatgggacctacaccctgaa<br>(SEQ ID NO: 84) |
| paxC$_{CDS}$ | paxC frag1 F | cgatgtacgtctcaCTCGAATGggcgtagcaggga<br>(SEQ ID NO: 85) |
| | paxC frag1 R | cattgacgtctccACGGcgccagacaaggga<br>(SEQ ID NO: 86) |
| | paxC frag2 F | cccttgcgtctcgCCGTgacggagtcaatgggttc<br>(SEQ ID NO: 87) |
| | paxC frag2 R | gaccttcgtctctGTCTca AAGC tcatgccttcaggtcaagcttc<br>(SEQ ID NO: 88) |
| paxC$_{UTRterm}$ | TpaxC F | cgatgtacgtctcaCTCGGCTTttggccttgtgaaatatgggactac<br>(SEQ ID NO: 89) |
| | TpaxC R | gaccttcgtctctGTCTca AGCG atctctgtcatgtcggatatcagat<br>(SEQ ID NO: 90) | paxM

| | | |
|---|---|---|
| paxM$_{ProUTR}$ | PpaxM F | cgatgtacgtctcaCTCGGGAGgttgttggcatgggagtaggat<br>(SEQ ID NO: 91) |
| | PpaxM R | gaccttcgtctctGTCTca CATT ggtttctgaatcttaaagatacatgaaaag<br>(SEQ ID NO: 92) |
| paxM$_{CDS}$ | paxM frag1 F | cgatgtacgtctcaCTCGAATGgaaaaggccgagtttcaag<br>(SEQ ID NO: 93) |
| | paxM frag1 R | tgacaacgtctcgTCCAtcgaataaagcgttgacttgc<br>(SEQ ID NO: 94) |
| | paxM frag2 F | acgcttcgtctcaTGGActcactattgtcacaatccatggaaaag<br>(SEQ ID NO: 95) |
| | paxM frag2 R | gaccttcgtctctGTCTca AAGC ttaaacttgaagaaaataaaacttcag<br>ggcac<br>(SEQ ID NO: 96) |
| paxM$_{UTRterm}$ | TpaxM frag1 F | cgatgtacgtctcaCTCGGCTTaccattggagcaattttggttttc<br>(SEQ ID NO: 97) |
| | TpaxM frag1 R | gttcgccgtctcgACTCgattgcttgtgggtct<br>(SEQ ID NO: 98) |
| | TpaxM frag2 F | acaagccgtctccGAGTccagccagcgaacttg<br>(SEQ ID NO: 99) |
| | TpaxM frag2 R | gaccttcgtctctGTCTca AGCG ttttggcttacttcagtttaactgttttg<br>(SEQ ID NO: 100) |

TABLE 8 -continued

PCR primers for amplification of transcription unit modules (TUMs).

| TUM | Primer name | Primer sequence (5' to 3') |
|---|---|---|
| paxB | | |
| paxB$_{ProUTR}$ | PpaxB F | cgatgtacgtctca*CTCGGGAG*aaggctgtgttggagagaatc (SEQ ID NO: 101) |
| | PpaxB R | gacctttcgtctct*GTCT*ca CATT agtttctaaggttgacgtgggaaaaag (SEQ ID NO: 102) |
| paxB$_{CDS}$ | paxB F | cgatgtacgtctca*CTCGAATG*gacggttttgatgtttcccaa (SEQ ID NO: 103) |
| | paxB R | gacctttcgtctct*GTCT*ca AAGC tcaatttgcttttttcggcccgcttatgc (SEQ ID NO: 104) |
| paxB$_{UTRterm}$ | TpaxB F | cgatgtacgtctca*CTCGGCTT*tcggcagttgagggtgaaac (SEQ ID NO: 105) |
| | TpaxB R | gacctttcgtctct*GTCT*ca AGCG ggttaacaatgaggaacgatgaacag (SEQ ID NO: 106) |
| Additional primers | | |
| trpC | | |
| trpC$_{ProUTR}$ | PtrpC frag1 F | cgatgtacgtctca*CTCGGGAG*gaattcatgccagttgttcccag (SEQ ID NO: 107) |
| | PtrpC frag1 R | cgatgtacgtctca GCTT ggccgactcgctg (SEQ ID NO: 108) |
| | PtrpC frag2 F | cacctttcgtctcc AAGC agacgtgaagcaggacgg (SEQ ID NO: 109) |
| | PtrpC frag2 R | cgatgtcgtctcg*CAG*Accattgcacaagcctc (SEQ ID NO: 110) |
| | PtrpC frag3 F | gacctttcgtctcg*TCTG*cgcatggatcgctgc (SEQ ID NO: 111) |
| | PtrpC frag3 R | gacctttcgtctct*GTCT*ca CATT atcgatgcttgggtagaataggtaag (SEQ ID NO: 112) |
| trpC$_{UTRterm}$ | T trpC frag1 F | cgatgtacgtctca*CTCGGCTT*gatccacttaacgttactgaaatcatcaaac (SEQ ID NO: 113) |
| | T trpC frag1 R | gacctttcgtctct*CTGC*ttgatctcgtctgccga (SEQ ID NO: 114) |
| | T trpC frag2 F | cgatgtacgtctca*GCAG*atcaacggtcgtcaaga (SEQ ID NO: 115) |
| | T trpC frag2 R | gacctttcgtctct*GTCT*ca AGCG tctagaaagaaggattacctctaaac aagtgt (SEQ ID NO: 116) |
| nptII | | |
| nptII$_{CDS}$ | ntpII F | cgatgtacgtctca*CTCGAATG*attgaacaagatggattgcacg (SEQ ID NO: 117) |
| | ntpII R | gacctttcgtctct*GTCT*ca AAGC ctcagaagaactcgtcaagaaggc (SEQ ID NO: 118) |

The forward and reverse PCR primers used for amplification of TUMs (i.e. promoters (ProUTR), coding sequences (CDSs), and terminators (UTRterm)) are listed. Primers used to amplify TUM fragments for domestication purposes (i.e. removal of internal sites for AarI, BsaI or BsmBI) are underlined (e.g., P4502 frag 1 R). The template for amplification of nod CDSs was genomic DNA from *Hypoxylon pulicicidum* strain ATCC® 74245™.[25] The template for amplification of pax gene TUMs was genomic DNA from *Penicillium paxilli* strain ATCC® 26601™ (PN2013).[24] The PCR products used to produce the trpC ProUTR module, nptII CDS module (conferring resistance to geneticin), and trpC$_{UTRterm}$ module were all amplified from plasmid pII99.[41] The BsmBI recognition sites are shown in bold lower case text (cgtctc), with the overhangs generated following BsmBI cleavage shown by the upper case italics text. The 5' (prefix) and 3' (suffix) nucleotide bases, which flank each TUM and form the basis of the address system for each of the MIDAS modules, are shown in bold upper case text, and bold upper case italic text respectively.

TABLE 9

MIDAS Level-1 plasmid library:
Assembly of TUMs in pML1.
[GGAG] [AATG] [GCTT] [CGCT]

| Plasmid name | Description |
|---|---|
| ProUTR modules | |
| pSK1 | paxG$_{ProUTR}$ |
| pKV28 | paxC$_{ProUTR}$ |
| pSK4 | PaxM$_{ProUTR}$ |
| pSK7 | paxB$_{ProUTR}$ |
| pSK17 | trpC$_{ProUTR}$ |
| CDS modules | |
| pKV45 | nodW$_{CDS}$ |
| pKV59 | nodM$_{CDS}$ |
| pSK18 | |
| pSK19 | nodB$_{CDS}$ |
| pSK20 | nodC$_{CDS}$ |
| pSK2 | paxG$_{CDS}$ |
| pSK11 | paxC$_{CDS}$ |

TABLE 9-continued

MIDAS Level-1 plasmid library: Assembly of TUMs in pML1. [GGAG] [AATG] [GCTT] [CGCT]

| Plasmid name | Description |
|---|---|
| pSK5 | paxM$_{CDS}$ |
| pSK16 | nptII$_{CDS}$ |
| *UTRterm modules* | |
| pSK3 | paxG$_{UTRterm}$ |
| pSK12 | paxC$_{UTRterm}$ |
| pSK6 | paxM$_{UTRterm}$ |
| pSK9 | paxB$_{UTRterm}$ |
| pSK15 | trpC$_{UTRterm}$ |

This table represents the MIDAS level-1 TUMs that we used to assemble MIDAS level-2 TUs (Table 10). The 4 base prefixes and suffixes (5' to 3') that flank each TUM are shown at the top of the table to highlight the sequences used to bind the TUMs together to make MIDAS level-2 TUs. These 4 base flanking regions are depicted in the primer table (Table 8) in bold upper case text (forward addresses) and bold upper case italics text (reverse addresses).

TABLE 10

MIDAS Level-2 plasmid library: Assembly of TUs in pML2 destination vectors

| TU | Level-1 entry clones used for TU assembly | | | pML2 destination vector | Level-2 entry clones | |
|---|---|---|---|---|---|---|
| | ProUTR | CDS | UTRterm | | Name | Description |
| nodW | pSK17 | pKV45 | pSK15 | pML2(+)WR | pKV52 | ◀ (T$_{trpC}$-nodW-P$_{trpC}$):pML2(+)WR |
| | | | | pML2(+)BR | pSK67 | ◀ (T$_{trpC}$-nodW-P$_{trpC}$):pML2(+)BR |
| nodM | pSK4 | pKV59 | pSK6 | pML2(+)BF | pKV57 | (P$_{trpC}$-nodM-T$_{trpC}$) ▶ :pML2(+)BF |
| | | | pSK18 | pML2(+)WF | pSK28 | (P$_{trpC}$-nodM-T$_{trpC}$) ▶ :pML2(+)WF |
| nodB | pSK7 | pSK19 | pSK9 | pML2(+)BR | pSK29 | ◀ (T$_{trpC}$-nodB-P$_{trpC}$):pML2(+)BR |
| nodC | pSK17 | pSK20 | pSK15 | pML2(+)BF | pKV26 | (P$_{trpC}$-nodC-T$_{trpC}$) ▶ :pML2(+)BF |
| | pKV28 | | pSK12 | pML2(+)WF | pSK60 | (P$_{trpC}$-nodC-T$_{trpC}$) ▶ :pML2(+)WF |
| paxG | pSK1 | pSK2 | pSK3 | pML2(+)BR | pSK21 | ◀ (T$_{paxG}$-paxG-P$_{paxG}$):pML2(+)BR |
| paxC | pKV28 | pSK11 | pSK12 | pML2(+)WF | pSK59 | (P$_{paxC}$-paxC-T$_{paxC}$) ▶ :pML2(+)WF |
| paxM | pSK4 | pSK5 | pSK6 | pML2(+)WR | pSK22 | ◀ (T$_{paxM}$-paxM-P$_{paxM}$):pML2(+)WR |
| nptII | pSK17 | pSK16 | pSK15 | pML2(+)WF | pSK26 | (P$_{trpC}$-nptII-T$_{trpC}$) ▶ :pML2(+)WF |

This table represents the construction of the MIDAS level-2 This that were used to assemble MIDAS level-3 multi-gene plasmids for heterologous expression studies. The names of the Level-2 entry plasmids produced are shown in bold. This are described by the CDS they contain and TU orientation, determined by the pML2 destination vector, is shown by the arrowhead (▶ for forward (F) destination vector and ◀ for reverse (R) destination vector) in the Level-2 description.

TABLE 11

MIDAS Level-3 plasmid library: Multi-gene assemblies in pML3

| Step | Level-2 entry clone | | Destination vector | Golden Gate reaction | Product Level-3 plasmid | | Plasmid size (kb) |
|---|---|---|---|---|---|---|---|
| | Name | Description | | | Name | Description | |
| 1 | pSK26 | (P$_{trpC}$-nptII-T$_{trpC}$) ▶ :pML2(+)WF | pML3 | AarI | pKV22 | pML3:nptII ▶ | 5.6 |
| 2 | pKV26 | (P$_{trpC}$-nodC-T$_{trpC}$) ▶ :pML2(+)BF | pKV22 | BsmBI | pKV27 | pML3:nptII ▶ :nodC ▶ | 9.0 |
| 2 | pKV57 | (P$_{trpC}$-nodM-T$_{trpC}$) ▶ :pML2(+)BF | pKV22 | BsmBI | pKV63 | pML3:nptII ▶ :nodM ▶ | 9.4 |
| 3 | pKV52 | ◀ (T$_{trpC}$-nodW-P$_{trpC}$):pML2(+)WR | pKV63 | AarI | pKV64 | pML3:nptII ▶ :nodM ▶ : ◀ nodW | 13.0 |
| 1 | pSK26 | (P$_{trpC}$-nptII-T$_{trpC}$) ▶ :pML2(+)WF | pML3 | AarI | pSK33 | pML3:nptII ▶ | 5.6 |
| 2 | pSK21 | ◀ (T$_{paxG}$-paxG-P$_{paxG}$):pML2(+)BR | pSK33 | BsmBI | pSK34 | pML3:nptII ▶ : ◀ paxG | 8.2 |
| 3 | pSK22 | ◀ (T$_{paxM}$-paxM-P$_{paxM}$):pML2(+)WR | pSK34 | AarI | pSK36 | pML3:nptII ▶ : ◀ paxG: ◀ paxM | 11.5 |

TABLE 11-continued

MIDAS Level-3 plasmid library: Multi-gene assemblies in pML3

| Step | Level-2 entry clone Name | Description | Destination vector | Golden Gate reaction | Product Level-3 plasmid Name | Description | Plasmid size (kb) |
|---|---|---|---|---|---|---|---|
| 4 | pSK29 | ◀(T$_{trpC}$-nodB-P$_{trpC}$):pML2(+)BR | pSK36 | BsmBI | pKV73 | pML3:nptII ▶:◀paxG:◀paxM:◀nodB | 14.1 |
| 5 | pSK59 | (P$_{paxC}$-paxC-T$_{paxC}$)▶:pML2(+)WF | pSK73 | AarI | pKV74 | pML3:nptII ▶:◀paxG:◀paxM:◀nodB:paxC▶ | 16.3 |
| 3 | pSK28 | (P$_{trpC}$-nodM-T$_{trpC}$)▶:pML2(+)WF | pSK34 | AarI | pSK35 | pML3:nptII ▶:◀paxG:nodM▶ | 11.5 |
| 4 | pSK29 | ◀(T$_{trpC}$-nodB-P$_{trpC}$):pML2(+)BR | pSK35 | BsmBI | pSK38 | pML3:nptII ▶:◀paxG:nodM▶:◀nodB | 14.1 |
| 5 | pSK60 | (P$_{trpC}$-nodC-TtrpC)▶:pML2(+)WF | pSK38 | AarI | pSK66 | pML3:nptII ▶:◀paxG:nodM▶:◀nodB:nobC▶ | 16.3 |
| 6 | pSK67 | ◀(T$_{trpC}$-nodW-P$_{trpC}$):pML2(+)BR | pSK66 | BsmBI | pSK68 | pML3:nptII ▶:◀paxG:nodM▶:◀nodB:nobC▶:◀nodW | 20.5 |

The table shows the Level-2 entry clone and Level-3 destination vectors used to construct the multi-gene plasmids. The names of the plasmids produced during each cycle of Level-3 assembly are shown in bold. The number of level 3 assembly reactions used to create the level-3 plasmid is indicated by number in the step column. TUs are annotated with the name of the CDS they contain. TU orientation is shown by the arrowhead.

Generalised features of forward and reverse PCR primers used for amplification of TUMs are listed. The BsmBI recognition sites are shown in lower case bold (cgtctc), with the overhangs generated following BsmBI cleavage shown by upper case italics (e.g., CTCG). The 5' and 3' nucleotide-specific bases, which flank each TUM and form the basis of the address system for each of the MIDAS modules, are shown in upper case bold (e.g., GGAG) and upper case bold italics (e.g., CATT), respectively.

TABLE 12

Generalised primer design for amplification of ProUTR, CDS and UTRterm modules to be cloned into pML1.

| TUM | Primer | Primer sequence (5' to 3') |
|---|---|---|
| [GGAG]-ProUTR-[AATG] | Forward | 5'-cgatgtacgtctcaCTCGGGAG (SEQ ID NO: 119) (+18-25 bases specific for the 5' end of the promoter)-3' |
|  | Reverse | 5'-gacctttcgtctctGTCTca CATT (SEQ ID NO: 120) (+18-25 bases specific for the 3' end of the 5'UTR)-3' The CAT sequence (reverse-complement = ATG) underlined within the CATT module-specific nucleotides, specifies the translation initiation codon for the CDS of interest, while the final T (not underlined) represents the base immediately upstream of the initiation codon. |
| [AATG]-CDS-[GCTT] | Forward | 5'-cgatgtacgtctcaCTCGAATG (SEQ ID NO: 121) (+18-25 bases specific for the 5' end of the CDS, beginning at the 2$^{nd}$ codon)-3' The ATG sequence (underlined within the AATG module-specific nucleotides) specifies the translation initiation codon for the CDS of interest, while the initial A (not underlined) represents the base immediately upstream of the initiation codon. |
|  | Reverse | 5'-gacctttcgtctctGTCTca AAGC* (SEQ ID NO: 122) (+18-25 bases specific for the 3' end of the CDS)-3' Remember to include a stop codon (*) at the end of the CDS. |
| [GCTT]-UTRterm-[CGCT] | Forward | 5'-cgatgtacgtctcaCTCGGCTT (SEQ ID NO: 123) (+18-25 bases specific for the 5' end of the 3'UTR)-3' |
|  | Reverse | 5'-gacctttcgtctctGTCTca AGCG (SEQ ID NO: 124) (+18-25 bases specific for the 3' end of the terminator)-3' |

TABLE 13

Level-3 multigene assemblies are constructed by alternating Golden Gate cloning reactions using TUs assembled in "White" and "Blue" pML2 vectors.

| Step | Level-2 entry clone | Destination plasmid | Golden Gate reaction | Product plasmid | Screen |
|---|---|---|---|---|---|
| 1 | TU1 in a White pML2 vector | pML3 | AarI-mediated | pML3:TU1 | White colonies |
| 2 | TU2 in a Blue pML2 vector | pML3:TU1 | BsmBI-mediated | pML3:TU1:TU2 | Blue colonies |
| 3 | TU3 in a White pML2 vector | pML3:TU1:TU2 | AarI-mediated | pML3:TU1:TU2:TU3 | White colonies |
| 4 | TU4 in a Blue pML2 vector | pML3:TU1:TU2:TU3 | BsmBI-mediated | pML3:TU1:TU2:TU3:TU4 | Blue colonies |

The table shows the cloning steps used to produce a hypothetical multigene construct containing four TUs, with each row depicting the input plasmids (Level-2 entry clone and destination plasmid), the type of Golden Gate reaction used for assembly, the product plasmid and the type of colonies screened.

TABLE 14

Multistep acetonitrile gradient used for LC-MS analysis of fungal extracts.

| Time (minutes) | % (v/v) of acetonitrile + 0.01% (v/v) formic acid |
|---|---|
| 0 | 50 |
| 1 | 50 |
| 15 | 70 |
| 20 | 95 |
| 25 | 95 |
| 28 | 50 |
| 38 | 50 |

INDUSTRIAL APPLICATION

The invention has industrial application in the production of indole diterpene compounds, particularly NAs.

REFERENCES (1) Ogata, M.; Ueda, J.; Hoshi, M.; Hashimoto, J.; Nakashima, T.; Anzai, K.; Takagi, M.; Shin-ya, K. *J. Antibiot.* (Tokyo) 2007, 60 (10), 645-648.
(2) Nakazawa, J.; Yajima, J.; Usui, T.; Ueki, M.; Takatsuki, A.; Imoto, M.; Toyoshima, Y. Y.; Osada, H. *Chem. Biol.* 2003, 10 (2), 131-137.
(3) Sallam, A. A.; Ayoub, N. M.; Foudah, A.; Gissendanner, C. R.; Meyer, S. A.; El Sayed, K. A. *Eur. J. Med. Chem.* 2013, 70, 594-606.
(4) Fan, Y.; Wang, Y.; Liu, P.; Fu, P.; Zhu, T.; Wang, W.; Zhu, W. *J. Nat. Prod.* 2013, 76 (7), 1328-1336.
(5) Meinke, P. T.; Smith, M. M.; Shoop, W. L. *Curr. Top. Med. Chem.* 2002, 2 (7), 655-674.
(6) Knaus, H.-G.; McManus, O. B.; Lee, S. H.; Schmalhofer, W. A.; Garcia-Calvo, M.; Helms, L. M. H.; Sanchez, M.; Giangiacomo, K.; Reuben, J. P. *Biochemistry (Mosc.)* 1994, 33 (19), 5819-5828.
(7) Bills, G. F.; González-Menéndez, V.; Martin, J.; Platas, G.; Fournier, J.; Peršoh, D.; Stadler, M. *PLOS ONE* 2012, 7 (10), e46687.
(8) Shoop, W. L.; Gregory, L. M.; Zakson-Aiken, M.; Michael, B. F.; Haines, H. W.; Ondeyka, J. G.; Meinke, P. T.; Schmatz, D. M. *J. Parasitol.* 2001, 87 (2), 419-423.
(9) Byrne, K. M.; Smith, S. K.; Ondeyka, J. G. *J. Am. Chem. Soc.* 2002, 124 (24), 7055-7060.
(10) Smith, A. B.; Davulcu, A. H.; Cho, Y. S.; Ohmoto, K.; Kürti, L.; Ishiyama, H. *J. Org. Chem.* 2007, 72 (13), 4596-4610.
(11) Zou, Y.; Melvin, J. E.; Gonzales, S. S.; Spafford, M. J.; Smith, A. B. *J. Am. Chem. Soc.* 2015, 137 (22), 7095-7098.
(12) Melvin, J. E. *Diss. Available ProQuest* 2014, 1-273.
(13) Young, C.; McMillan, L.; Telfer, E.; Scott, B. *Mol. Microbiol.* 2001, 39 (3), 754-764.
(14) Saikia, S.; Parker, E. J.; Koulman, A.; Scott, B. *J. Biol. Chem.* 2007, 282 (23), 16829-16837.
(15) Scott, B.; Young, C. A.; Saikia, S.; McMillan, L. K.; Monahan, B. J.; Koulman, A.; Astin, J.; Eaton, C. J.; Bryant, A.; Wrenn, R. E.; Finch, S. C.; Tapper, B. A.; Parker, E. J.; Jameson, G. B. *Toxins* 2013, 5 (8), 1422-1446.
(16) Tagami, K.; Liu, C.; Minami, A.; Noike, M.; Isaka, T.; Fueki, S.; Shichijo, Y.; Toshima, H.; Gomi, K.; Dairi, T.; Oikawa, H. *J. Am. Chem. Soc.* 2013, 135 (4), 1260-1263.
(17) Motoyama, T.; Hayashi, T.; Hirota, H.; Ueki, M.; Osada, H. *Chem. Biol.* 2012, 19 (12), 1611-1619.
(18) Saikia, S.; Takemoto, D.; Tapper, B. A.; Lane, G. A.; Fraser, K.; Scott, B. *FEBS Lett.* 2012, 586 (16), 2563-2569.
(19) Tagami, K.; Minami, A.; Fujii, R.; Liu, C.; Tanaka, M.; Gomi, K.; Dairi, T.; Oikawa, H. *ChemBioChem* 2014, 15 (14), 2076-2080.
(20) Liu, C.; Tagami, K.; Minami, A.; Matsumoto, T.; Frisvad, J. C.; Suzuki, H.; Ishikawa, J.; Gomi, K.; Oikawa, H. *Angew. Chem. Int. Ed.* 2015, 54 (19), 5748-5752.
(21) Tang, M.-C.; Lin, H.-C.; Li, D.; Zou, Y.; Li, J.; Xu, W.; Cacho, R. A.; Hillenmeyer, M. E.; Garg, N. K.; Tang, Y. *J. Am. Chem. Soc.* 2015, 137 (43), 13724-13727.
(22) Liu, C.; Minami, A.; Dairi, T.; Gomi, K.; Scott, B.; Oikawa, H. *Org. Lett.* 2016, 18 (19), 5026-5029.
(23) Saikia, S.; Scott, B. *Mol. Genet. Genomics* 2009, 282 (3), 257-271.
(24) Itoh, Y.; Johnson, R.; Scott, B. *Curr. Genet.* 1994, 25 (6), 508-513.
(25) Dombrowski, A. W.; Endris, R. G.; Helms, G. L.; Hensens, O. D.; Ondeyka, J. G.; Ostlind, D. A.; Polishook, J. D.; Zink, D. L. U.S. Pat. No. 5,399,582—Antiparasitic agents. 5399582, Mar. 21, 1995.
(26) Byrd, A. D.; Schardl, C. L.; Songlin, P. J.; Mogen, K. L.; Siegel, M. R. *Curr. Genet.* 1990, 18 (4), 347-354.
(27) Engler, C.; Kandzia, R.; Marillonnet, S. *PLOS ONE* 2008, 3 (11), e3647.
(28) Sarrion-Perdigones, A.; Falconi, E. E.; Zandalinas, S. I.; Juárez, P.; Fernández-del-Carmen, A.; Granell, A.; Orzaez, D. *PLOS ONE* 2011, 6 (7), e21622.

(29) Sarrion-Perdigones, A.; Vazquez-Vilar, M.; Palací, J.; Castelijns, B.; Forment, J.; Ziarsolo, P.; Blanca, J.; Granell, A.; Orzaez, D. *Plant Physiol.* 2013, 162 (3), 1618-1631.
(30) De Paoli, H. C.; Tuskan, G. A.; Yang, X. *Sci. Rep.* 2016, 6.
(31) Weber, E.; Engler, C.; Gruetzner, R.; Werner, S.; Marillonnet, S. *PLOS ONE* 2011, 6 (2), e16765.
(32) Binder, A.; Lambert, J.; Morbitzer, R.; Popp, C.; Ott, T.; Lahaye, T.; Parniske, M. *PLOS ONE* 2014, 9 (2), e88218.
(33) Patron, N. J.; Orzaez, D.; Marillonnet, S.; Warzecha, H.; Matthewman, C.; Youles, M.; Raitskin, O.; Leveau, A.; Farré, G.; Rogers, C.; Smith, A.; Hibberd, J.; Webb, A. A. R.; Locke, J.; Schomack, S.; Ajioka, J.; Baulcombe, D. C.; Zipfel, C.; Kamoun, S.; Jones, J. D. G.; Kuhn, H.; Robatzek, S.; Van Esse, H. P.; Sanders, D.; Oldroyd, G.; Martin, C.; Field, R.; O'Connor, S.; Fox, S.; Wulff, B.; Miller, B.; Breakspear, A.; Radhakrishnan, G.; Delaux, P.-M.; Loqué, D.; Granell, A.; Tissier, A.; Shih, P.; Brutnell, T. P.; Quick, W. P.; Rischer, H.; Fraser, P. D.; Aharoni, A.; Raines, C.; South, P. F.; Ané, J.-M.; Hamberger, B. R.; Langdale, J.; Stougaard, J.; Bouwmeester, H.; Udvardi, M.; Murray, J. A. H.; Ntoukakis, V.; Schafer, P.; Denby, K.; Edwards, K. J.; Osbourn, A.; Haseloff, J. *New Phytol.* 2015, 208 (1), 13-19.
(34) Beck, R.; Burtscher, H. *Nucleic Adds Res.* 1994, 22 (5), 886-887.
(35) Agmon, N.; Mitchell, L. A.; Cai, Y.; Ikushima, S.; Chuang, J.; Zheng, A.; Choi, W.-J.; Martin, J. A.; Caravelli, K.; Stracquadanio, G.; Boeke, J. D. *ACS Synth. Biol.* 2015, 4 (7), 853-859.
(36) Miyazaki, K. *BioTechniques* 2015, 58 (2), 86-88.
(37) Yelton, M. M.; Hamer, J. E.; Timberlake, W. E. *Proc. Natl. Acad. Sci.* 1984, 81 (5), 1470-1474.
(38) Vollmer, S. J.; Yanofsky, C. *Proc. Natl. Acad. Sci.* 1986, 83 (13), 4869-4873.
(39) Oliver, R. P.; Roberts, I. N.; Harling, R.; Kenyon, L.; Punt, P. J.; Dingemanse, M. A.; van den Hondel, C. A. M. J. *J. Curr. Genet.* 1987, 12 (3), 231-233.

What we claim is:

1. An isolated polynucleotide comprising at least 70% nucleic acid sequence identity to SEQ ID NO:2, wherein the polynucleotide encodes a polypeptide comprising SEQ ID NO:3 and having P450 oxygenase activity.

2. The isolated polynucleotide of claim 1 comprising at least 75% nucleic acid sequence identity to SEQ ID NO:2.

3. The isolated polynucleotide of claim 1 comprising SEQ ID NO:2.

4. A transcription unit (TU) comprising the isolated polynucleotide of claim 1 and a heterologous regulatory element.

5. An isolated recombinant host cell comprising an isolated polynucleotide of claim 1 or a TU of claim 4.

6. The isolated recombinant host cell of claim 5, wherein the host cell is *Penicillium paxilli*.

7. The isolated recombinant host cell of claim 5, wherein the host cell is *Hypoxylon pulicicidum*.

8. A method of making at least one Nodulisporic Acid (NA) comprising heterologously expressing in an isolated recombinant host cell a polynucleotide comprising at least 70% nucleic acid sequence identity to SEQ ID NO:2, wherein the polynucleotide encodes a polypeptide comprising SEQ ID NO:3 and having P450 oxygenase activity.

9. The method of claim 8, wherein the isolated recombinant host cell is *Penicillium paxilli*.

10. The method of claim 8, wherein the isolated recombinant host cell is *Hypoxylon pulicicidum*.

11. The isolated polynucleotide of claim 2 comprising at least 80% nucleic acid identity to SEQ ID NO:2.

12. The isolated polynucleotide of claim 2 comprising at least 85% nucleic acid identity to SEQ ID NO:2.

13. The isolated polynucleotide of claim 2 comprising at least 90% nucleic acid identity to SEQ ID NO:2.

14. The isolated polynucleotide of claim 2 comprising at least 95% nucleic acid identity to SEQ ID NO:2.

15. The isolated polynucleotide of claim 2 comprising at least 99% nucleic acid identity to SEQ ID NO:2.

* * * * *

SEQUENCE LISTING

```
<160> NUMBER OF SEQ ID NOS: 56

<210> SEQ ID NO 1
<211> LENGTH: 1825
<212> TYPE: DNA
<213> ORGANISM: Hypoxylon pulicicidum

<400> SEQUENCE: 1
ttatgcccag atatttccag cccggggttc gaaaacaaga gaaaacgctg gtatatgaat      60
tatatagcaa tcgtatgctg gcgcagaggc ttcatggctc atcggccgcc caggcagaag     120
tctcagattg aatcttgaca ttatagagga aattaccata cgcatctcca tcatcgcgaa     180
aggtttaccg aggcatccgt acacacccac agagaaaggg atgaatgcat ctgggttgag     240
agtcaagtgt gattggctcg tccatcgctc cgggatgaac tcatctggcc tgacgaaatt     300
tctcttatct aaagacggca gagttaaaat taagctcaaa ggatgactgt atcgaatcga     360
tactaacccc tgtgtatcgt gtaagtgggc atggatacga gcatatgctc tggtataaac     420
tggccatcaa ggatcactcc accaggaccg gtctcccgct gcgagccgct catcactgct     480
ggatataaac ggagtgcttc gttgatgcaa ctgttgaggt aaggcatatt gactagggtg     540
gaggttggca taggcagtcc acctatattc atgtcatcaa cctcttttg aagaattgcc     600 tgcttgtctg gatgggttgc cagaagaaac aagatggcag taagggtcga tgctgtagag     660
tcgctaccgg ccacgacagc cagctcagaa tcatagacga ggtcatccgt atctttagac     720
tcgtcgtcta agagatggct gaatagatcg tgagtcatag ttggattctc cactgtgcgt     780
cagtcaggta tcctgattag tatgtaatta agtattacct acttgcttcc tttccactac     840
ctcctgtgag caccactgta gccaacttgt tgccttggac ctcaagaacg gtagattgcg     900
gagaaggatc aacgtccaag gcgcccacag aagtaacccc cctagttgct tgacagacct     960
cagttgcgtg aagccgggat gcgaaaggcc ttttgaatc atgttgaagg cctttccaaa    1020
tacaagccaa cccattgatt caaatgtgac tctttgcatc aattcagtta cttctaccgg    1080
ttgacctcct ctagatgaga gatagcccat gagttcttgg caacattgcc ggacatggcc    1140
ttcatgagct agcatagctg tatgctctat cagcatgaat cgcccacgcc agggttgtgt    1200
gatactcacc attaggactg aaggcctttt gccaaatttt cttccgtcgg aggtggaaat    1260
tcctgtccct tgtcatttga agggacttgt ggggataatt cacgtcgtag aatggacccc    1320
```

```
tggcacactt ggccaaatcg cgaatggcat tgaagttgtt gacggatatc tcacgaggcc   1380
ctgacacata gtctatcaac ttcgagttta tggcagagtt ggaaataggc tagaacttac   1440
taattcggac gaaatcgcca tagacactat gcatattctg tacttcaagg tgccattttc   1500
tatctacggc tgctgttttc atccatctca acgtgctcag cctggcggat accttgccgg   1560
ggaaatctct taagggatgc agaaacaacc gatatataat gattgaaaga cagatagaag   1620
agatatagca tagccaaact tggatgaaca taaaagtgat cccatataat cccactgcca   1680
acaacgagca tatgagcgca atggggcaag taatgaagca atggaacagg accggggcgt   1740
gcttgtccca ctctcctcgg atgaataaaa tagtatgaga taggacggct gccaggcaac   1800
tgatgcctaa aatagctaaa gtcat                                         1825

<210> SEQ ID NO 2
<211> LENGTH: 1599
<212> TYPE: DNA
<213> ORGANISM: Hypoxylon pulicicidum

<400> SEQUENCE: 2
ttatgcccag atatttccag cccggggttc gaaaacaaga gaaaacgctg gtatatgaat     60
tatatagcaa tcgtatgctg gcgcagaggc ttcatggctc atcggccgcc caggcagaag   120
tctcagattg aatcttgaca ttatagagga aattaccata cgcatctcca tcatcgcgaa   180
aggtttaccg aggcatccgt acacacccac agagaaaggg atgaatgcat ctgggttgag   240
agtcaagtgt gattggctcg tccatcgctc cgggatgaac tcatctggcc tgacgaaatt   300
tctcttatcc ctgtgtatcg tgtaagtggg catggatacg agcatatgct ctggtataaa   360
ctggccatca aggatcactc caccaggacc ggtctcccgc tgcgagccgc tcatcactgc   420
tggatataaa cggagtgctt cgttgatgca actgttgagg taaggcatat tgactagggt   480
ggaggttggc ataggcagtc cacctatatt catgtcatca acctcttttt gaagaattgc   540
ctgcttgtct ggatgggttg ccagaagaaa caagatggca gtaagggtcg atgctgtaga   600
gtcgctaccg gccacgacag ccagctcaga atcatagacg aggtcatccg tatctttaga   660
ctcgtcgtct aagagatggc tgaatagatc gtgagtcata gttggatttt gcttcctttc   720
cactacctcc tgtgagcacc actgtagcca acttgttgcc ttggacctca agaacggtag   780
attgcggaga aggatcaacg tccaaggcgc ccacagaagt aaccccccta gttgcttgac   840
agacctcagt tgcgtgaagc cgggatgcga aaggcctttt tgaatcatgt tgaaggcctt   900
tccaaataca agccaaccca ttgattcaaa tgtgactctt tgcatcaatt cagttacttc   960
taccggttga cctcctctag atgagagata gcccatgagt tcttggcaac attgccggac  1020
atggccttca tgagctagca tagcattagg actgaaggcc ttttgccaaa tttttcttccg  1080 tcggaggtgg aaattcctgt cccttgtcat ttgaagggac ttgtggggat aattcacgtc  1140
gtagaatgga cccctggcac acttggccaa atcgcgaatg gcattgaagt tgttgacgga  1200
tatctcacga ggcctaattc ggacgaaatc gccatagaca ctatgcatat tctgtacttc  1260
aaggtgccat tttctatcta cggctgctgt tttcatccat ctcaacgtgc tcagcctggc  1320
ggataccttg ccggggaaat ctcttaaggg atgcagaaac aaccgatata taatgattga  1380
aagacagata gaagagatat agcatagcca aacttggatg aacataaaag tgatcccata  1440
taatcccact gccaacaacg agcatatgag cgcaatgggg caagtaatga agcaatggaa  1500
caggaccggg gcgtgcttgt cccactctcc tcggatgaat aaaatagtat gagataggac  1560
```
ggctgccagg caactgatgc ctaaaatagc taaagtcat                               1599

<210> SEQ ID NO 3
<211> LENGTH: 532
<212> TYPE: PRT
<213> ORGANISM: Hypoxylon pulicicidum

<400> SEQUENCE: 3

| | | | | | | | | | | | | | | |
|---|---|---|---|---|---|---|---|---|---|---|---|---|---|---|
| Met | Thr | Leu | Ala | Ile | Leu | Gly | Ile | Ser | Cys | Leu | Ala | Ala | Val | Leu | Ser |
| 1 | | | | 5 | | | | | 10 | | | | | 15 | |
| His | Thr | Ile | Leu | Phe | Ile | Arg | Gly | Glu | Trp | Asp | Lys | His | Ala | Pro | Val |
| | | | 20 | | | | | 25 | | | | | 30 | | |
| Leu | Phe | His | Cys | Phe | Ile | Thr | Cys | Pro | Ile | Ala | Leu | Ile | Cys | Ser | Leu |
| | | | 35 | | | | | 40 | | | | | 45 | | |
| Leu | Ala | Val | Gly | Leu | Tyr | Gly | Ile | Thr | Phe | Met | Phe | Ile | Gln | Val | Trp |
| | 50 | | | | | 55 | | | | | 60 | | | | |
| Leu | Cys | Tyr | Ile | Ser | Ser | Ile | Cys | Leu | Ser | Ile | Ile | Tyr | Arg | Leu | |
| 65 | | | | | 70 | | | | | 75 | | | | | 80 |
| Phe | Leu | His | Pro | Leu | Arg | Asp | Phe | Pro | Gly | Lys | Val | Ser | Ala | Arg | Leu |
| | | | | 85 | | | | | 90 | | | | | 95 | |
| Ser | Thr | Leu | Arg | Trp | Met | Lys | Thr | Ala | Ala | Val | Asp | Arg | Lys | Trp | His |
| | | | 100 | | | | | 105 | | | | | 110 | | |
| Leu | Glu | Val | Gln | Asn | Met | His | Ser | Val | Tyr | Gly | Asp | Phe | Val | Arg | Ile |
| | | | | 115 | | | | | 120 | | | | | 125 | |
| Arg | Pro | Arg | Glu | Ile | Ser | Val | Asn | Asn | Phe | Asn | Ala | Ile | Arg | Asp | Leu |
| | 130 | | | | | 135 | | | | | 140 | | | | |
| Ala | Lys | Cys | Ala | Arg | Gly | Pro | Phe | Tyr | Asp | Val | Asn | Tyr | Pro | His | Lys |
| 145 | | | | | 150 | | | | | 155 | | | | | 160 |
| Ser | Leu | Gln | Met | Thr | Arg | Asp | Arg | Asn | Phe | His | Leu | Arg | Arg | Lys | Lys |
| | | | | 165 | | | | | 170 | | | | | 175 | |
| Ile | Trp | Gln | Lys | Ala | Phe | Ser | Pro | Asn | Ala | Met | Leu | Ala | His | Glu | Gly |
| | | | 180 | | | | | 185 | | | | | 190 | | |
| His | Val | Arg | Gln | Cys | Cys | Gln | Glu | Leu | Met | Gly | Tyr | Leu | Ser | Ser | Arg |
| | | | | 195 | | | | | 200 | | | | | 205 | |
| Gly | Gly | Gln | Pro | Val | Glu | Val | Thr | Glu | Leu | Met | Gln | Arg | Val | Thr | Phe |
| | 210 | | | | | 215 | | | | | 220 | | | | |
| Glu | Ser | Met | Gly | Trp | Leu | Val | Phe | Gly | Lys | Ala | Phe | Asn | Met | Ile | Gln |
| 225 | | | | | 230 | | | | | 235 | | | | | 240 |
| Lys | Gly | Leu | Ser | His | Pro | Gly | Phe | Thr | Gln | Leu | Arg | Ser | Val | Lys | Gln |
| | | | | 245 | | | | | 250 | | | | | 255 | |
| Leu | Gly | Gly | Leu | Leu | Leu | Trp | Ala | Pro | Trp | Thr | Leu | Ile | Leu | Leu | Arg |
| | | | 260 | | | | | 265 | | | | | 270 | | |
| Asn | Leu | Pro | Phe | Leu | Arg | Ser | Lys | Ala | Thr | Ser | Trp | Leu | Gln | Trp | Cys |
| | | | | 275 | | | | | 280 | | | | | 285 | |
| Ser | Gln | Glu | Val | Val | Glu | Arg | Lys | Gln | Asn | Pro | Thr | Met | Thr | His | Asp |
| | 290 | | | | | 295 | | | | | 300 | | | | |
| Leu | Phe | Ser | His | Leu | Leu | Asp | Asp | Glu | Ser | Lys | Asp | Thr | Asp | Asp | Leu |
| 305 | | | | | 310 | | | | | 315 | | | | | 320 |
| Val | Tyr | Asp | Ser | Glu | Leu | Ala | Val | Val | Ala | Gly | Ser | Asp | Ser | Thr | Ala |
| | | | | 325 | | | | | 330 | | | | | 335 | |
| Ser | Thr | Leu | Thr | Ala | Ile | Leu | Phe | Leu | Leu | Ala | Thr | His | Pro | Asp | Lys |
| | | | 340 | | | | | 345 | | | | | 350 | | |
| Gln | Ala | Ile | Leu | Gln | Lys | Glu | Val | Asp | Asp | Met | Asn | Ile | Gly | Gly | Leu |
| | | | | 355 | | | | | 360 | | | | | 365 | |

-continued

```
Pro Met Pro Thr Ser Thr Leu Val Asn Met Pro Tyr Leu Asn Ser Cys
    370                 375                 380

Ile Asn Glu Ala Leu Arg Leu Tyr Pro Ala Val Met Ser Gly Ser Gln
385                 390                 395                 400

Arg Glu Thr Gly Pro Gly Gly Val Ile Leu Asp Gly Gln Phe Ile Pro
                405                 410                 415

Glu His Met Leu Val Ser Met Pro Thr Tyr Thr Ile His Arg Asp Lys
            420                 425                 430

Arg Asn Phe Val Arg Pro Asp Glu Phe Ile Pro Glu Arg Trp Thr Ser
        435                 440                 445

Gln Ser His Leu Thr Leu Asn Pro Asp Ala Phe Ile Pro Phe Ser Val
    450                 455                 460

Gly Val Tyr Gly Cys Leu Gly Lys Pro Phe Ala Met Met Glu Met Arg
465                 470                 475                 480

Met Val Ile Ser Ser Ile Met Ser Arg Phe Asn Leu Arg Leu Leu Pro
                485                 490                 495

Gly Arg Pro Met Ser His Glu Ala Ser Ala Pro Ala Tyr Asp Cys Tyr
                500                 505                 510

Ile Ile His Ile Pro Ala Phe Ser Leu Val Phe Glu Pro Arg Ala Gly
            515                 520                 525

Asn Ile Trp Ala
        530

<210> SEQ ID NO 4
<211> LENGTH: 1826
<212> TYPE: DNA
<213> ORGANISM: Hypoxylon pulicicidum

<400> SEQUENCE: 4
atgtttgata ttgattttgg cattctattt ccaatttcct gggaacaatc ccctatcttt      60
ctggctgttg gctaatatt cgcatttgcg accttatctc cgtggctccg ttccggggaa     120
cgcctgatca atggtcgcga aggcttcgaa atactgtgga cgaatgcgaa gaagcgatat     180
caaacgaagg ggcgatctgt tatggaggca ggcttttcaa aggtaggata catcattgtc     240
tccaaatgaa agacatcaaa tcgtgccggg tcatatgtgc tgatacttgg agatagtaca     300
acgattcttt ctacatgatg acggatagtg gtaccgaaat ggtcctacac ccgagatacg     360
tcgacgagat ccggaacgac ccaaggttgg actttcacag atatatgaaa actgtaatag     420
aattcgatcc attttctata tatccgggct gacgtctacg tacgcgaggt cctacatggg     480
ctcagacaga aaggtggcga gataaaccga gatcttatcc aaaccaaatt gactagatct     540
gtgggtaagg ggttgtcgtc ctctagagaa tgcaggcaaa gggaaggaca agagtaaact     600
aatgcccatc cttgtatagg taggctcatt gggtccatat cggctgaaat cgaggacgcc     660
cttcacaatc gatgggaaga aggcgaaggt gaatatgaag agtaccttct agtgcttccc     720
cctgctgaaa tgcatacaga atggcatgag attgtattgc tctccgtaat gatcccggtt     780
gttgcgcaag gagtatccaa aatgtttgtc ggagatccat tgtgccgtaa caaggattgg     840
ataggtatga tcttaaggca tacaaggagt gtccagacag cactgcggtc ccttcgattg     900
tggccttact ttcttagacc acttgcagcc agatttctgc caacctgtcg acaagtcact     960
gcagaaatag aagaggccag cgcatcatc aatccagtac ttgagaagaa gcgtgccgag    1020
aagctcgcaa tgattcagaa gggagaaaaa cctccagagc ccaacaccta catggattgg    1080
ttagaagaat ccgacaagga tgaattctat gacccagttg ttgctcagct gaagatttcc    1140
```

-continued

```
atggcagcta tacacgctac ctcggacctc ttatcgcaga caattttcag cctatgtgac      1200
agcccagagc tagtcaagga actgcgagcc gaagctgtgt ctgttatagg agcgtacggc      1260
tggggaagg aagcaatcta caacctgaag ctgatggaca gcgtcctgaa ggagacgcaa      1320
cgcctaaaac ctatgcaaat cagtaagcgc cggtgccgcc gtgtggactt gctatcgcta      1380
atcgctttgc ctttgcttgc tctctagact tgacgcgact agctctagat cgcataaaac      1440
tttccgatgg cacggttatc cctaggggct ccaaagttct tatctcctgc cacaacatgt      1500
gggattcgaa cgtctacccc aacgcaaacc agtatgacgg tcatcgcttc tataaacttc      1560
ggcagcgcgc tggaatggag aattccgcac agctatcaac acctagtccg gatcatctgg      1620
gcttcggact gggaatgtat gcctgtcccg gtaggcatat cgcatcgacc gttatgaaag      1680
tcacactatg ccatatcctc ctgaagtatg acttcgaatt ggcggagggc tgcacccta      1740
gagtgattga atatggtagt ttcttgttag ctgatccaac ggcgagagtt tctatcagac      1800
ggcggaaaga agagattcaa ctgtaa                                          1826
```

```
<210> SEQ ID NO 5
<211> LENGTH: 1536
<212> TYPE: DNA
<213> ORGANISM: Hypoxylon pulicicidum

<400> SEQUENCE: 5
```

```
atgtttgata ttgattttgg cattctattt ccaatttcct gggaacaatc ccctatcttt       60
ctggctgttg ggctaatatt cgcatttgcg accttatctc cgtggctccg ttccggggaa      120
cgcctgatca atggtcgcga aggcttcgaa atactgtgga cgaatgcgaa gaagcgatat      180
caaacgaagg ggcgatctgt tatggaggca ggcttttcaa agtacaacga ttctttctac      240
atgatgacgg atagtggtac cgaaatggtc ctacacccga gatacgtcga cgagatccgg      300
aacgacccaa ggttggactt tcacagatat atgaaaacta aggtggcga gataaaccga      360
gatcttatcc aaaccaaatt gactagatct gtgggtaggc tcattgggtc catatcggct      420
gaaatcgagg acgcccttca aatcgatgg gaagaaggcg aaggtgaata tgaagagtac      480
cttctagtgc ttccccctgc tgaaatgcat acagaatggc atgagattgt attgctctcc      540
gtaatgatcc cggttgttgc gcaaggagta tccaaaatgt ttgtcggaga tccattgtgc      600
cgtaacaagg attggatagg tatgatctta aggcatacaa ggagtgtcca gacagcactg      660
cggtcccttc gattgtggcc ttactttctt agaccacttg cagccagatt tctgccaacc      720
tgtcgacaag tcactgcaga aatagaagag gccaggcgca tcatcaatcc agtacttgag      780
aagaagcgtg ccgagaagct cgcaatgatt cagaagggag aaaaacctcc agagcccaac      840
acctacatgg attggttaga agaatccgac aaggatgaat ctatgacccc agttgttgct      900
cagctgaaga tttccatggc agctatacac gctacctcgg acctcttatc gcagacaatt      960
ttcagcctat gtgacagccc agagctagtc aaggaactgc gagccgaagc tgtgtctgtt     1020
ataggagcgt acggctgggg gaaggaagca atctacaacc tgaagctgat ggacagcgtc     1080
ctgaaggaga cgcaacgcct aaaacctatg caaatcaact tgacgcgact agctctagat     1140
cgcataaaac tttccgatgg cacggttatc cctaggggct ccaaagttct tatctcctgc     1200
cacaacatgt gggattcgaa cgtctacccc aacgcaaacc agtatgacgg tcatcgcttc     1260
tataaacttc ggcagcgcgc tggaatggag aattccgcac agctatcaac acctagtccg     1320
gatcatctgg gcttcggact gggaatgtat gcctgtcccg gtaggcatat cgcatcgacc     1380
gttatgaaag tcacactatg ccatatcctc ctgaagtatg acttcgaatt ggcggagggc     1440
```

```
tgcaccccta gagtgattga atatggtagt ttcttgttag ctgatccaac ggcgagagtt    1500
tctatcagac ggcggaaaga agagattcaa ctgtaa                              1536
```

<210> SEQ ID NO 6
<211> LENGTH: 511
<212> TYPE: PRT
<213> ORGANISM: Hypoxylon pulicicidum

<400> SEQUENCE: 6

```
Met Phe Asp Ile Asp Phe Gly Ile Leu Phe Pro Ile Ser Trp Glu Gln
1               5                   10                  15

Ser Pro Ile Phe Leu Ala Val Gly Leu Ile Phe Ala Phe Ala Thr Leu
            20                  25                  30

Ser Pro Trp Leu Arg Ser Gly Glu Arg Leu Ile Asn Gly Arg Glu Gly
        35                  40                  45

Phe Glu Ile Leu Trp Thr Asn Ala Lys Lys Arg Tyr Gln Thr Lys Gly
    50                  55                  60

Arg Ser Val Met Glu Ala Gly Phe Ser Lys Tyr Asn Asp Ser Phe Tyr
65                  70                  75                  80

Met Met Thr Asp Ser Gly Thr Glu Met Val Leu His Pro Arg Tyr Val
                85                  90                  95

Asp Glu Ile Arg Asn Asp Pro Arg Leu Asp Phe His Arg Tyr Met Lys
            100                 105                 110

Thr Lys Gly Gly Glu Ile Asn Arg Asp Leu Ile Gln Thr Lys Leu Thr
        115                 120                 125

Arg Ser Val Gly Arg Leu Ile Gly Ser Ile Ser Ala Glu Ile Glu Asp
    130                 135                 140

Ala Leu His Asn Arg Trp Glu Glu Gly Glu Gly Glu Tyr Glu Glu Tyr
145                 150                 155                 160

Leu Leu Val Leu Pro Pro Ala Glu Met His Thr Glu Trp His Glu Ile
                165                 170                 175

Val Leu Leu Ser Val Met Ile Pro Val Val Ala Gln Gly Val Ser Lys
            180                 185                 190

Met Phe Val Gly Asp Pro Leu Cys Arg Asn Lys Asp Trp Ile Gly Met
        195                 200                 205

Ile Leu Arg His Thr Arg Ser Val Gln Thr Ala Leu Arg Ser Leu Arg
    210                 215                 220

Leu Trp Pro Tyr Phe Leu Arg Pro Leu Ala Ala Arg Phe Leu Pro Thr
225                 230                 235                 240

Cys Arg Gln Val Thr Ala Glu Ile Glu Ala Arg Arg Ile Ile Asn
                245                 250                 255

Pro Val Leu Glu Lys Lys Arg Ala Glu Lys Leu Ala Met Ile Gln Lys
            260                 265                 270

Gly Glu Lys Pro Pro Glu Pro Asn Thr Tyr Met Asp Trp Leu Glu Glu
        275                 280                 285

Ser Asp Lys Asp Glu Phe Tyr Asp Pro Val Val Ala Gln Leu Lys Ile
    290                 295                 300

Ser Met Ala Ala Ile His Ala Thr Ser Asp Leu Leu Ser Gln Thr Ile
305                 310                 315                 320

Phe Ser Leu Cys Asp Ser Pro Glu Leu Val Lys Glu Leu Arg Ala Glu
                325                 330                 335

Ala Val Ser Val Ile Gly Ala Tyr Gly Trp Gly Lys Glu Ala Ile Tyr
            340                 345                 350
```

```
Asn Leu Lys Leu Met Asp Ser Val Leu Lys Glu Thr Gln Arg Leu Lys
            355                 360                 365

Pro Met Gln Ile Asn Leu Thr Arg Leu Ala Leu Asp Arg Ile Lys Leu
        370                 375                 380

Ser Asp Gly Thr Val Ile Pro Arg Gly Ser Lys Val Leu Ile Ser Cys
385                 390                 395                 400

His Asn Met Trp Asp Ser Asn Val Tyr Pro Asn Ala Asn Gln Tyr Asp
                405                 410                 415

Gly His Arg Phe Tyr Lys Leu Arg Gln Arg Ala Gly Met Glu Asn Ser
            420                 425                 430

Ala Gln Leu Ser Thr Pro Ser Pro Asp His Leu Gly Phe Gly Leu Gly
        435                 440                 445

Met Tyr Ala Cys Pro Gly Arg His Ile Ala Ser Thr Val Met Lys Val
450                 455                 460

Thr Leu Cys His Ile Leu Leu Lys Tyr Asp Phe Glu Leu Ala Glu Gly
465                 470                 475                 480

Cys Thr Pro Arg Val Ile Glu Tyr Gly Ser Phe Leu Leu Ala Asp Pro
                485                 490                 495

Thr Ala Arg Val Ser Ile Arg Arg Arg Lys Glu Glu Ile Gln Leu
            500                 505                 510

<210> SEQ ID NO 7
<211> LENGTH: 2012
<212> TYPE: DNA
<213> ORGANISM: Hypoxylon pulicicidum

<400> SEQUENCE: 7
ctaatctgcg atggaccctg accctaaccc tgaccctgac ctgaatccgg accctgctc      60
atcctcgtct ctcacaatct cacggcgtag atctgccggc caagttggcg catcgactcc    120
gttccctctc gtgcccacat tatacttgag ttcaatcgcg tcgtccttga atcgagcgat    180
aggccttact tgtatgaacg tcgtgttcaa cgcgccggac cggaatgggc cgaaaaattc    240
cctttgaaag agaatctcgc cgtcgaattt gtacaatgcc gttagcagct taggcagcat    300
gtattgcatg gagtggtagt gtctgaaaac aggtgcgtcg tgacggcgga acaggtcagt    360
ccaggtatgc tcgtcgtatg tcccgactga tcgaacaagc cattgattgt aatagttgat    420
tgataccctgg aaatactgta tgagcgataa ccagcgatag cgtatccggg ggctacctac    480
atcaaccctg tagcttcccc ctttctcggc tctttggaca agggcgtcca agacagccgt    540
ggacccgcat attccggtac tagaagatat gtcagtcagg ctgcaactct gctaccaagt    600
gaagaggtat ctctcgatcg gctcaccaat aatcagaatt gaacagagca ggagttacag    660
gctcttcaag acccatagca tggccgtacg aagtagaaat cccgcagcac gcatcgctaa    720
tctgctgcca gccgcttcta tggctccagg gtccatacca accatagcag ttctccctga    780
cgtaaataat accacgactg cggtcccgca ccagattgaa cacctcgtcg tagccaaagc    840
caaaacgttt catcacacct ggccgatagc tatctacaac cacatctgca tccaatatca    900
agtccctcag cttttggcgg tcagattcga catccaaccg tagccatgag ttccatttgc    960
cccaattcaa gtcttggtgt aacaccgaca tgtccgtgat gtctgggaa gtaacacgca    1020
ttacactagc cccatctccg caagacttc gtgttatcgt cggacccgct atagcgcgcg    1080
ttaagtccac caccttcagc ccggccagcg gtctcttggg gctcgatgga gcgttaggat    1140
gatcaggcca ccaggctgct ggctgagaag aatttgggtc tctaatgacc tcatacagtc    1200
ccaccttgcc atttttctgg ccgtgctcgc tggcaaagta ctcagcggag ctgtagacaa    1260
```

-continued

```
tggtaccggc ttggcgatgt tcttcattta gcaaatggtc tagatgtgtg gcgtcatact      1320
ttgagagtct ttgttggatc ctgtcggtta cgacctcaga agtgtcttga acctcgcctt      1380
cgacgggcaa ccctagtgcc tgtagggtgg gctctggatt cattcccccct ggaggaatat     1440
cgattagtct ctagattgac tcggcttgca agatcatacc gtgtgtatgg tagaaacggc      1500
catcctttgt tttatagata ttggtaatca atgcccgttg tagagatgcg ttggcgcgat      1560
gtttatctcg gttcggaaaa agttctgctg tcagtgtatc aaatggcgag aaaggacgga      1620
cttctcctct atcctcgatt tgggtgagca tgggggacat gaggaacaag gttgcgtggt      1680
ctctatctga tgttagacaa acggccagtg cttcatatac atcacaatcc gagaacttac      1740
gtgtttattg agacattgct agggcgtaca ccatacttcc gatgggccag ataattcagg      1800
aacgttgctt caaaggcttt caaagctgag atgctctctg cgagcctcca gttaacagga      1860
atgctaggct tgacgtttcc ctcgaaggag acaaatttgg cgatttcggc cagctcaggg      1920
ggaagatttg gcattagcgg attctctaga atttcgcgta tgaatacaga ttccgcttgc      1980
ttgggaactg tattatccgc acttgactcc at                                    2012

<210> SEQ ID NO 8
<211> LENGTH: 1782
<212> TYPE: DNA
<213> ORGANISM: Hypoxylon pulicicidum
<400> SEQUENCE: 8
ctaatctgcg atggaccctg accctaaccc tgaccctgac ctgaatccgg acccctgctc       60
atcctcgtct ctcacaatct cacggcgtag atctgccggc caagttggcg catcgactcc      120
gttccctctc gtgcccacat tatacttgag ttcaatcgcg tcgtccttga atcgagcgat      180
aggccttact tgtatgaacg tcgtgttcaa cgcgccggac cggaatgggc cgaaaaattc      240
cctttgaaag agaatctcgc cgtcgaattt gtacaatgcc gttagcagct taggcagcat      300
gtattgcatg gagtggtagt gtctgaaaac aggtgcgtcg tgacggcgga acaggtcagt      360
ccaggtatgc tcgtcgtatg tcccgactga tcgaacaagc cattgattgt aatagttgat      420
tgatacatca accctgtagc ttcccccttt ctcggctctt tggacaaggg cgtccaagac      480
agccgtggac ccgcatattc cggtacaata atcagaattg aacagagcag gagttacagg      540
ctcttcaaga cccatagcat ggccgtacga agtagaaatc ccgcagcacg catcgctaat      600
ctgctgccag ccgcttctat ggctccaggg tccataccaa ccatagcagt tctccctgac      660
gtaaataata ccacgactgc ggtcccgcac cagattgaac cctcgtcgt agccaaagcc      720
aaaacgtttc atcacacctg gccgatagct atctacaacc acatctgcat ccaatatcaa      780
gtccctcagc ttttggcggt cagattcgac atccaaccgt agccatgagt tccatttgcc      840
ccaattcaag tcttggtgta acaccgacat gtccgtgatg tctggggaag taacacgcat      900
tacactagcc cccatctccg caagacttcg tgttatcgtc ggaccccgcta tagcgcgcgt      960
taagtccacc accttcagcc cggccagcgg tctcttgggg ctcgatggag cgttaggatg     1020
atcaggccac caggctgctg gctgagaaga atttgggtct ctaatgacct catacagtcc     1080
caccttgcca ttttctggc cgtgctcgct ggcaaagtac tcagcggagc tgtagacaat     1140
ggtaccggct tggcgatgtt cttcatttag caaatggtct agatgtgtgg cgtcatactt     1200
tgagagtctt tgttggatcc tgtcggttac gacctcagaa gtgtcttgaa cctcgccttc     1260
gacgggcaac cctagtgcct gtagggtggg ctctggattc attcccccgt gtgtatggta     1320
```

-continued

```
gaaacggcca tcctttgttt tatagatatt ggtaatcaat gcccgttgta gagatgcgtt    1380
ggcgcgatgt ttatctcggt tcggaaaaag ttctgctgtc agtgtatcaa atggcgagaa    1440
aggacggact tctcctctat cctcgatttg ggtgagcatg ggggacatga ggaacaaggt    1500
tgcgtggtct gtgtttattg agacattgct agggcgtaca ccatacttcc gatgggccag    1560
ataattcagg aacgttgctt caaaggcttt caaagctgag atgctctctg cgagcctcca    1620
gttaacagga atgctaggct tgacgtttcc ctcgaaggag acaaatttgg cgatttcggc    1680
cagctcaggg ggaagatttg gcattagcgg attctctaga atttgcgta tgaatacaga    1740 ttccgcttgc ttgggaactg tattatccgc acttgactcc at                       1782
```

<210> SEQ ID NO 9
<211> LENGTH: 593
<212> TYPE: PRT
<213> ORGANISM: Hypoxylon pulicicidum

<400> SEQUENCE: 9

```
Met Glu Ser Ser Ala Asp Asn Thr Val Pro Lys Gln Ala Glu Ser Val
1               5                   10                  15

Phe Ile Arg Glu Ile Leu Glu Asn Pro Leu Met Pro Asn Leu Pro Pro
            20                  25                  30

Glu Leu Ala Glu Ile Ala Lys Phe Val Ser Phe Glu Gly Asn Val Lys
        35                  40                  45

Pro Ser Ile Pro Val Asn Trp Arg Leu Ala Glu Ser Ile Ser Ala Leu
    50                  55                  60

Lys Ala Phe Glu Ala Thr Phe Leu Asn Tyr Leu Ala His Arg Lys Tyr
65                  70                  75                  80

Gly Val Arg Pro Ser Asn Val Ser Ile Asn Thr Asp His Ala Thr Leu
                85                  90                  95

Phe Leu Met Ser Pro Met Leu Thr Gln Ile Glu Asp Arg Gly Glu Val
            100                 105                 110

Arg Pro Phe Ser Pro Phe Asp Thr Leu Thr Ala Glu Leu Phe Pro Asn
        115                 120                 125

Arg Asp Lys His Arg Ala Asn Ala Ser Leu Gln Arg Ala Leu Ile Thr
    130                 135                 140

Asn Ile Tyr Lys Thr Lys Asp Gly Arg Phe Tyr His Thr His Gly Gly
145                 150                 155                 160

Met Asn Pro Glu Pro Thr Leu Gln Ala Leu Gly Leu Pro Val Glu Gly
                165                 170                 175

Glu Val Gln Asp Thr Ser Glu Val Val Thr Asp Arg Ile Gln Gln Arg
            180                 185                 190

Leu Ser Lys Tyr Asp Ala Thr His Leu Asp His Leu Leu Asn Glu Glu
        195                 200                 205

His Arg Gln Ala Gly Thr Ile Val Tyr Ser Ser Ala Glu Tyr Phe Ala
    210                 215                 220

Ser Glu His Gly Gln Lys Asn Gly Lys Val Gly Leu Tyr Glu Val Ile
225                 230                 235                 240

Arg Asp Pro Asn Ser Ser Gln Pro Ala Ala Trp Trp Pro Asp His Pro
                245                 250                 255

Asn Ala Pro Ser Ser Pro Lys Arg Pro Leu Ala Gly Leu Lys Val Val
            260                 265                 270

Asp Leu Thr Arg Ala Ile Ala Gly Pro Thr Ile Thr Arg Ser Leu Ala
        275                 280                 285

Glu Met Gly Ala Ser Val Met Arg Val Thr Ser Pro Asp Ile Thr Asp
```

```
                290                 295                 300
Met Ser Val Leu His Gln Asp Leu Asn Trp Gly Lys Trp Asn Ser Trp
305                 310                 315                 320
Leu Arg Leu Asp Val Glu Ser Asp Arg Gln Lys Leu Arg Asp Leu Ile
                325                 330                 335
Leu Asp Ala Asp Val Val Asp Ser Tyr Arg Pro Gly Val Met Lys
                340                 345                 350
Arg Phe Gly Phe Gly Tyr Asp Glu Val Phe Asn Leu Val Arg Asp Arg
                355                 360                 365
Ser Arg Gly Ile Ile Tyr Val Arg Glu Asn Cys Tyr Gly Trp Tyr Gly
                370                 375                 380
Pro Trp Ser His Arg Ser Gly Trp Gln Gln Ile Ser Asp Ala Cys Cys
385                 390                 395                 400
Gly Ile Ser Thr Ser Tyr Gly His Ala Met Gly Leu Glu Glu Pro Val
                405                 410                 415
Thr Pro Ala Leu Phe Asn Ser Asp Tyr Cys Thr Gly Ile Cys Gly Ser
                420                 425                 430
Thr Ala Val Leu Asp Ala Leu Val Gln Arg Ala Glu Lys Gly Gly Ser
                435                 440                 445
Tyr Arg Val Asp Val Ser Ile Asn Tyr Tyr Asn Gln Trp Leu Val Arg
                450                 455                 460
Ser Val Gly Thr Tyr Asp Glu His Thr Trp Thr Asp Leu Phe Arg Arg
465                 470                 475                 480
His Asp Ala Pro Val Phe Arg His Tyr His Ser Met Gln Tyr Met Leu
                485                 490                 495
Pro Lys Leu Leu Thr Ala Leu Tyr Lys Phe Asp Gly Glu Ile Leu Phe
                500                 505                 510
Gln Arg Glu Phe Phe Gly Pro Phe Arg Ser Gly Ala Leu Asn Thr Thr
                515                 520                 525
Phe Ile Gln Val Arg Pro Ile Ala Arg Phe Lys Asp Asp Ala Ile Glu
                530                 535                 540
Leu Lys Tyr Asn Val Gly Thr Arg Gly Asn Gly Val Asp Ala Pro Thr
545                 550                 555                 560
Trp Pro Ala Asp Leu Arg Arg Glu Ile Val Arg Asp Glu Asp Glu Gln
                565                 570                 575
Gly Ser Gly Phe Arg Ser Gly Ser Gly Leu Gly Ser Gly Ser Ile Ala
                580                 585                 590
Asp

<210> SEQ ID NO 10
<211> LENGTH: 1577
<212> TYPE: DNA
<213> ORGANISM: Hypoxylon pulicicidum

<400> SEQUENCE: 10
atgtctaccc ctgagttcaa ggtgataatc gttggcggct cccttgcggg tctaacattg      60
gcccattgcc tcctccgcgc cggaatttcc cacatcgttc ttgagagacg tagtgtaatc     120
gcaccagagg aagtgcctc aatagggatt cttcctaatg cgctcgtgt cttggatcaa      180 ctaggcatct atgaacatat tcaagacact actgagccat tgagtacagc tcatatacga     240
tatccagatg ggttctattt cagcagtcgc tatcccgaga tcataaaaga aggtgagca      300 ctcccatgaa catatgccta tcgtttgcgc aatggctgac cccagcatgg ccgttcgtag     360
gtttgggtat ccgatagcct tttaccccg gaggagactt ttggagattc tctatacatc     420
```

```
gtaccctgac cattctaaca tctataccaa caagaatgtg atcaaggtgc aaagccatga      480
taatcaagtt tctgtcttga cagaggatgg aaatacatat cgaggggatc ttgtggtggg      540
cgccgacggt gtcaacagtc gagttctatc tgaaatttgg aaattagcag gtaatccctc      600
tctcacgaaa cgggaaggaa gaggtcagtc gagatcttta atattcgca tagcgactca       660 tacagacgtt gataataaac ttaggaagga ccatcgagta cgcttgtgtg tttgggatat      720
cctcgccaat ctcagacctc aagcccggcg agcaggttaa cgcgttctac gacggactca      780
caatcgtcac gatccatggt agaaacggag agatattctg gttttttatc aagaaactct      840
cgcgtcgcta tatctatccc gatctcatca gattacagca gaaagacgca gaagggatct      900
gtgaagaagc caagtcacta actgtctgga aaggtgttac attcggtgac atttgggaaa      960
gaagagaaac agcatcattg accgttttgg atgagttctt gcatcacact tggagttggg     1020
acagatcggt ttgtgtgggc gacagtatcc acaaggtata tgcctcctat ggtctgaagc     1080
acattaaggg gttggctaac gctgtcatat agatgactcc aaattttggc cagggtgcga     1140
atactgctat cgaggattct gccgctctag ccaatctact gcacagtttg atcaaggaga     1200
aacgagccga aaagccgact gactcagata tatcactgct tctgaggcag ttcaaatcac     1260
agcgtcttcg acgcgttcag aagatatata aaatgtcaag gtttgttacg cggcttcaag     1320
cgcgcgatgg gttgttgaat actcttctgg gacgccatta cgccccatat gcagcagatc     1380
ttccagctaa gattgcctct ggatgcatcg ctggtgcgga agttctggat tacctcccat     1440
tacccaaggt aactgggcg ggctggaata ggggccatcg tagatctacc atgtacatcc      1500
tgctaggatt cacaggggta ttcacctctg ctctggcgat ggtagtgtta ctccatatta     1560
gagacatcgc ttcatag                                                    1577

<210> SEQ ID NO 11
<211> LENGTH: 1392
<212> TYPE: DNA
<213> ORGANISM: Hypoxylon pulicicidum

<400> SEQUENCE: 11
atgtctaccc ctgagttcaa ggtgataatc gttggcggct cccttgcggg tctaacattg       60
gcccattgcc tcctccgcgc cggaatttcc cacatcgttc ttgagagacg tagtgtaatc      120
gcaccagagg aaggtgcctc aatagggatt cttcctaatg gcgctcgtgt cttggatcaa      180
ctaggcatct atgaacatat tcaagacact actgagccat tgagtacagc tcatatacga      240
tatccagatg ggttctattt cagcagtcgc tatcccgaga tcataaaaga aaggtttggg      300
tatccgatag cctttttacc ccggaggaga cttttggaga ttctctatac atcgtaccct      360
gaccattcta acatctatac caacaagaat gtgatcaagg tgcaaagcca tgataatcaa      420
gtttctgtct tgacagagga tggaaataca tatcgagggg atcttgtggt gggcgccgac      480
ggtgtcaaca gtcgagttct atctgaaatt tggaaattag caggtaatcc ctctctcacg      540
aaacgggaag gaagaggaag gaccatcgag tacgcttgtg tgtttgggat atcctcgcca      600
atctcagacc tcaagcccgg cgagcaggtt aacgcgttct acgacggact cacaatcgtc      660
acgatccatg gtagaaacgg agagatattc tggtttttta tcaagaaact ctcgcgtcgc      720
tatatctatc ccgatctcat cagattacag cagaaagacg cagaagggat ctgtgaagaa      780
gccaagtcac taactgtctg gaaaggtgtt acattcggtg acatttggga agaagagaaa      840
acagcatcat tgaccgtttt ggatgagttc ttgcatcaca cttggagttg ggacagatcg      900
```

-continued

```
gtttgtgtgg cgacagtat ccacaagatg actccaaatt ttggccaggg tgcgaatact    960
gctatcgagg attctgccgc tctagccaat ctactgcaca gtttgatcaa ggagaaacga   1020
gccgaaaagc cgactgactc agatatatca ctgcttctga ggcagttcaa atcacagcgt   1080
cttcgacgcg ttcagaagat atataaaatg tcaaggtttg ttacgcggct tcaagcgcgc   1140
gatgggttgt tgaatactct tctgggacgc cattacgccc catatgcagc agatcttcca   1200
gctaagattg cctctggatg catcgctggt gcggaagttc tggattacct cccattaccc   1260
aaggtaactg gggcgggctg gaatagggggc catcgtagat ctaccatgta catcctgcta   1320
ggattcacag gggtattcac ctctgctctg gcgatggtag tgttactcca tattagagac   1380
atcgcttcat ag                                                       1392
```

<210> SEQ ID NO 12
<211> LENGTH: 463
<212> TYPE: PRT
<213> ORGANISM: Hypoxylon pulicicidum

<400> SEQUENCE: 12

```
Met Ser Thr Pro Glu Phe Lys Val Ile Ile Val Gly Gly Ser Leu Ala
1               5                   10                  15

Gly Leu Thr Leu Ala His Cys Leu Leu Arg Ala Gly Ile Ser His Ile
            20                  25                  30

Val Leu Glu Arg Arg Ser Val Ile Ala Pro Glu Glu Gly Ala Ser Ile
        35                  40                  45

Gly Ile Leu Pro Asn Gly Ala Arg Val Leu Asp Gln Leu Gly Ile Tyr
    50                  55                  60

Glu His Ile Gln Asp Thr Thr Glu Pro Leu Ser Thr Ala His Ile Arg
65                  70                  75                  80

Tyr Pro Asp Gly Phe Tyr Phe Ser Ser Arg Tyr Pro Glu Ile Ile Lys
                85                  90                  95

Glu Arg Phe Gly Tyr Pro Ile Ala Phe Leu Pro Arg Arg Arg Leu Leu
            100                 105                 110

Glu Ile Leu Tyr Thr Ser Tyr Pro Asp His Ser Asn Ile Tyr Thr Asn
        115                 120                 125

Lys Asn Val Ile Lys Val Gln Ser His Asp Asn Gln Val Ser Val Leu
    130                 135                 140

Thr Glu Asp Gly Asn Thr Tyr Arg Gly Asp Leu Val Val Gly Ala Asp
145                 150                 155                 160

Gly Val Asn Ser Arg Val Leu Ser Glu Ile Trp Lys Leu Ala Gly Asn
                165                 170                 175

Pro Ser Leu Thr Lys Arg Glu Gly Arg Gly Arg Thr Ile Glu Tyr Ala
            180                 185                 190

Cys Val Phe Gly Ile Ser Ser Pro Ile Ser Asp Leu Lys Pro Gly Glu
        195                 200                 205

Gln Val Asn Ala Phe Tyr Asp Gly Leu Thr Ile Val Thr Ile His Gly
    210                 215                 220

Arg Asn Gly Glu Ile Phe Trp Phe Phe Ile Lys Lys Leu Ser Arg Arg
225                 230                 235                 240

Tyr Ile Tyr Pro Asp Leu Ile Arg Leu Gln Gln Lys Asp Ala Glu Gly
                245                 250                 255

Ile Cys Glu Glu Ala Lys Ser Leu Thr Val Trp Lys Gly Val Thr Phe
            260                 265                 270

Gly Asp Ile Trp Glu Arg Arg Glu Thr Ala Ser Leu Thr Val Leu Asp
        275                 280                 285
```

```
Glu Phe Leu His His Thr Trp Ser Trp Asp Arg Ser Val Cys Val Gly
    290                 295                 300
Asp Ser Ile His Lys Met Thr Pro Asn Phe Gln Gly Ala Asn Thr
305                 310                 315                 320
Ala Ile Glu Asp Ser Ala Ala Leu Ala Asn Leu Leu His Ser Leu Ile
                325                 330                 335
Lys Glu Lys Arg Ala Glu Lys Pro Thr Asp Ser Asp Ile Ser Leu Leu
                340                 345                 350
Leu Arg Gln Phe Lys Ser Gln Arg Leu Arg Arg Val Gln Lys Ile Tyr
                355                 360                 365
Lys Met Ser Arg Phe Val Thr Arg Leu Gln Ala Arg Asp Gly Leu Leu
    370                 375                 380
Asn Thr Leu Leu Gly Arg His Tyr Ala Pro Tyr Ala Ala Asp Leu Pro
385                 390                 395                 400
Ala Lys Ile Ala Ser Gly Cys Ile Ala Gly Ala Glu Val Leu Asp Tyr
                405                 410                 415
Leu Pro Leu Pro Lys Val Thr Gly Ala Gly Trp Asn Arg Gly His Arg
                420                 425                 430
Arg Ser Thr Met Tyr Ile Leu Leu Gly Phe Thr Gly Val Phe Thr Ser
                435                 440                 445
Ala Leu Ala Met Val Val Leu Leu His Ile Arg Asp Ile Ala Ser
    450                 455                 460

<210> SEQ ID NO 13
<211> LENGTH: 803
<212> TYPE: DNA
<213> ORGANISM: Hypoxylon pulicicidum

<400> SEQUENCE: 13
ttattgagcc ttccgcgcat tgcttcgttc ttggccatgt tcgtatttct tcacattcca      60
cagacaaatt ccatagaggc tgtctaccgc aatgaataca ccgaggctcc atagtaccag     120
aggactattg agccagttga atgcctccga ccagtacatg tacctcaata tggcaaaccc     180
aaccacacaa ccggatccta taaagcgaga taacctatac cttgttattt atatgtcctc     240
aaagttctgt tgcataactt cggagcaaga agatggatta cctaccataa ggtatatgaa     300
gctccacgac tactacttct ccctagaagc tggcagaacc ccccgacgct agcagtagc     360
tggcaagcca ctgcacccca agaatatcca agtgctggcc aatctctgc tgctagggct     420
agatggcccg tcaaggagcc aagacacct agtgcgaaaa tgagtgtgat gttgttcatc     480
acaagaggcg catgggccca ttcattcggc gcaaacctga tcgcggtgta catgactccg     540
agattgacta ccagtccagc tagaaacaca ccttgctcga tgcggctttt tgaagggtag     600
ataagaccat ataccatttc ccaagcaaag ttgcagcaaa gagccagcgg tgccatgctg     660
taagtctgtt cctggagcga ggtgtagatc atgccggcgt agtttatgag ccaacaaacg     720
cccattccga agacgaagat gtccgaaatc cattcgacgc gctgatattc aacgggtgca     780
ttggaacgat cgaatccatc cat                                            803

<210> SEQ ID NO 14
<211> LENGTH: 732
<212> TYPE: DNA
<213> ORGANISM: Hypoxylon pulicicidum

<400> SEQUENCE: 14
ttattgagcc ttccgcgcat tgcttcgttc ttggccatgt tcgtatttct tcacattcca      60
```

-continued

```
cagacaaatt ccatagaggc tgtctaccgc aatgaataca ccgaggctcc atagtaccag    120
aggactattg agccagttga atgcctccga ccagtacatg tacctcaata tggcaaaccc    180
aaccacacaa ccggatccta taaagcgaga taaccataag gtatatgaag ctccacgact    240
actacttctc cctagaagct ggcagaaccc cccgacgctt agcagtagct ggcaagccac    300
tgcaccccaa gaatatccaa gtgctggccc aatctctgct gctagggcta gatggcccgt    360
caaggagccc aagacaccta gtgcgaaaat gagtgtgatg ttgttcatca aagaggcgc    420 atgggcccat tcattcggcg caaacctgat cgcggtgtac atgactccga gattgactac    480
cagtccagct agaaacacac cttgctcgat gcggctttt gaagggtaga taagaccata    540
taccatttcc caagcaaagt tgcagcaaag agccagcggt gccatgctgt aagtctgttc    600
ctggagcgag gtgtagatca tgccggcgta gtttatgagc caacaaacgc ccattccgaa    660
gacgaagatg tccgaaatcc attcgacgcg ctgatattca acgggtgcat ggaacgatc    720 gaatccatcc at                                                        732
```

```
<210> SEQ ID NO 15
<211> LENGTH: 243
<212> TYPE: PRT
<213> ORGANISM: Hypoxylon pulicicidum

<400> SEQUENCE: 15

Met Asp Gly Phe Asp Arg Ser Asn Ala Pro Val Glu Tyr Gln Arg Val
1               5                   10                  15

Glu Trp Ile Ser Asp Ile Phe Val Phe Gly Met Gly Val Cys Trp Leu
            20                  25                  30

Ile Asn Tyr Ala Gly Met Ile Tyr Thr Ser Leu Gln Glu Gln Thr Tyr
        35                  40                  45

Ser Met Ala Pro Leu Ala Leu Cys Cys Asn Phe Ala Trp Glu Met Val
    50                  55                  60

Tyr Gly Leu Ile Tyr Pro Ser Lys Ser Arg Ile Glu Gln Gly Val Phe
65                  70                  75                  80

Leu Ala Gly Leu Val Val Asn Leu Gly Val Met Tyr Thr Ala Ile Arg
                85                  90                  95

Phe Ala Pro Asn Glu Trp Ala His Ala Pro Leu Val Met Asn Asn Ile
            100                 105                 110

Thr Leu Ile Phe Ala Leu Gly Val Leu Gly Ser Leu Thr Gly His Leu
        115                 120                 125

Ala Leu Ala Ala Glu Ile Gly Pro Ala Leu Gly Tyr Ser Trp Gly Ala
    130                 135                 140

Val Ala Cys Gln Leu Leu Leu Ser Val Gly Gly Phe Cys Gln Leu Leu
145                 150                 155                 160

Gly Arg Ser Ser Ser Arg Gly Ala Ser Tyr Thr Leu Trp Leu Ser Arg
                165                 170                 175

Phe Ile Gly Ser Gly Cys Val Val Gly Phe Ala Ile Leu Arg Tyr Met
            180                 185                 190

Tyr Trp Ser Glu Ala Phe Asn Trp Leu Asn Ser Pro Leu Val Leu Trp
        195                 200                 205

Ser Leu Gly Val Phe Ile Ala Val Asp Ser Leu Tyr Gly Ile Cys Leu
    210                 215                 220

Trp Asn Val Lys Lys Tyr Glu His Gly Gln Glu Arg Ser Asn Ala Arg
225                 230                 235                 240

Lys Ala Gln
```

<210> SEQ ID NO 16
<211> LENGTH: 1514
<212> TYPE: DNA
<213> ORGANISM: Hypoxylon pulicicidum

<400> SEQUENCE: 16

| | |
|---|---|
| atggaggttt cctcaagtga aacactcccc attctatgga gaacgagtcc tccctcaaac | 60 |
| gactatgaaa atgcaagatg cagagtgttc aatggcaggc agcctgagca cttcccccttt | 120 |
| gcaatagtca aggcaaacaa ggtcgagcat attgtagccg ccgtgaaact ggcagcagaa | 180 |
| ctagacgcct gtatcgccgt tcgttcgggc ggccacagcc tctcttgttg gactatacgc | 240 |
| catggggcga tccttattga cctcgaagat tatcagcact tgagctatga cgacgagatc | 300 |
| catgaagtgc aagcttcacc cagtacactt ggtgcggacc tacttacgtt ccttgcgaag | 360 |
| aaaaagaggt tctttcccgt aggtcactct ggagacattg gcttaggtgg ctatctcctt | 420 |
| cagggcggaa ttgggctcaa ttctcgggta tgaacgttga ccctacatac tcagtagctt | 480 |
| tcgaatactg acgatatctc tagggatatg ggtatgcctg tgaatacatt accgggcttg | 540 |
| atatcatcac cgctgatggt gaaatcaagc attgtgataa gacggaaaac tctgacccta t | 600 |
| actgggctgc tcgtggagct ggaccgggta agttcctcaa agctgtctgt accagtgtgt | 660 |
| aagagttcta ataaagcaga attccctgca atcgttatac ggttcttcct gaagacgtgc | 720 |
| cccctcttgc cggtgtgtaa gcggagtaga tacgtctggc cggcggccat gtatgggaag | 780 |
| gtttttaagt ggcttgaaga ggtaagttta atcccaagga tctaggacgg caggggttaa | 840 |
| tctgatccgc gtctttacag ctattgaatt ccttgagcga ggacgtcgag attgccgttt | 900 |
| tcgggtttgt attgccccga ctcaaccagc caggcttagt cctccatgca acagcatttg | 960 |
| gtgactctag cgagaatgtc cgggaaaagc tcacgcctat catcaaaaat catcctccag | 1020 |
| ggactttctt ggctgaagat ttcgtgagca ccaacttccc cgaagactac gacttaggta | 1080 |
| aggataccat gccgcggggc gctcgctatt ttaccgacag cgtctttctc aagcccggta | 1140 |
| tcgacttcgt cgcaacctgc aaaggaatgt ttacggagct caaacatccc cgtgcattgg | 1200 |
| cgtactggca accgatgaag accaatattg atcgcatcct tcccgatatg gcgatgagca | 1260 |
| tccatagtca tcattacgtg tcactacttg ccatctatga agaccccagt gaggaccaac | 1320 |
| agcaaatatc ctggatcata gatcgtatga aaagtcttga gccggcaatc ctgggaactt | 1380 |
| tcatagggga tgcacaccca gtggaaaggc catctaatta ttggtccgag gaagctgaag | 1440 |
| aacgggtgat cactattggg cggaagtggg accctagtag tagaattcgg ggtattgtgt | 1500 |
| tgagcgatgc ctaa | 1514 |

<210> SEQ ID NO 17
<211> LENGTH: 1347
<212> TYPE: DNA
<213> ORGANISM: Hypoxylon pulicicidum

<400> SEQUENCE: 17

| | |
|---|---|
| atggaggttt cctcaagtga aacactcccc attctatgga gaacgagtcc tccctcaaac | 60 |
| gactatgaaa atgcaagatg cagagtgttc aatggcaggc agcctgagca cttcccccttt | 120 |
| gcaatagtca aggcaaacaa ggtcgagcat attgtagccg ccgtgaaact ggcagcagaa | 180 |
| ctagacgcct gtatcgccgt tcgttcgggc ggccacagcc tctcttgttg gactatacgc | 240 |
| catggggcga tccttattga cctcgaagat tatcagcact tgagctatga cgacgagatc | 300 |

```
catgaagtgc aagcttcacc cagtacactt ggtgcggacc tacttacgtt ccttgcgaag    360
aaaaagaggt tctttcccgt aggtcactct ggagacattg gcttaggtgg ctatctcctt    420
cagggcggaa ttgggctcaa ttctcgggga tatgggtatg cctgtgaata cattaccggg    480
cttgatatca tcaccgctga tggtgaaatc aagcattgtg ataagacgga aaactctgac    540
ctatactggg ctgctcgtgg agctggaccg gaattccctg caatcgttat acggttcttc    600
ctgaagacgt gccccctctt gccggtgtgt aagcggagta gatacgtctg gccggcggcc    660
atgtatggga aggtttttaa gtggcttgaa gagctattga attccttgag cgaggacgtc    720
gagattgccg ttttcgggtt tgtattgccc cgactcaacc agccaggctt agtcctccat    780
gcaacagcat ttggtgactc tagcgagaat gtccgggaaa agctcacgcc tatcatcaaa    840
aatcatcctc cagggacttt cttggctgaa gatttcgtga gcaccaactt ccccgaagac    900
tacgacttag gtaaggatac catgccgcgg ggcgctcgct attttaccga cagcgtcttt    960
ctcaagcccg gtatcgactt cgtcgcaacc tgcaaaggaa tgtttacgga gctcaaacat   1020
ccccgtgcat tggcgtactg gcaaccgatg aagaccaata ttgatcgcat ccttcccgat   1080
atggcgatga gcatccatag tcatcattac gtgtcactac ttgccatcta tgaagacccc   1140
agtgaggacc aacagcaaat atcctggatc atagatcgta tgaaaagtct tgagccggca   1200
atcctgggaa ctttcatagg ggatgcacac ccagtggaaa ggccatctaa ttattggtcc   1260
gaggaagctg aagaacgggt gatcactatt gggcggaagt gggaccctag tagtagaatt   1320
cggggtattg tgttgagcga tgcctaa                                       1347
```

<210> SEQ ID NO 18
<211> LENGTH: 448
<212> TYPE: PRT
<213> ORGANISM: Hypoxylon pulicicidum

<400> SEQUENCE: 18

```
Met Glu Val Ser Ser Glu Thr Leu Pro Ile Leu Trp Arg Thr Ser
1               5                   10                  15

Pro Pro Ser Asn Asp Tyr Glu Asn Ala Arg Cys Arg Val Phe Asn Gly
            20                  25                  30

Arg Gln Pro Glu His Phe Pro Leu Ala Ile Val Lys Ala Asn Lys Val
        35                  40                  45

Glu His Ile Val Ala Ala Val Lys Leu Ala Ala Glu Leu Asp Ala Cys
    50                  55                  60

Ile Ala Val Arg Ser Gly Gly His Ser Leu Ser Cys Trp Thr Ile Arg
65                  70                  75                  80

His Gly Ala Ile Leu Ile Asp Leu Glu Asp Tyr Gln His Leu Ser Tyr
                85                  90                  95

Asp Asp Glu Ile His Glu Val Gln Ala Ser Pro Ser Thr Leu Gly Ala
            100                 105                 110

Asp Leu Leu Thr Phe Leu Ala Lys Lys Lys Arg Phe Phe Pro Val Gly
        115                 120                 125

His Ser Gly Asp Ile Gly Leu Gly Gly Tyr Leu Leu Gln Gly Gly Ile
    130                 135                 140

Gly Leu Asn Ser Arg Gly Tyr Gly Tyr Ala Cys Glu Tyr Ile Thr Gly
145                 150                 155                 160

Leu Asp Ile Ile Thr Ala Asp Gly Glu Ile Lys His Cys Asp Lys Thr
                165                 170                 175

Glu Asn Ser Asp Leu Tyr Trp Ala Ala Arg Gly Ala Gly Pro Glu Phe
            180                 185                 190
```

```
Pro Ala Ile Val Ile Arg Phe Phe Leu Lys Thr Cys Pro Leu Leu Pro
        195                 200                 205

Val Cys Lys Arg Ser Arg Tyr Val Trp Pro Ala Ala Met Tyr Gly Lys
210                 215                 220

Val Phe Lys Trp Leu Glu Glu Leu Leu Asn Ser Leu Ser Glu Asp Val
225                 230                 235                 240

Glu Ile Ala Val Phe Gly Phe Val Leu Pro Arg Leu Asn Gln Pro Gly
                245                 250                 255

Leu Val Leu His Ala Thr Ala Phe Gly Asp Ser Ser Glu Asn Val Arg
            260                 265                 270

Glu Lys Leu Thr Pro Ile Ile Lys Asn His Pro Pro Gly Thr Phe Leu
        275                 280                 285

Ala Glu Asp Phe Val Ser Thr Asn Phe Pro Glu Asp Tyr Asp Leu Gly
    290                 295                 300

Lys Asp Thr Met Pro Arg Gly Ala Arg Tyr Phe Thr Asp Ser Val Phe
305                 310                 315                 320

Leu Lys Pro Gly Ile Asp Phe Val Ala Thr Cys Lys Gly Met Phe Thr
                325                 330                 335

Glu Leu Lys His Pro Arg Ala Leu Ala Tyr Trp Gln Pro Met Lys Thr
            340                 345                 350

Asn Ile Asp Arg Ile Leu Pro Asp Met Ala Met Ser Ile His Ser His
        355                 360                 365

His Tyr Val Ser Leu Leu Ala Ile Tyr Glu Asp Pro Ser Glu Asp Gln
    370                 375                 380

Gln Gln Ile Ser Trp Ile Ile Asp Arg Met Lys Ser Leu Glu Pro Ala
385                 390                 395                 400

Ile Leu Gly Thr Phe Ile Gly Asp Ala His Pro Val Glu Arg Pro Ser
                405                 410                 415

Asn Tyr Trp Ser Glu Glu Ala Glu Glu Arg Val Ile Thr Ile Gly Arg
            420                 425                 430

Lys Trp Asp Pro Ser Ser Arg Ile Arg Gly Ile Val Leu Ser Asp Ala
        435                 440                 445
```

<210> SEQ ID NO 19
<211> LENGTH: 1694
<212> TYPE: DNA
<213> ORGANISM: Hypoxylon pulicicidum

<400> SEQUENCE: 19

```
ttacccaact agcagtggaa acttcgagtc gccttctgtg accctgaaat cccattcgtc      60
atccttgaat tcctttctct ctctgagagt caccatgaac tcccctgcag gtgtctgtat     120
ggaacttgca agtgttttca cgttggcctt gggaggaatc cactctccga gcacgggctc     180
catgtcaaac cgtaaaatca ccatggctac taccgctaat atctccccag atgcgaagtg     240
gcgcccagga cagatgttag gtgctgtccc gaaagactgg aacgcaacgc gtgtgacgtt     300
acggccactt cgcgatgtcc cactcttccc ctggccgaga tatcgatatg cgtcgaagct     360
atcccctgtt tcgccccata ctgactttc gcgattaaca catcttgcag ggatcacgat     420
cacggacccc ttcttgaata gaactcgctc gttgaggatg gtatcctcat ggaccatgcg     480
cgtgactata gcattagacc tcatacggag gacctcctga aggtaccga  aagcaaact     540
gcacttggcg cgtacagcgc tgagatcaat agtacgaact atccctccat cggtacctgg     600
atgcgtgtac acagcagaag ccacgagctc ttgtcgaaga tccctcagca aactcgggcg     660
```

```
tgagtaaatt tcgaaaaggg tccaaaatgt ggaaggcgca gtattcgata ggacacctat    720
cgcgttaaca atttccattc gagctatatc ttgtgtggtg attcccttgt tatattggac    780
ctcccatcga ccatacgtca ttttccgagga gttttcgtgg cctcccaggt tgtaatactc   840
tgttagagcg tccacaacct tacgacgatc atctagggac tttcgtgctg tgagaaaggg    900
aaggacattg aggattatca tattcatatt cgacgcgaaa tccctacacc acgtatgagc    960
tcagcaattc ttacacagca ttggggttct attctgtgct ttgacctacc aaaaagccct   1020
ttcaacttct atggatcgga atggattcat aggaccgtaa accgagtctg tgctcgccat   1080
tgtgatagaa cgtttacacc atgcaaataa gtcgaatgcc gcttgtttct ggctttggag   1140
ttcgtctatt gagggctta tagcctcgat catggaaaga ttcatggcat ccaagccatg    1200
tcctataagt gcgtgatgca tagcatgttg tagctcatcc acgatactac ctttaagcaa   1260
tttaagtcca ggcccactga caccacctac acgttctgcg gccagtgtaa attcgaacgt   1320
atcgaatcgt atattctggg actgtctttg aatagccggg actagctcgc tagacgtgat   1380
cacataaagc cttgatagtg gcatctggag cgagaaggcg ggaagtccat atttgtcact   1440
atctacaccg ttagtctatg tactatatac agcatatctt cctcgcttca actaagcaac   1500
atgtagaagt cttaaccata cttgagcttg gaaaaatacc caaagccgtc agtcgcgata   1560
ccaagtatgt gcccgatgag tggtaccgta ggggatatca aacggggctc gcggggggtcg  1620
agagcagctc tccatcgagt accgtacagc aggatgcaaa aagcgagagt tatgataata   1680
acgataagtt ccat                                                     1694

<210> SEQ ID NO 20
<211> LENGTH: 1545
<212> TYPE: DNA
<213> ORGANISM: Hypoxylon pulicicidum
<400> SEQUENCE: 20
ttacccaact agcagtggaa acttcgagtc gccttctgtg accctgaaat cccatttgtc     60
atccttgaat tcctttctct ctctgagagt caccatgaac tcccctgcag gtgtctgtat    120
ggaacttgca agtgttttca cgttggcctt gggaggaatc cactctccga gcacgggctc    180
catgtcaaac cgtaaaatca ccatggctac taccgctaat atctccccag atgcgaagtg    240
gcgcccagga cagatgttag gtgctgtccc gaaagactgg aacgcaacgc gtgtgacgtt    300
acggccactt cgcgatgtcc cactcttccc ctggccgaga tatcgatatg cgtcgaagct    360
atccctgtt tcgccccata ctgacttttc gcgattaaca catcttgcag ggatcacgat    420
cacggacccc ttcttgaata gaactcgctc gttgaggatg gtatcctcat ggaccatgcg    480
cgtgactata gcattagacc tcatacggag gacctcctga aggtaccgga gaagcaaact    540
gcacttggcg cgtacagcgc tgagatcaat agtacgaact atccctccat cggtacctgg    600
atgcgtgtac acagcagaag ccacgagctc ttgtcgaaga tccctcagca aactcgggcg    660
tgagtaaatt tcgaaaaggg tccaaaatgt ggaaggcgca gtattcgata ggacacctat    720
cgcgttaaca atttccattc gagctatatc ttgtgtggtg attcccttgt tatattggac    780
ctcccatcga ccatacgtca tttccgagga gttttcgtgg cctcccaggt tgtaatactc    840
tgttagagcg tccacaacct tacgacgatc atctagggac tttcgtgctg tgagaaaggg    900
aaggacattg aggattatca tattcatatt cgacgcgaaa tcccaaaaag ccctttcaac    960
ttctatggat cggaatggat tcataggacc gtaaaccgag tctgtgctcg ccattgtgat   1020
agaacgttta caccatgcaa ataagtcgaa tgccgcttgt ttctggcttt ggagttcgtc   1080
```

-continued

```
tattgagggc tttatagcct cgatcatgga aagattcatg gcatccaagc catgtcctat    1140
aagtgcgtga tgcatagcat gttgtagctc atccacgata ctacctttaa gcaatttaag    1200
tccaggccca ctgacaccac ctacacgttc tgcggccagt gtaaattcga acgtatcgaa    1260
tcgtatattc tgggactgtc tttgaatagc cgggactagc tcgctagacg tgatcacata    1320
aagccttgat agtggcatct ggagcgagaa ggcgggaagt ccatatttgt cattgagctt    1380
ggaaaaatac ccaaagccgt cagtcgcgat accaagtatg tgcccgatga gtggtaccgt    1440
aggggatatc aaacggggct cgcggggtc gagagcagct ctccatcgag taccgtacag     1500
caggatgcaa aaagcgagag ttatgataat aacgataagt ccat                     1545
```

<210> SEQ ID NO 21
<211> LENGTH: 514
<212> TYPE: PRT
<213> ORGANISM: Hypoxylon pulicicidum

<400> SEQUENCE: 21

```
Met Glu Leu Ile Val Ile Ile Thr Leu Ala Phe Cys Ile Leu Leu
1               5                   10                  15

Tyr Gly Thr Arg Trp Arg Ala Ala Leu Asp Pro Arg Glu Pro Arg Leu
            20                  25                  30

Ile Ser Pro Thr Val Pro Leu Ile Gly His Ile Leu Gly Ile Ala Thr
        35                  40                  45

Asp Gly Phe Gly Tyr Phe Ser Lys Leu Asn Asp Lys Tyr Gly Leu Pro
    50                  55                  60

Ala Phe Ser Leu Gln Met Pro Leu Ser Arg Leu Tyr Val Ile Thr Ser
65                  70                  75                  80

Ser Glu Leu Val Pro Ala Ile Gln Arg Gln Ser Gln Asn Ile Arg Phe
                85                  90                  95

Asp Thr Phe Glu Phe Thr Leu Ala Ala Glu Arg Val Gly Gly Val Ser
            100                 105                 110

Gly Pro Gly Leu Lys Leu Leu Lys Gly Ser Ile Val Asp Glu Leu Gln
        115                 120                 125

His Ala Met His His Ala Leu Ile Gly His Gly Leu Asp Ala Met Asn
    130                 135                 140

Leu Ser Met Ile Glu Ala Ile Lys Pro Ser Ile Asp Glu Leu Gln Ser
145                 150                 155                 160

Gln Lys Gln Ala Ala Phe Asp Leu Phe Ala Trp Cys Lys Arg Ser Ile
                165                 170                 175

Thr Met Ala Ser Thr Asp Ser Val Tyr Gly Pro Met Asn Pro Phe Arg
            180                 185                 190

Ser Ile Glu Val Glu Arg Ala Phe Trp Asp Phe Ala Ser Asn Met Asn
        195                 200                 205

Met Ile Ile Leu Asn Val Leu Pro Phe Leu Thr Ala Arg Lys Ser Leu
    210                 215                 220

Asp Asp Arg Arg Lys Val Asp Ala Leu Thr Glu Tyr Tyr Asn Leu
225                 230                 235                 240

Gly Gly His Glu Asn Ser Ser Glu Met Thr Tyr Gly Arg Trp Glu Val
                245                 250                 255

Gln Tyr Asn Lys Gly Ile Thr Thr Gln Asp Ile Ala Arg Met Glu Ile
            260                 265                 270

Val Asn Ala Ile Gly Val Leu Ser Asn Thr Ala Pro Ser Thr Phe Trp
        275                 280                 285
```

```
Thr Leu Phe Glu Ile Tyr Ser Arg Pro Ser Leu Leu Arg Asp Leu Arg
    290                 295                 300

Gln Glu Leu Val Ala Ser Ala Val Tyr Thr His Pro Gly Thr Asp Gly
305                 310                 315                 320

Gly Ile Val Arg Thr Ile Asp Leu Ser Ala Val Arg Ala Lys Cys Ser
                325                 330                 335

Leu Leu Leu Gly Thr Phe Gln Glu Val Leu Arg Met Arg Ser Asn Ala
                340                 345                 350

Ile Val Thr Arg Met Val His Glu Asp Thr Ile Leu Asn Glu Arg Val
            355                 360                 365

Leu Phe Lys Lys Gly Ser Val Ile Val Ile Pro Ala Arg Cys Val Asn
370                 375                 380

Arg Glu Lys Ser Val Trp Gly Glu Thr Gly Asp Ser Phe Asp Ala Tyr
385                 390                 395                 400

Arg Tyr Leu Gly Gln Gly Lys Ser Gly Thr Ser Arg Ser Gly Arg Asn
                405                 410                 415

Val Thr Arg Val Ala Phe Gln Ser Phe Gly Thr Ala Pro Asn Ile Cys
            420                 425                 430

Pro Gly Arg His Phe Ala Ser Gly Glu Ile Leu Ala Val Val Ala Met
                435                 440                 445

Val Ile Leu Arg Phe Asp Met Glu Pro Val Leu Gly Glu Trp Ile Pro
450                 455                 460

Pro Lys Ala Asn Val Lys Thr Leu Ala Ser Ser Ile Gln Thr Pro Ala
465                 470                 475                 480

Gly Glu Phe Met Val Thr Leu Arg Glu Arg Lys Glu Phe Lys Asp Asp
                485                 490                 495

Lys Trp Asp Phe Arg Val Thr Glu Gly Asp Ser Lys Phe Pro Leu Leu
                500                 505                 510

Val Gly

<210> SEQ ID NO 22
<211> LENGTH: 1125
<212> TYPE: DNA
<213> ORGANISM: Hypoxylon pulicicidum

<400> SEQUENCE: 22
atgtccttag gtttacagtg cttggcggca gtgttgtttt cggctttgtt ttcacttggg      60
gtcatcctag ttcatcttcc atggcgcgcc ttgaagtcaa aggacccgcg tgagcgaata     120
ttaggttcgc ccaaagaact ggttccaaca tgcccttacg aatatattcg aaatatatac     180
gggcgtcatc attgggcgcc ctttgtggcc aagttagcac cgaatctcaa agaaagtgat     240
tcagacaggt acacaatggt acttgaaatc atggactgca tacacctatg cctgattatg     300
gtcgatgatg tacgttcatc ttattatacg cctcttgttg gtgatagagg tgagagttgt     360
aaataactaa cccggactct cagattacag atgacagcga ctatcgtaaa ggccgcccag     420
cggcccatat catctatggc cgttcggaga cagctaaccg tgcttatctt cgtgtcagtc     480
agattataaa caagacaact caggacttcc cgcggctcgc cccgtgggtc acacagagtt     540
tggcagagat tctagagggc caggacatct cgctggtttg cgacgagac ggcctcacta     600 gctttccaaa agctcacgac gagcgcgtga ttgcttatcg gtgcatgtca tctttgaaga     660
ctggcgcgct ttttaggttg ctagggaggc ttgtcttgga aaatcgttcc atggatgaca     720
cattgagtca ggttgggtaa gtgaactgta tccatcctga actcgacccc ttcacagtg      780 gcggaagcca atgctaaaac gtctagatac tattcacaat tacaaaatga ctgcaaaaat     840
```

```
gttttctcat ccgagtacgc aaaggcaaaa ggtactttag ctgaggactt acggaaccga    900
gagctgacgt atcctatcat cttggccctc aatgagcctg aaggatttta tattgagaaa    960
gcctttgagt ctggctcccc tcgtgacata caaaatgcaa tcggtgtaat acagagtgaa   1020
aacgtatacc gtgcttgttt ggacgagttg aaacaatatg aatcgaacgt cagagagtgg   1080
gttacactat ggggtagaaa ggagaaactc gatcttacgc attga                   1125
```

<210> SEQ ID NO 23
<211> LENGTH: 981
<212> TYPE: DNA
<213> ORGANISM: Hypoxylon pulicicidum

<400> SEQUENCE: 23

```
atgtccttag gttacagtg cttggcggca gtgttgtttt cggctttgtt ttcacttggg     60
gtcatcctag ttcatcttcc atggcgcgcc ttgaagtcaa aggacccgcg tgagcgaata    120
ttaggttcgc ccaaagaact ggttccaaca tgcccttacg aatatattcg aaatatatac    180
gggcgtcatc attgggcgcc ctttgtggcc aagttagcac cgaatctcaa agaaagtgat    240
tcagacaggt acacaatggt acttgaaatc atggactgca tacacctatg cctgattatg    300
gtcgatgata ttacagatga cagcgactat cgtaaaggcc gcccagcggc ccatatcatc    360
tatggccgtt cggagacagc taaccgtgct tatcttcgtg tcagtcagat tataaacaag    420
acaactcagg acttcccgcg gctcgccccg tgggtcacac agagtttggc agagattcta    480
gagggccagg acatctcgct ggtttggcga cgagacggcc tcactagctt tccaaaagct    540
cacgacgagc gcgtgattgc ttatcggtgc atgtcatctt tgaagactgg cgcgcttttt    600
aggttgctag ggaggcttgt cttggaaaat cgttccatgg atgacacatt gagtcaggtt    660
ggatactatt cacaattaca aaatgactgc aaaaatgttt tctcatccga gtacgcaaag    720 gcaaaggta ctttagctga ggacttacgg aaccgagagc tgacgtatcc tatcatcttg    780
gccctcaatg agcctgaagg attttatatt gagaaagcct ttgagtctgg ctcccctcgt    840
gacatacaaa atgcaatcgg tgtaatacag agtgaaaacg tataccgtgc ttgtttggac    900
gagttgaaac aatatgaatc gaacgtcaga gagtgggtta cactatgggg tagaaaggag    960
aaactcgatc ttacgcattg a                                             981
```

<210> SEQ ID NO 24
<211> LENGTH: 326
<212> TYPE: PRT
<213> ORGANISM: Hypoxylon pulicicidum

<400> SEQUENCE: 24

```
Met Ser Leu Gly Leu Gln Cys Leu Ala Ala Val Leu Phe Ser Ala Leu
 1               5                  10                  15

Phe Ser Leu Gly Val Ile Leu Val His Leu Pro Trp Arg Ala Leu Lys
                20                  25                  30

Ser Lys Asp Pro Arg Glu Arg Ile Leu Gly Ser Pro Lys Glu Leu Val
            35                  40                  45

Pro Thr Cys Pro Tyr Glu Tyr Ile Arg Asn Ile Tyr Gly Arg His His
        50                  55                  60

Trp Ala Pro Phe Val Ala Lys Leu Ala Pro Asn Leu Lys Glu Ser Asp
65                  70                  75                  80

Ser Asp Arg Tyr Thr Met Val Leu Glu Ile Met Asp Cys Ile His Leu
                85                  90                  95
```

```
Cys Leu Ile Met Val Asp Asp Ile Thr Asp Asp Ser Asp Tyr Arg Lys
                100                 105                 110
Gly Arg Pro Ala Ala His Ile Ile Tyr Gly Arg Ser Glu Thr Ala Asn
            115                 120                 125
Arg Ala Tyr Leu Arg Val Ser Gln Ile Ile Asn Lys Thr Thr Gln Asp
        130                 135                 140
Phe Pro Arg Leu Ala Pro Trp Val Thr Gln Ser Leu Ala Glu Ile Leu
145                 150                 155                 160
Glu Gly Gln Asp Ile Ser Leu Val Trp Arg Arg Asp Gly Leu Thr Ser
                165                 170                 175
Phe Pro Lys Ala His Asp Glu Arg Val Ile Ala Tyr Arg Cys Met Ser
            180                 185                 190
Ser Leu Lys Thr Gly Ala Leu Phe Arg Leu Leu Gly Arg Leu Val Leu
        195                 200                 205
Glu Asn Arg Ser Met Asp Asp Thr Leu Ser Gln Val Gly Tyr Tyr Ser
210                 215                 220
Gln Leu Gln Asn Asp Cys Lys Asn Val Phe Ser Ser Glu Tyr Ala Lys
225                 230                 235                 240
Ala Lys Gly Thr Leu Ala Glu Asp Leu Arg Asn Arg Glu Leu Thr Tyr
                245                 250                 255
Pro Ile Ile Leu Ala Leu Asn Glu Pro Glu Gly Phe Tyr Ile Glu Lys
            260                 265                 270
Ala Phe Glu Ser Gly Ser Pro Arg Asp Ile Gln Asn Ala Ile Gly Val
        275                 280                 285
Ile Gln Ser Glu Asn Val Tyr Arg Ala Cys Leu Asp Glu Leu Lys Gln
290                 295                 300
Tyr Glu Ser Asn Val Arg Glu Trp Val Thr Leu Trp Gly Arg Lys Glu
305                 310                 315                 320
Lys Leu Asp Leu Thr His
                325

<210> SEQ ID NO 25
<211> LENGTH: 1439
<212> TYPE: DNA
<213> ORGANISM: Hypoxylon pulicicidum

<400> SEQUENCE: 25
ttaagagatg ttggtggcga cgtactcctt tccaccacga attgctttga cgaccttgtc      60
atattcctcg taggcatgct cctggctgtt gtgctctgaa acccagtccc taagtggcac     120
ttctgggtac atgttgatgc cctggtccgg ctgttccacg ttgtgctgaa gagctgaagc     180
tcgtggcttt cttttcggga gggaaagaaa tatgagttag ctaccgtacg tatctacgat     240
gttcttattg ttgttagact gctttacgta cctgattttc tcagccacac ggagcgcgag     300
agggacgttc cccttcctg cgagctcgag gcagattgcc acgactgcgg catcctcaat      360
gacaagagac tccccaatgg gagagtttag ggcggaaggg tgcgaagcgt cgccaatgag     420
aatcatgcgg ccctgaggag agacccatga tggaagctgt cccagctgaa gaacgggttc     480
atcaacaagg cttccagatg gcgcggcctg gacgaccgct tcgatgttgg ctttgaacgg     540
ccatgattgg atgggcttga ggaagtcttg tgcggtagca ggagttgatg acgtcttggc     600
tgagttagga gattcctaga agatactata agcaggtgct cgtccaacat gtacctcaag     660
aatacatacc accttgtaca tgttactaaa tgctacgttg cgaccacccc cacaagtgac     720
gatggtgaga caggcagttg gaccaggcac aaatatcatc tggtctactt cacccgctcc     780
```

```
ttggaggatc cattgggcgt ctgggtttcc ttttaggcta gcgatatcag ccctaccccg    840
gatgtgtgcg tatccgctgt gggttggctt gaggctggag cctgcgacgg agtctcggcc    900
tttgctgttc acaccatctg cccagatgat gcagtctgcc tgcagcttct ggccattggc    960
agagacgccg gcctgatcgc tctcctccca gtaatcagag atctcagttc cgaaccgcat   1020
gtcgattcca agagtcttcg catgatcgta acgatcttg gtcagctccc gtcggaggat   1080
caggtacttg ttgctcgatg gtttccgaac ttcaatggtc tgaacctgct ttccggtggt   1140
gtcatacaca gatgcttggg tgttattaaa cttccaagca ttcaaggcct gacccacagc   1200
tccgttgccc catttagaga caatcacacc cgcattgttg tcaatcatga cggtgtcatc   1260
tattatccta gtcattaaat tgctcttgat agtgtgagtg tatacttacc gacgtaattg   1320
agatccttgg accgttccag tgcaatgaca gaatgcccct tttggtgaca ttctatcgct   1380
gtggtaagac cagccaagcc aagtccaacc acaattacac taacaccggt tgaagccat   1439
```

<210> SEQ ID NO 26
<211> LENGTH: 1296
<212> TYPE: DNA
<213> ORGANISM: Hypoxylon pulicicidum

<400> SEQUENCE: 26

```
ttaagagatg ttggtggcga cgtactcctt tccaccacga attgctttga cgaccttgtc     60
atattcctcg taggcatgct cctggctgtt gtgctctgaa acccagtccc taagtggcac    120
ttctgggtac atgttgatgc cctggtccgg ctgttccacg ttgtgctgaa gagctgaagc    180
tcgtgggatg ttcttattgt tgttagactg ctttacgtac ctgattttct cagccacacg    240
gagcgcgaga gggacgttcc cctttcctgc gagctcgagg cagattgcca cgactgcggc    300
atcctcaatg acaagagact ccccaatggg agagtttagg gcggaagggt gcgaagcgtc    360
gccaatgaga atcatgcggc cctgaggaga gacccatgat ggaagctgtc ccagctgaag    420
aacgggttca tcaacaaggc ttccagatgg cgcggcctgg acgaccgctt cgatgttggc    480
tttgaacggc catgattgga tgggcttgag gaagtcttgt gcggtagcag gagttgatga    540
cgtcttggct gagttaggag attccaccct tgtacatgtt actaaatgct acgttgcgacc   600 accccacaa gtgacgatgg tgagacaggc agttggacca ggcacaaata tcatctggtc    660 tacttcacccc gctccttgga ggatccattg ggcgtctggg tttccttta ggctagcgat    720 atcagcccta ccccggatgt gtgcgtatcc gctgtgggtt ggcttgaggc tggagcctgc    780
gacggagtct cggcctttgc tgttcacacc atctgcccag atgatgcagt ctgcctgcag    840
cttctggcca ttggcagaga cgccggcctg atcgctctcc tcccagtaat cagagatctc    900
agttccgaac cgcatgtcga ttccaagagt cttcgcatga tcgtaaacga tcttggtcag   960
ctcccgtcgg aggatcaggt acttgttgct cgatggtttc cgaacttcaa tggtctgaac  1020
ctgctttccg gtggtgtcat acacagatgc ttgggtgtta ttaaacttcc aagcattcaa   1080
ggcctgaccc acagctccgt tgccccattt agagacaatc acaccccgcat gttgtcaat   1140 catgacggtg tcatctatta tcttaccgac gtaattgaga tccttggacc gttccagtgc   1200
aatgacagaa tgccccttt ggtgacattc tatcgctgtg gtaagaccag ccaagccaag   1260
tccaaccaca attcactaa caccggttga agccat                             1296
```

<210> SEQ ID NO 27
<211> LENGTH: 431
<212> TYPE: PRT
<213> ORGANISM: Hypoxylon pulicicidum

<400> SEQUENCE: 27

```
Met Ala Ser Thr Gly Val Ser Val Ile Val Val Gly Leu Gly Leu Ala
1               5                   10                  15

Gly Leu Thr Thr Ala Ile Glu Cys His Gln Lys Gly His Ser Val Ile
            20                  25                  30

Ala Leu Glu Arg Ser Lys Asp Leu Asn Tyr Val Gly Lys Ile Ile Asp
        35                  40                  45

Asp Thr Val Met Ile Asp Asn Asn Ala Gly Val Ile Val Ser Lys Trp
    50                  55                  60

Gly Asn Gly Ala Val Gly Gln Ala Leu Asn Ala Trp Lys Phe Asn Asn
65                  70                  75                  80

Thr Gln Ala Ser Val Tyr Asp Thr Thr Gly Lys Gln Val Gln Thr Ile
                85                  90                  95

Glu Val Arg Lys Pro Ser Ser Asn Lys Tyr Leu Ile Leu Arg Arg Glu
            100                 105                 110

Leu Thr Lys Ile Val Tyr Asp His Ala Lys Thr Leu Gly Ile Asp Met
        115                 120                 125

Arg Phe Gly Thr Glu Ile Ser Asp Tyr Trp Glu Glu Ser Asp Gln Ala
    130                 135                 140

Gly Val Ser Ala Asn Gly Gln Lys Leu Gln Ala Asp Cys Ile Ile Trp
145                 150                 155                 160

Ala Asp Gly Val Asn Ser Lys Gly Arg Asp Ser Val Ala Gly Ser Ser
                165                 170                 175

Leu Lys Pro Thr His Ser Gly Tyr Ala His Ile Arg Gly Arg Ala Asp
            180                 185                 190

Ile Ala Ser Leu Lys Gly Asn Pro Asp Ala Gln Trp Ile Leu Gln Gly
        195                 200                 205

Ala Gly Glu Val Asp Gln Met Ile Phe Val Pro Gly Pro Thr Ala Cys
    210                 215                 220

Leu Thr Ile Val Thr Cys Gly Gly Arg Asn Val Ala Phe Ser Asn
225                 230                 235                 240

Met Tyr Lys Val Glu Ser Pro Asn Ser Ala Lys Thr Ser Ser Thr Pro
                245                 250                 255

Ala Thr Ala Gln Asp Phe Leu Lys Pro Ile Gln Ser Trp Pro Phe Lys
            260                 265                 270

Ala Asn Ile Glu Ala Val Val Gln Ala Ala Pro Ser Gly Ser Leu Val
        275                 280                 285

Asp Glu Pro Val Leu Gln Leu Gly Gln Leu Pro Ser Trp Val Ser Pro
    290                 295                 300

Gln Gly Arg Met Ile Leu Ile Gly Asp Ala Ser His Pro Ser Ala Leu
305                 310                 315                 320

Asn Ser Pro Ile Gly Glu Ser Leu Val Ile Glu Asp Ala Ala Val Val
                325                 330                 335

Ala Ile Cys Leu Glu Leu Ala Gly Lys Gly Asn Val Pro Leu Ala Leu
            340                 345                 350

Arg Val Ala Glu Lys Ile Arg Tyr Val Lys Gln Ser Asn Asn Asn Lys
        355                 360                 365

Asn Ile Pro Arg Ala Ser Ala Leu Gln His Asn Val Glu Gln Pro Asp
    370                 375                 380

Gln Gly Ile Asn Met Tyr Pro Glu Val Pro Leu Arg Asp Trp Val Ser
385                 390                 395                 400

Glu His Asn Ser Gln Glu His Ala Tyr Glu Glu Tyr Asp Lys Val Val
```

405                 410                 415
Lys Ala Ile Arg Gly Gly Lys Glu Tyr Val Ala Thr Asn Ile Ser
            420                 425                 430

<210> SEQ ID NO 28
<211> LENGTH: 1372
<212> TYPE: DNA
<213> ORGANISM: Hypoxylon pulicicidum

<400> SEQUENCE: 28

| | | |
|---|---|---|
| atggactcta ccgggagaca gcctctcagc caggacgggc agccatggca agctcttgcc | 60 |
| tctggcttgg gatttccaga tgaagaccag aagtattggt ggtcagtcat ggcgccccta | 120 |
| ttaggggaac tgatgaaatg gccaactat cctgttgata acagtatct tgttcttgcg | 180 |
| ttctgccatg aatacatact tccattttgc ggacctcgtc caacggccga aggcggtatc | 240 |
| ttctggccca cgttgatcac caaggatggt actccgttcg agccgagcct aacttctac | 300 |
| aaaaataaag ccactctacg agttggatat gcgcctgcat gcgagctttc aggaagcaat | 360 |
| gacgaccta tcaatcaacg agccccaatt gcggcattgg agcaccaaaa gagagtccta | 420 |
| ccacagcaga atctcaaatg ggtggataat ttcaagaaag catggttcat cgataatgac | 480 |
| gacgcagtag ccttgaaggc acgcgtacat aacgagctct tgaacaggc agccgtccaa | 540 |
| tgcttgatag ttatgtgtt tccgactac acgcaggtca aggttgccat gagtcctctt | 600 |
| tggaagtcag tccagacagg ccagcaaatt cgcgagtga tctgggacac ctttcgccag | 660 |
| cttggagacg atgcttccag ttacctagat tgcctatcag tgctagagga gtatactgag | 720 |
| tctaaacagg ccaaactagc acaagtacag ccttccttcg tcaatttcga tgtgaatctg | 780 |
| aagggggact accagcagtc gcgacttaag gtatactatg ctacaccatg cactgcattc | 840 |
| gacacgatgg tccaggttt cactttgggc ggaaggctca agggccctga agttgaccat | 900 |
| gcgattgaat gccttcgtgt cctatggccc agcgtgcttg cagttcctga aaaccatccg | 960 |
| gacgaccaag acttgcctcg acggtaccac tctgtagcag tgacccagtt taacttcgag | 1020 |
| ctctggccgg gagcgaaact gcctgttccc cagatctatc tcccgactaa cttttacggt | 1080 |
| cgtgatgaat tggaaattgc ggagggccta gagggatttt tcaagactct ggctggagt | 1140 |
| gagcctttcc atgcctataa acagaattac attgcaacat ggttagtcta tcgcctttct | 1200 |
| ctcgctcatt gccctgatcc aatgaagtat tttactcaca cgatgtagtg ccacgcccga | 1260 |
| agggaaatgg aaagcgatcc aacacgacgt atcattctcg ttcaaggact caagcccata | 1320 |
| tgtgtcggtt tattataaac cagagctctc ggtcctatcc tcaccgtcgt ag | 1372 |

<210> SEQ ID NO 29
<211> LENGTH: 1305
<212> TYPE: DNA
<213> ORGANISM: Hypoxylon pulicicidum

<400> SEQUENCE: 29

| | | |
|---|---|---|
| atggactcta ccgggagaca gcctctcagc caggacgggc agccatggca agctcttgcc | 60 |
| tctggcttgg gatttccaga tgaagaccag aagtattggt ggtcagtcat ggcgccccta | 120 |
| ttaggggaac tgatgaaatg gccaactat cctgttgata acagtatct tgttcttgcg | 180 |
| ttctgccatg aatacatact tccattttgc ggacctcgtc caacggccga aggcggtatc | 240 |
| ttctggccca cgttgatcac caaggatggt actccgttcg agccgagcct aacttctac | 300 |
| aaaaataaag ccactctacg agttggatat gcgcctgcat gcgagctttc aggaagcaat | 360 |

```
gacgaccota tcaatcaacg agccccaatt gcggcattgg agcaccaaaa gagagtccta      420
ccacagcaga atctcaaatg ggtggataat ttcaagaaag catggttcat cgataatgac      480
gacgcagtag ccttgaaggc acgcgtacat aacgagctct tgaacaggc agccgtccaa       540 tgcttgatag gttatgtgtt ttccgactac acgcaggtca aggttgccat gagtcctctt      600
tggaagtcag tccagacagg ccagcaaatt tcgcgagtga tctgggacac ctttcgccag      660
cttggagacg atgcttccag ttacctagat tgcctatcag tgctagagga gtatactgag      720
tctaaacagg ccaaactagc acaagtacag ccttccttcg tcaatttcga tgtgaatctg      780 aaggggggact accagcagtc gcgacttaag gtatactatg ctacaccatg cactgcattc      840
gacacgatgg tccaggtttt cactttgggc ggaaggctca agggccctga agttgaccat      900
gcgattgaat gccttcgtgt cctatggccc agcgtgcttg cagttcctga aaaccatccg      960
gacgaccaag acttgcctcg acggtaccac tctgtagcag tgacccagtt taacttcgag     1020
ctctggccgg gagcgaaact gcctgttccc cagatctatc tcccgactaa cttttacggt     1080
cgtgatgaat tggaaattgc ggagggccta gagggatttt tcaagactct tggctggagt     1140
gagcctttcc atgcctataa acagaattac attgcaacat gtgccacgcc cgaagggaaa     1200
tggaaagcga tccaacacga cgtatcattc tcgttcaagg actcaagccc atatgtgtcg     1260
gtttattata aaccagagct ctcggtccta tcctcaccgt cgtag                     1305
```

<210> SEQ ID NO 30
<211> LENGTH: 434
<212> TYPE: PRT
<213> ORGANISM: Hypoxylon pulicicidum

<400> SEQUENCE: 30

```
Met Asp Ser Thr Gly Arg Gln Pro Leu Ser Gln Asp Gly Gln Pro Trp
1               5                   10                  15

Gln Ala Leu Ala Ser Gly Leu Gly Phe Pro Asp Glu Asp Gln Lys Tyr
            20                  25                  30

Trp Trp Ser Val Met Ala Pro Leu Leu Gly Glu Leu Met Lys Trp Ala
        35                  40                  45

Asn Tyr Pro Val Asp Lys Gln Tyr Leu Val Leu Ala Phe Cys His Glu
    50                  55                  60

Tyr Ile Leu Pro Phe Cys Gly Pro Arg Pro Thr Ala Glu Gly Gly Ile
65                  70                  75                  80

Phe Trp Pro Thr Leu Ile Thr Lys Asp Gly Thr Pro Phe Glu Pro Ser
                85                  90                  95

Leu Asn Phe Tyr Lys Asn Lys Ala Thr Leu Arg Val Gly Tyr Ala Pro
            100                 105                 110

Ala Cys Glu Leu Ser Gly Ser Asn Asp Asp Pro Ile Asn Gln Arg Ala
        115                 120                 125

Pro Ile Ala Ala Leu Glu His Gln Lys Arg Val Leu Pro Gln Gln Asn
    130                 135                 140

Leu Lys Trp Val Asp Asn Phe Lys Lys Ala Trp Phe Ile Asp Asn Asp
145                 150                 155                 160

Asp Ala Val Ala Leu Lys Ala Arg Val His Asn Glu Leu Phe Glu Gln
                165                 170                 175

Ala Ala Val Gln Cys Leu Ile Gly Tyr Val Phe Ser Asp Tyr Thr Gln
            180                 185                 190

Val Lys Val Ala Met Ser Pro Leu Trp Lys Ser Val Gln Thr Gly Gln
        195                 200                 205
```

Gln Ile Ser Arg Val Ile Trp Asp Thr Phe Arg Gln Leu Gly Asp Asp
        210                 215                 220

Ala Ser Ser Tyr Leu Asp Cys Leu Ser Val Leu Glu Glu Tyr Thr Glu
225                 230                 235                 240

Ser Lys Gln Ala Lys Leu Ala Gln Val Gln Pro Ser Phe Val Asn Phe
                245                 250                 255

Asp Val Asn Leu Lys Gly Asp Tyr Gln Gln Ser Arg Leu Lys Val Tyr
            260                 265                 270

Tyr Ala Thr Pro Cys Thr Ala Phe Asp Thr Met Val Gln Val Phe Thr
        275                 280                 285

Leu Gly Gly Arg Leu Lys Gly Pro Glu Val Asp His Ala Ile Glu Cys
290                 295                 300

Leu Arg Val Leu Trp Pro Ser Val Leu Ala Val Pro Glu Asn His Pro
305                 310                 315                 320

Asp Asp Gln Asp Leu Pro Arg Arg Tyr His Ser Val Ala Val Thr Gln
                325                 330                 335

Phe Asn Phe Glu Leu Trp Pro Gly Ala Lys Leu Pro Val Pro Gln Ile
            340                 345                 350

Tyr Leu Pro Thr Asn Phe Tyr Gly Arg Asp Glu Leu Glu Ile Ala Glu
        355                 360                 365

Gly Leu Glu Gly Phe Phe Lys Thr Leu Gly Trp Ser Glu Pro Phe His
370                 375                 380

Ala Tyr Lys Gln Asn Tyr Ile Ala Thr Cys Ala Thr Pro Glu Gly Lys
385                 390                 395                 400

Trp Lys Ala Ile Gln His Asp Val Ser Phe Ser Phe Lys Asp Ser Ser
                405                 410                 415

Pro Tyr Val Ser Val Tyr Tyr Lys Pro Glu Leu Ser Val Leu Ser Ser
            420                 425                 430

Pro Ser

<210> SEQ ID NO 31
<211> LENGTH: 1354
<212> TYPE: DNA
<213> ORGANISM: Hypoxylon pulicicidum

<400> SEQUENCE: 31

```
atggatgctg cttcaactct tacgcatgca ccggtatctc agccatggca gtccctagct      60
caagggttgg ggttcgtcaa tgagcatgaa gggtactggt ggtctaagct tggacctcct     120
ctcggtaaaa tgatgaactg gctcgatac tcgacatcgg aacagtacag agtcctagca      180
ttcctttaca aatatcttct ccctgcctgc ggcccaaagc ctggtgatga tggtgagctg     240
ttctggaagg ttttcatcag ctatgattac acgccattc agctcagtct caattttcac      300
aatggcaaaa tgacgctgcg caccgcgaac ataccaatta gcgataaatc gggaaccgca     360
gacgacccaa tcaaccaaca agcttcggta gacgccataa tccgccagga acgagtgttg     420
ccatcccagg atctacgttg gttcaaccac tttgcatccc agtacttctt cgacaaggac     480
acggcagcct ctctaaagac caaggtcgat aagctccgag tccagcaggg agttcagtgt     540
atgctgagcc acgactttcc tgagcgtgat gtccaatgca aagtggcttt ctgcccgctt     600
tggaaagccg tcgctacagg tctttccaac aaggagatca tctgggattc gattctaggg     660
ctcggagatg acatcatccc atacaagcga gcgcttgctg tccttgaaca gtacacatcg     720
tccgaaaatg cagcgaaagc aggagtgcga cctgtattct tcgctttcga tacggtgtta     780
aaagataatt acaagagctc tcgtatcaag atctactacc tcacaacacg gacagccttc     840
```

```
aactctatgg tcgacatcta cacacttgga ggcctgctaa aagggcctga tatccaaaaa    900
ggagtagagg cccttgaagt gctctggaaa gccgtcctca acgtcccga ggggtggccc    960 gatgataaag atctacccat gaatccacac cgttgtgcgg cagtaatctt caattttgag   1020
ctgtggccag gagcagagtt tccgagtccc aaggcctatc tcccagccca ttattatggc   1080
cggcctgatt tggagatagc tgatggtatg gactacttct tcaagcagca agggttggat   1140
ggggtatatg gttcttacaa ggagaactat ttgaagtgct gtacgacct cctcacctca    1200 ctcacatcta ccaagctatg gctaatagat cagaagtacg aactcacaga accaactcac   1260
agccctccac catgatattt cttttcatt caaagggtcc aatgcctacg ttacggtgta    1320
ctacaagccc gagctatctc tagataccga gtag                               1354

<210> SEQ ID NO 32
<211> LENGTH: 1302
<212> TYPE: DNA
<213> ORGANISM: Hypoxylon pulicicidum

<400> SEQUENCE: 32
atggatgctg cttcaactct tacgcatgca ccggtatctc agccatggca gtccctagct     60
caagggttgg ggttcgtcaa tgagcatgaa gggtactggt ggtctaagct tggacctcct    120
ctcggtaaaa tgatgaactg ggctcgatac tcgacatcgg aacagtacag agtcctagca    180
ttcctttaca aatatcttct ccctgcctgc ggcccaaagc ctggtgatga tggtgagctg    240
ttctggaagg ttttcatcag ctatgattac acgcccattc agctcagtct caattttcac    300
aatggcaaaa tgacgctgcg caccgcgaac ataccaatta gcgataaatc gggaaccgca    360
gacgacccaa tcaaccaaca agcttcggta gacgccataa tccgccagga acgagtgttg    420
ccatcccagg atctacgttg gttcaaccac tttgcatccc agtacttctt cgacaaggac    480
acggcagcct ctctaaagac caaggtcgat aagctccgag tccagcaggg agttcagtgt    540
atgctgagcc acgactttcc tgagcgtgat gtccaatgca aagtggcttt ctgcccgctt    600
tggaaagccg tcgctacagg tcttttccaac aaggagatca tctgggattc gattctaggg    660
ctcggagatg acatcatccc atacaagcga gcgcttgctg tccttgaaca gtacacatcg    720
tccgaaaatg cagcgaaagc aggagtgcga cctgtattct tcgctttcga tacggtgtta    780
aaagataatt acaagagctc tcgtatcaag atctactacc tcacaacacg acagccttc    840 aactctatgg tcgacatcta cacacttgga ggcctgctaa aagggcctga tatccaaaaa   900
ggagtagagg cccttgaagt gctctggaaa gccgtcctca acgtcccga ggggtggccc    960 gatgataaag atctacccat gaatccacac cgttgtgcgg cagtaatctt caattttgag   1020
ctgtggccag gagcagagtt tccgagtccc aaggcctatc tcccagccca ttattatggc   1080
cggcctgatt tggagatagc tgatggtatg gactacttct tcaagcagca agggttggat   1140
ggggtatatg gttcttacaa ggagaactat ttgaagtgct taagtacgaa ctcacagaac   1200
caactcacag ccctccacca tgatatttct ttttcattca aagggtccaa tgcctacgtt   1260
acggtgtact acaagcccga gctatctcta gataccgagt ag                      1302

<210> SEQ ID NO 33
<211> LENGTH: 433
<212> TYPE: PRT
<213> ORGANISM: Hypoxylon pulicicidum

<400> SEQUENCE: 33
```

```
Met Asp Ala Ala Ser Thr Leu Thr His Ala Pro Val Ser Gln Pro Trp
1               5                   10                  15

Gln Ser Leu Ala Gln Gly Leu Gly Phe Val Asn Glu His Glu Gly Tyr
            20                  25                  30

Trp Trp Ser Lys Leu Gly Pro Pro Leu Gly Lys Met Met Asn Trp Ala
        35                  40                  45

Arg Tyr Ser Thr Ser Glu Gln Tyr Arg Val Leu Ala Phe Leu Tyr Lys
    50                  55                  60

Tyr Leu Leu Pro Ala Cys Gly Pro Lys Pro Gly Asp Asp Gly Glu Leu
65                  70                  75                  80

Phe Trp Lys Val Phe Ile Ser Tyr Asp Tyr Thr Pro Ile Gln Leu Ser
                85                  90                  95

Leu Asn Phe His Asn Gly Lys Met Thr Leu Arg Thr Ala Asn Ile Pro
            100                 105                 110

Ile Ser Asp Lys Ser Gly Thr Ala Asp Asp Pro Ile Asn Gln Gln Ala
        115                 120                 125

Ser Val Asp Ala Ile Ile Arg Gln Glu Arg Val Leu Pro Ser Gln Asp
    130                 135                 140

Leu Arg Trp Phe Asn His Phe Ala Ser Gln Tyr Phe Phe Asp Lys Asp
145                 150                 155                 160

Thr Ala Ala Ser Leu Lys Thr Lys Val Asp Lys Leu Arg Val Gln Gln
                165                 170                 175

Gly Val Gln Cys Met Leu Ser His Asp Phe Pro Glu Arg Asp Val Gln
            180                 185                 190

Cys Lys Val Ala Phe Cys Pro Leu Trp Lys Ala Val Ala Thr Gly Leu
        195                 200                 205

Ser Asn Lys Glu Ile Ile Trp Asp Ser Ile Leu Gly Leu Gly Asp Asp
    210                 215                 220

Ile Ile Pro Tyr Lys Arg Ala Leu Ala Val Leu Glu Gln Tyr Thr Ser
225                 230                 235                 240

Ser Glu Asn Ala Ala Lys Ala Gly Val Arg Pro Val Phe Phe Ala Phe
                245                 250                 255

Asp Thr Val Leu Lys Asp Asn Tyr Lys Ser Ser Arg Ile Lys Ile Tyr
            260                 265                 270

Tyr Leu Thr Thr Arg Thr Ala Phe Asn Ser Met Val Asp Ile Tyr Thr
        275                 280                 285

Leu Gly Gly Leu Leu Lys Gly Pro Asp Ile Gln Lys Gly Val Glu Ala
    290                 295                 300

Leu Glu Val Leu Trp Lys Ala Val Leu Asn Val Pro Glu Gly Trp Pro
305                 310                 315                 320

Asp Asp Lys Asp Leu Pro Met Asn Pro His Arg Cys Ala Ala Val Ile
                325                 330                 335

Phe Asn Phe Glu Leu Trp Pro Gly Ala Glu Phe Pro Ser Pro Lys Ala
            340                 345                 350

Tyr Leu Pro Ala His Tyr Gly Arg Pro Asp Leu Glu Ile Ala Asp
        355                 360                 365

Gly Met Asp Tyr Phe Lys Gln Gln Gly Leu Asp Gly Val Tyr Gly
    370                 375                 380

Ser Tyr Lys Glu Asn Tyr Leu Lys Cys Leu Ser Thr Asn Ser Gln Asn
385                 390                 395                 400

Gln Leu Thr Ala Leu His His Asp Ile Ser Phe Ser Phe Lys Gly Ser
                405                 410                 415

Asn Ala Tyr Val Thr Val Tyr Tyr Lys Pro Glu Leu Ser Leu Asp Thr
```

420                425                430
Glu

<210> SEQ ID NO 34
<211> LENGTH: 1562
<212> TYPE: DNA
<213> ORGANISM: Hypoxylon pulicicidum

<400> SEQUENCE: 34

```
atggcgcctg atagacttgg tcccgagggc acagcacgcc ccaattccag tggcatctca    60
gttatcgtgg tcggccttgg aattgctggc ctaacagctg caattgagtg ccaccggaag   120
ggccattcag tcattgcctt cgagcgaatg aaggatgtcg aaccctttgg tgagtttggc   180
ttcgaatccc catattggtt actccgccaa cctagtaaag gcgatagcat catcatcggc   240
agcaacggcg gccgtatttt cggcaaatgg ggccgcggtg aggtacgcaa tgctatgcaa   300
gcctggcgat atacgcctac ccatgccgac atttacgata ccgccggaag attcatggcc   360
cagtctgaga ttcccaaagc tgcggatgac atgtacttca ctcttcgagg cagactagcg   420
aagaccttct acgaacacgc acaaagcctc ggcattgata tgaggatggg gtcgaaagtg   480
actgaatttt gggaagacag caatcgggct ggaatcgttg tggaaggaga gaggtttgag   540
gccgactgtg ttatttgcgc tgatggcata cacagcaagt ctcgctcctt gttcacttct   600
ctaaacgctc aaccatttcg ttctggtttc tctattttca gggggaaagc ggacgctaat   660
gcgattattg ccgatcccga tgcgaaatgg atccttgacc agacagagaa caccgatcag   720
ttcaaagtgt ttctggggaa ggagatctgt gttgtcataa ttacctgcgg gctaggccgt   780
gcagtggtct gcagtgctat gcataggggtg agcaataccct atctcccaga taccaataat   840
atatagcagg taggctttgg actatatctt cctgttctgc tcacacaaga ctgccccagg   900
acctaaatga agcggaacag tcgtggtcga cccatgccaa cccggatgat ctattggacg   960
ccatcaaaga ctgccgtgc aggcgccaga tcgaaccaat cgttcggaag atatccgaag  1020
accagttcat cgactatccc cttctaactg tgtctccact ggacacgtgg gtatcccagc  1080
acgggcggat gattctaata ggagatgctg ctcatccatt cttttccgact ccggacaag  1140
gaggcgcaca agccatggag gatgcagctg tgcttgcaat ttgcctcgag ttggcaggga  1200
aaggaaacat ccccctggct cttcatgcaa cagaaaagat caggtctagt ttcccggccc  1260
ttcgggctac tctccctttc catttttatcc gttttccttta ctttcgctaa taccacgtaa  1320
cttccagaaa gagccgagct tcagtcctcc aactaaacag gacgtattca gaagggggttc  1380
aactagcacc tgcgctgccg aaatccaaag acagtatgtc tgttccaaat gttccagtaa  1440
tggattggat ctggcatcac tgctgccagt cctacgcata tgatgagttc gacaaggtag  1500
cggaggcgat tcaaagcggg agtgaataca ttccacataa tcttccagaa gatggtacgt  1560
ag                                                                1562
```

<210> SEQ ID NO 35
<211> LENGTH: 1386
<212> TYPE: DNA
<213> ORGANISM: Hypoxylon pulicicidum

<400> SEQUENCE: 35

```
atggcgcctg atagacttgg tcccgagggc acagcacgcc ccaattccag tggcatctca    60
gttatcgtgg tcggccttgg aattgctggc ctaacagctg caattgagtg ccaccggaag   120
ggccattcag tcattgcctt cgagcgaatg aaggatgtcg aaccctttgg tgagtttggc   180
```

-continued

```
ttcgaatccc catattggtt actccgccaa cctagtaaag gcgatagcat catcatcggc    240
agcaacggcg gccgtatttt cggcaaatgg ggccgcggtg aggtacgcaa tgctatgcaa    300
gcctggcgat atacgcctac ccatgccgac atttacgata ccgccggaag attcatggcc    360
cagtctgaga ttcccaaagc tgcggatgac atgtacttca ctcttcgagg cagactagcg    420
aagaccttct acgaacacgc acaaagcctc ggcattgata tgaggatggg gtcgaaagtg    480
actgaatttt gggaagacag caatcgggct ggaatcgttg tggaaggaga gaggtttgag    540
gccgactgtg ttatttgcgc tgatggcata cacagcaagt ctcgctcctt gttcacttct    600
ctaaacgctc aaccatttcg ttctggtttc tctattttca gggggaaagc ggacgctaat    660
gcgattattg ccgatcccga tgcgaaatgg atccttgacc agacagagaa caccgatcag    720
ttcaaagtgt tctggggaa ggagatctgt gttgtcataa ttacctgcgg gctaggccgt     780
gcagtggtct gcagtgctat gcatagggac ctaaatgaag cggaacagtc gtggtcgacc    840
catgccaacc cggatgatct attggacgcc atcaaagact ggccgtgcag gcgccagatc    900
gaaccaatcg ttcggaagat atccgaagac cagttcatcg actatcccct tctaactgtg    960
tctccactgg acacgtgggt atcccagcac gggcggatga ttctaatagg agatgctgct   1020
catccattct ttccgacttc cggacaagga ggcgcacaag ccatggagga tgcagctgtg   1080
cttgcaattt gcctcgagtt ggcagggaaa ggaaacatcc ccctggctct tcatgcaaca   1140
gaaaagatca gaaagagccg agcttcagtc ctccaactaa acaggacgta ttcagaaggg   1200
gttcaactag cacctgcgct gccgaaatcc aaagacagta tgtctgttcc aaatgttcca   1260
gtaatggatt ggatctggca tcactgctgc cagtcctacg catatgatga gttcgacaag   1320
gtagcggagg cgattcaaag cgggagtgaa tacattccac ataatcttcc agaagatggt   1380
acgtag                                                              1386
```

<210> SEQ ID NO 36
<211> LENGTH: 461
<212> TYPE: PRT
<213> ORGANISM: Hypoxylon pulicicidum

<400> SEQUENCE: 36

```
Met Ala Pro Asp Arg Leu Gly Pro Glu Gly Thr Ala Arg Pro Asn Ser
1               5                   10                  15

Ser Gly Ile Ser Val Ile Val Gly Leu Gly Ile Ala Gly Leu Thr
            20                  25                  30

Ala Ala Ile Glu Cys His Arg Lys Gly His Ser Val Ile Ala Phe Glu
        35                  40                  45

Arg Met Lys Asp Val Glu Pro Phe Gly Glu Phe Gly Phe Glu Ser Pro
    50                  55                  60

Tyr Trp Leu Leu Arg Gln Pro Ser Lys Gly Asp Ser Ile Ile Ile Gly
65                  70                  75                  80

Ser Asn Gly Gly Arg Ile Phe Gly Lys Trp Gly Arg Gly Glu Val Arg
                85                  90                  95

Asn Ala Met Gln Ala Trp Arg Tyr Thr Pro Thr His Ala Asp Ile Tyr
            100                 105                 110

Asp Thr Ala Gly Arg Phe Met Ala Gln Ser Glu Ile Pro Lys Ala Ala
        115                 120                 125

Asp Asp Met Tyr Phe Thr Leu Arg Gly Arg Leu Ala Lys Thr Phe Tyr
    130                 135                 140

Glu His Ala Gln Ser Leu Gly Ile Asp Met Arg Met Gly Ser Lys Val
```

```
                    145                 150                 155                 160
            Thr Glu Phe Trp Glu Asp Ser Asn Arg Ala Gly Ile Val Val Glu Gly
                            165                 170                 175
            Glu Arg Phe Glu Ala Asp Cys Val Ile Cys Ala Asp Gly Ile His Ser
                        180                 185                 190
            Lys Ser Arg Ser Leu Phe Thr Ser Leu Asn Ala Gln Pro Phe Arg Ser
                    195                 200                 205
            Gly Phe Ser Ile Phe Arg Gly Lys Ala Asp Ala Asn Ala Ile Ile Ala
                210                 215                 220
            Asp Pro Asp Ala Lys Trp Ile Leu Asp Gln Thr Glu Asn Thr Asp Gln
            225                 230                 235                 240
            Phe Lys Val Phe Leu Gly Lys Glu Ile Cys Val Ile Ile Thr Cys
                            245                 250                 255
            Gly Leu Gly Arg Ala Val Val Cys Ser Ala Met His Arg Asp Leu Asn
                        260                 265                 270
            Glu Ala Glu Gln Ser Trp Ser Thr His Ala Asn Pro Asp Asp Leu Leu
                    275                 280                 285
            Asp Ala Ile Lys Asp Trp Pro Cys Arg Arg Gln Ile Glu Pro Ile Val
                290                 295                 300
            Arg Lys Ile Ser Glu Asp Gln Phe Ile Asp Tyr Pro Leu Leu Thr Val
            305                 310                 315                 320
            Ser Pro Leu Asp Thr Trp Val Ser Gln His Gly Arg Met Ile Leu Ile
                            325                 330                 335
            Gly Asp Ala Ala His Pro Phe Phe Pro Thr Ser Gly Gln Gly Gly Ala
                        340                 345                 350
            Gln Ala Met Glu Asp Ala Ala Val Leu Ala Ile Cys Leu Glu Leu Ala
                    355                 360                 365
            Gly Lys Gly Asn Ile Pro Leu Ala Leu His Ala Thr Glu Lys Ile Arg
                370                 375                 380
            Lys Ser Arg Ala Ser Val Leu Gln Leu Asn Arg Thr Tyr Ser Glu Gly
            385                 390                 395                 400
            Val Gln Leu Ala Pro Ala Leu Pro Lys Ser Lys Asp Ser Met Ser Val
                            405                 410                 415
            Pro Asn Val Pro Val Met Asp Trp Ile Trp His His Cys Cys Gln Ser
                        420                 425                 430
            Tyr Ala Tyr Asp Glu Phe Asp Lys Val Ala Glu Ala Ile Gln Ser Gly
                    435                 440                 445
            Ser Glu Tyr Ile Pro His Asn Leu Pro Glu Asp Gly Thr
                450                 455                 460

<210> SEQ ID NO 37
<211> LENGTH: 1844
<212> TYPE: DNA
<213> ORGANISM: Hypoxylon pulicicidum

<400> SEQUENCE: 37
atgataacag catccacttc cgtgtttggt ggcttaatcc ttgcctttat cttctcactt      60
ttatataaga ataagaagac ccgtatccca gcagaaatcg accgcgtaag gacgggaggt     120
ttcctagcac acattagagc ctttgggtgc aggttaggta cgcgagttga tgatattcgc     180
aatggatata ataaggttag ttgctcctat agctgctcac aacaaatact caacacatga     240
tatctcaata cgcagttcaa caaaaacggt aagccgtttg tgatccagga ttctaccttt     300
atcccacagg tcgtcatacc acctcaatac ctgggatggt tgaaggagca accagagaag     360
```

-continued

```
gctctttctg cagaaaccgt gaggctagaa cagcttggac ttcgctattt ggtccctagc    420
tcagatcccg agatggtcca tttgttgaca gacgtcgtgt gtcgctatct tacccgcaat    480
tttcaaagag tacaagagcg tttatatgag gagctccata tgagtacgga tgaaatcatg    540
gggctggagg caactgagtg gcgtcagatt tgtctccatg aagcgatgga acgattctt     600 cgaaggatga ttagttgcgt cctgattggt ctcccatggt gtcgagatga ggaatgctta    660
aaatcgtgga ccggatttct tcactgcatg gccattgcag gaactattct aggggcagta    720
acaccttggt tcctacggcc actcctcgga ctactgctca agccgcccgt tggctatatg    780
cgcagaagat cactgcgtta tcttactccg atctttactg aaagatggaa aaaaattgag    840
aagcatgaga agagctcact gacgacgcgt gagctgccgg atgacttcgt aacatggtgt    900
attcaggagg tacggaatgg taatatgaaa gaaaaacacg atgctcttag ccttgcgtcg    960
gaatttctat tctttgtgag tcactctacg cgttggtatc atggtttccc atattcaata   1020
cgcgatgcga tggatcgagg ctctaacgag aacgcagtcg atcgcattct ttgacgcgcc   1080
tataggagct gcagaagtca ccatgctcga tcttctaagt gcggatccca aataggtta    1140 ctgggaaaag cttgtggaag aagccactac tgcattcaga acagacgagg actggattca   1200
tgcaggcact gtgtcaaaat tggcatacac ggacagcgca atcagggagt ctctacgccg   1260 aaacccttc agcatccgaa acgtgacccg agaggtgata ggaaaagatg gctaacact     1320 gccatccggt acgcgtctgc cacagggcac ttggatcacg accgctctcg ccaatataca   1380
tcatgatgca agattttact caaatcccac cgaataccag cctttccgtt ttgtggccag   1440
agacgcgttt cacacagagg ggaaagaggg tagcgaaaag gttttacagc cctctgaagc   1500
tatcttgacg agcacaattg atgaaaggct cttgacattc ggatatgggc gtcgagcatg   1560
gtacgaaatc caactgtctc ctagagtctc aaactcttat atcctgtctc cagtcgaacc   1620
tacctaggta ctaatgcttt tgcaattact gtagccccgg ccgatggttc gcttcacaca   1680
tactgaaaat gttgatcgcg tatatcacga tcaattatga catacagccc ttgacgggac   1740
cgccgaaaaa agtcaaattc gcagatttca ccgtgccatc gccgagtatc aaaatcattg   1800
tgcgccggaa gaatctcgct taccttaggc aacgtgagcg ttga                    1844
```

<210> SEQ ID NO 38
<211> LENGTH: 1524
<212> TYPE: DNA
<213> ORGANISM: Hypoxylon pulicicidum

<400> SEQUENCE: 38

```
atgataacag catccacttc cgtgtttggt ggcttaatcc ttgcctttat cttctcactt     60
ttatataaga ataagaagac ccgtatccca gcagaaatcg accgcgtaag gacgggaggt    120
ttcctagcac acattagagc ctttgggtgc aggttaggta cgcgagttga tgatattcgc    180
aatggatata ataagttcaa caaaaacggt aagccgtttg tgatccagga ttctaccttt    240
atcccacagg tcgtcatacc acctcaatac ctgggatggt tgaaggagca accagagaag    300
gctctttctg cagaaaccgt gaggctagaa cagcttggac ttcgctattt ggtccctagc    360
tcagatcccg agatggtcca tttgttgaca gacgtcgtgt gtcgctatct tacccgcaat    420
tttcaaagag tacaagagcg tttatatgag gagctccata tgagtacgga tgaaatcatg    480
gggctggagg caactgagtg gcgtcagatt tgtctccatg aagcgatgga acgattctt     540 cgaaggatga ttagttgcgt cctgattggt ctcccatggt gtcgagatga ggaatgctta    600
aaatcgtgga ccggatttct tcactgcatg gccattgcag gaactattct aggggcagta    660
```

```
acaccttggt tcctacggcc actcctcgga ctactgctca agccgcccgt tggctatatg    720
cgcagaagat cactgcgtta tcttactccg atctttactg aaagatggaa aaaaattgag    780
aagcatgaga agagctcact gacgacgcgt gagctgccgg atgacttcgt aacatggtgt    840
attcaggagg tacggaatgg agctgcagaa gtcaccatgc tcgatcttct aagtgcggat    900
cccacaatag gttactggga aaagcttgtg gaagaagcca ctactgcatt cagaacagac    960
gaggactgga ttcatgcagg cactgtgtca aaattggcat acacggacag cgcaatcagg   1020
gagtctctac gccgaaaccc tttcagcatc cgaaacgtga cccgagaggt gataggaaaa   1080
gatgggctaa cactgccatc cggtacgcgt ctgccacagg gcacttggat cacgaccgct   1140
ctcgccaata tacatcatga tgcaagattt tactcaaatc ccaccgaata ccagcctttc   1200
cgttttgtgg ccagagacgc gtttcacaca gaggggaaag agggtagcga aaaggtttta   1260
cagccctctg aagctatctt gacgagcaca attgatgaaa ggctcttgac attcggatat   1320
gggcgtcgag catgccccgg ccgatggttc gcttcacaca tactgaaaat gttgatcgcg   1380
tatatcacga tcaattatga catacagccc ttgacgggac cgccgaaaaa agtcaaattc   1440
gcagatttca ccgtgccatc gccgagtatc aaaatcattg tgcgccggaa gaatctcgct   1500
taccttaggc aacgtgagcg ttga                                          1524
```

<210> SEQ ID NO 39
<211> LENGTH: 507
<212> TYPE: PRT
<213> ORGANISM: Hypoxylon pulicicidum

<400> SEQUENCE: 39

```
Met Ile Thr Ala Ser Thr Ser Val Phe Gly Gly Leu Ile Leu Ala Phe
1               5                   10                  15

Ile Phe Ser Leu Leu Tyr Lys Asn Lys Lys Thr Arg Ile Pro Ala Glu
            20                  25                  30

Ile Asp Arg Val Arg Thr Gly Gly Phe Leu Ala His Ile Arg Ala Phe
        35                  40                  45

Gly Cys Arg Leu Gly Thr Arg Val Asp Asp Ile Arg Asn Gly Tyr Asn
    50                  55                  60

Lys Phe Asn Lys Asn Gly Lys Pro Phe Val Ile Gln Asp Ser Thr Phe
65                  70                  75                  80

Ile Pro Gln Val Val Ile Pro Pro Gln Tyr Leu Gly Trp Leu Lys Glu
                85                  90                  95

Gln Pro Glu Lys Ala Leu Ser Glu Thr Val Arg Leu Glu Gln Leu
            100                 105                 110

Gly Leu Arg Tyr Leu Val Pro Ser Ser Asp Pro Glu Met Val His Leu
        115                 120                 125

Leu Thr Asp Val Val Cys Arg Tyr Leu Thr Arg Asn Phe Gln Arg Val
    130                 135                 140

Gln Glu Arg Leu Tyr Glu Glu Leu His Met Ser Thr Asp Glu Ile Met
145                 150                 155                 160

Gly Leu Glu Ala Thr Glu Trp Arg Gln Ile Cys Leu His Glu Ala Met
                165                 170                 175

Glu Thr Ile Leu Arg Arg Met Ile Ser Cys Val Leu Ile Gly Leu Pro
            180                 185                 190

Trp Cys Arg Asp Glu Glu Cys Leu Lys Ser Trp Thr Gly Phe Leu His
        195                 200                 205

Cys Met Ala Ile Ala Gly Thr Ile Leu Gly Ala Val Thr Pro Trp Phe
```

```
        210                 215                 220
Leu Arg Pro Leu Leu Gly Leu Leu Lys Pro Pro Val Gly Tyr Met
225                 230                 235                 240

Arg Arg Arg Ser Leu Arg Tyr Leu Thr Pro Ile Phe Thr Glu Arg Trp
            245                 250                 255

Lys Lys Ile Glu Lys His Glu Lys Ser Ser Leu Thr Thr Arg Glu Leu
                260                 265                 270

Pro Asp Asp Phe Val Thr Trp Cys Ile Gln Glu Val Arg Asn Gly Ala
            275                 280                 285

Ala Glu Val Thr Met Leu Asp Leu Leu Ser Ala Asp Pro Thr Ile Gly
        290                 295                 300

Tyr Trp Glu Lys Leu Val Glu Glu Ala Thr Thr Ala Phe Arg Thr Asp
305                 310                 315                 320

Glu Asp Trp Ile His Ala Gly Thr Val Ser Lys Leu Ala Tyr Thr Asp
                325                 330                 335

Ser Ala Ile Arg Glu Ser Leu Arg Arg Asn Pro Phe Ser Ile Arg Asn
                340                 345                 350

Val Thr Arg Glu Val Ile Gly Lys Asp Gly Leu Thr Leu Pro Ser Gly
            355                 360                 365

Thr Arg Leu Pro Gln Gly Thr Trp Ile Thr Thr Ala Leu Ala Asn Ile
370                 375                 380

His His Asp Ala Arg Phe Tyr Ser Asn Pro Thr Glu Tyr Gln Pro Phe
385                 390                 395                 400

Arg Phe Val Ala Arg Asp Ala Phe His Thr Glu Gly Lys Glu Gly Ser
            405                 410                 415

Glu Lys Val Leu Gln Pro Ser Glu Ala Ile Leu Thr Ser Thr Ile Asp
                420                 425                 430

Glu Arg Leu Leu Thr Phe Gly Tyr Gly Arg Arg Ala Cys Pro Gly Arg
            435                 440                 445

Trp Phe Ala Ser His Ile Leu Lys Met Leu Ile Ala Tyr Ile Thr Ile
        450                 455                 460

Asn Tyr Asp Ile Gln Pro Leu Thr Gly Pro Pro Lys Lys Val Lys Phe
465                 470                 475                 480

Ala Asp Phe Thr Val Pro Ser Pro Ser Ile Lys Ile Val Arg Arg
            485                 490                 495

Lys Asn Leu Ala Tyr Leu Arg Gln Arg Glu Arg
                500                 505

<210> SEQ ID NO 40
<211> LENGTH: 1294
<212> TYPE: DNA
<213> ORGANISM: Penicillium paxilli

<400> SEQUENCE: 40
ttaaactctt cctttctcat tagtagggta ctccacttca agtagatcga gaatcttatg     60
aattccagga ttgggcccta aggaagtctc cagcttcttt acatagccac gagcctccgc    120
actaagtcga cttagggtct ccctagtata ttggaagctc cccgtcgact ccatgatctt    180
cacagcccgg attttgactg cttcgtcctc tgtgcgttgc tttagaatat cgagaagctc    240
ggagctctct ggagatgcac ggatgctgtg tatgatagga taggagaact tcccctccgt    300
caaatcttcc atcagccctt ttttctcagc atagagtccg ctctgcagat tcatatagtc    360
atcacgaatt tggaatataa cacccaatag ctcgacaagt ttagaaaagt cactgtaaaa    420
tactaattag cattgctgcg aagtgaccgt tatggattag aaacttacgt attcttgcgg    480
```

```
gattggatac gcatcaaatc gagggccagg ttgaaaagac ctccagtttt gtacataacc      540
atccgggtgt attcctcctc ggtcggacaa accaccatat cacgccaata taggtccatg      600
ccctggccaa gatgtagatc tagcagtgac cttgtaaata tttcgaaggc gcggggtct       660 ccaatctctt tcaatcttgc ttgttggaga tagtaggcat agttggctga gttgatagtt      720
tgtgctacac cgtatacatc atgagccaca ggctttcctc tccggagccg tgatgcatct      780
tgaatatcat cgatactata atcaccatga tgttagaata gaacaggagc gctgggttg       840 gaaatctcac agaagggatg cagtgtgaag taagtttatt atatctttca caatagacaa      900
cttctcctct ggaagctgga gccatatgtt gaaggagtcg atcagcttgc ttcggatgtc      960
ttttcccgga atcgctagaa gatagtctag aggtccacga acaatctaag aagaacaaac     1020
gattggtata atgaaacaca aggggaatcc caagagcaat gacagaactg accttgttat     1080
actgaatagc aatatcgtca acgtcatctt ctagcacctg cactgttcta atcgtgcttg     1140
gtgctttgct ggaatcactc aggagtcttg ggaatccttg gaagtttgat tcccagtaat     1200
tatcagcaga taatgagtgt gaagctcccc aataattaag atgagatatt cctcgacgaa     1260
cgaagttcag agcttctgca aggatgtagg acat                                 1294

<210> SEQ ID NO 41
<211> LENGTH: 1116
<212> TYPE: DNA
<213> ORGANISM: Penicillium paxilli

<400> SEQUENCE: 41
ttaaactctt cctttctcat tagtagggta ctccacttca agtagatcga gaatcttatg       60
aattccagga ttgggcccta aggaagtctc cagcttcttt acatagccac gagcctccgc      120
actaagtcga cttagggtct ccctagtata ttggaagctc cccgtcgact ccatgatctt      180
cacagcccgg attttgactg cttcgtcctc tgtgcgttgc tttagaatat cgagaagctc      240
ggagctctct ggagatgcac ggatgctgtg tatgatagga taggagaact tcccctccgt      300
caaatcttcc atcagccctt ttttctcagc atagagtccg ctctgcagat tcatatagtc      360
atcacgaatt tggaatataa cacccaatag ctcgacaagt ttagaaaagt cagtattctt      420
gcgggattgg atacgcatca aatcgagggc caggttgaaa agacctccag tttttgtacat      480 aaccatccgg gtgtattcct cctcggtcgg acaaaccacc atatcacgcc aatataggtc      540 catgcccctgg ccaagatgta gatctagcag tgaccttgta aatatttcga aggcgcgggg      600
gtctccaatc tctttcaatc ttgcttgttg gagatagtag gcatagttgg ctgagttgat      660
agtttgtgct acaccgtata catcatgagc cacaggcttt cctctccgga gccgtgatgc      720
atcttgaata tcatcgataa gaagggatgc agtgtgaagt aagtttatta tatctttcac      780
aatagacaac ttctcctctg gaagctggag ccatatgttg aaggagtcga tcagcttgct      840
tcggatgtct tttcccggaa tcgctagaag atagtctaga ggtccacgaa caatcttgtt      900
atactgaata gcaatatcgt caacgtcatc ttctagcacc tgcactgttc taatcgtgct     960
tggtgctttg ctggaatcac tcaggagtct tgggaatcct tggaagtttg attcccagta    1020
attatcagca gataatgagt gtgaagctcc ccaataatta agatgagata ttcctcgacg    1080
aacgaagttc agagcttctg caaggatgta ggacat                              1116

<210> SEQ ID NO 42
<211> LENGTH: 1077
<212> TYPE: DNA
```

<213> ORGANISM: Penicillium paxilli

<400> SEQUENCE: 42

```
atgggcgtag cagggagcgg agttctttac tttcttttca acaatgtccc gagtcctcgc      60
ttctggttga agaaaaccca gttgatagga accgagaacc cagaaggcat aactggctac     120
gaatgccctt atgaatatct gcggaagtca tacggcaagc atcactgggc agcgttcgtt     180
gacaagctat cgcccaacct tcaaaatgag gatccagcta ataccgcat ggtgcttgaa      240
acaatggatg tcattcacct atgcttgatg atggtcgacg atgtaagatc atttgccatt    300
atatagaggc tttattatca ttgtatctaa cttctgattc ctagatctcc gatggaagcg    360
aatatcgcaa aggaaagccg gctgcgcaca aaatttatgg tgcgcctgaa acagcgaatc    420
gggcttatta tcgagttaca caaatattgg ctcaaactgc gacagaattc ccacgtcttt    480
cgccttggtt gatgactgat cttcgggata ttctcgaggg tcaagatatg tcccttgtct    540
ggcgccgaga cggagtcaat gggttccctg gaactgcatc ggagagaact gctgcttaca    600
agcgcatggt tctgctaaag acaggtggac tatttcgtct actcgggcat ctcactctcg    660
agaacaattc catggatgaa gcctttagca cccttgggta agaaagaaaa atattttcgg    720
cagccttctg aattttgcta atatttaatg attcctagct ggcattcgca attgcaaaat    780
gactgcaaga atgtctactc gtcggaatat gccaagatga agggcgttgt agcagaagat    840
ttgctcaatc gtgagatgac ataccccatc gtactcgcac tggacgcctc tggtggtcat    900
tgggtagagg cagctctaaa gtcgccctct cggcgaaacg tcggaaatgc cttgaagata    960
atacagtgcg actatgttcg agatgtttgc atggcagagc tggcgagatc tggtgccccg   1020
gttaaggaat ggttgaagtt atggaaacgg gaggagaagc ttgacctgaa ggcatga      1077
```

<210> SEQ ID NO 43
<211> LENGTH: 954
<212> TYPE: DNA
<213> ORGANISM: Penicillium paxilli

<400> SEQUENCE: 43

```
atgggcgtag cagggagcgg agttctttac tttcttttca acaatgtccc gagtcctcgc      60
ttctggttga agaaaaccca gttgatagga accgagaacc cagaaggcat aactggctac     120
gaatgccctt atgaatatct gcggaagtca tacggcaagc atcactgggc agcgttcgtt     180
gacaagctat cgcccaacct tcaaaatgag gatccagcta ataccgcat ggtgcttgaa      240
acaatggatg tcattcacct atgcttgatg atggtcgacg atatctccga tggaagcgaa    300
tatcgcaaag gaaagccggc tgcgcacaaa atttatggtg cgcctgaaac agcgaatcgg    360
gcttattatc gagttacaca aatattggct caaactgcga cagaattccc acgtctttcg    420
ccttggttga tgactgatct tcgggatatt ctcgagggtc aagatatgtc ccttgtctgg    480
cgccgagacg gagtcaatgg gttccctgga actgcatcgg agagaactgc tgcttacaag    540
cgcatggttc tgctaaagac aggtggacta tttcgtctac tcgggcatct cactctcgag    600
aacaattcca tggatgaagc ctttagcacc cttggctggc attcgcaatt gcaaaatgac    660
tgcaagaatg tctactcgtc ggaatatgcc aagatgaagg gcgttgtagc agaagatttg    720
ctcaatcgtg agatgacata ccccatcgta ctcgcactgg acgcctctgg tggtcattgg    780
gtagaggcag ctctaaagtc gccctctcgg cgaaacgtcg gaaatgcctt gaagataata    840
cagtgcgact atgttcgaga tgtttgcatg gcagagctgg cgagatctgg tgccccggtt    900
aaggaatggt tgaagttatg gaaacgggag gaagcttg acctgaaggc atga            954
```

<210> SEQ ID NO 44
<211> LENGTH: 317
<212> TYPE: PRT
<213> ORGANISM: Penicillium paxilli

<400> SEQUENCE: 44

Met Gly Val Ala Gly Ser Gly Val Leu Tyr Phe Leu Phe Asn Asn Val
1               5                   10                  15

Pro Ser Pro Arg Phe Trp Leu Lys Lys Thr Gln Leu Ile Gly Thr Glu
            20                  25                  30

Asn Pro Glu Gly Ile Thr Gly Tyr Glu Cys Pro Tyr Glu Tyr Leu Arg
        35                  40                  45

Lys Ser Tyr Gly Lys His His Trp Ala Ala Phe Val Asp Lys Leu Ser
    50                  55                  60

Pro Asn Leu Gln Asn Glu Asp Pro Ala Lys Tyr Arg Met Val Leu Glu
65                  70                  75                  80

Thr Met Asp Val Ile His Leu Cys Leu Met Met Val Asp Asp Ile Ser
                85                  90                  95

Asp Gly Ser Glu Tyr Arg Lys Gly Lys Pro Ala Ala His Lys Ile Tyr
            100                 105                 110

Gly Ala Pro Glu Thr Ala Asn Arg Ala Tyr Tyr Arg Val Thr Gln Ile
        115                 120                 125

Leu Ala Gln Thr Ala Thr Glu Phe Pro Arg Leu Ser Pro Trp Leu Met
    130                 135                 140

Thr Asp Leu Arg Asp Ile Leu Glu Gly Gln Asp Met Ser Leu Val Trp
145                 150                 155                 160

Arg Arg Asp Gly Val Asn Gly Phe Pro Gly Thr Ala Ser Glu Arg Thr
                165                 170                 175

Ala Ala Tyr Lys Arg Met Val Leu Leu Lys Thr Gly Gly Leu Phe Arg
            180                 185                 190

Leu Leu Gly His Leu Thr Leu Glu Asn Asn Ser Met Asp Glu Ala Phe
        195                 200                 205

Ser Thr Leu Gly Trp His Ser Gln Leu Gln Asn Asp Cys Lys Asn Val
    210                 215                 220

Tyr Ser Ser Glu Tyr Ala Lys Met Lys Gly Val Val Ala Glu Asp Leu
225                 230                 235                 240

Leu Asn Arg Glu Met Thr Tyr Pro Ile Val Leu Ala Leu Asp Ala Ser
                245                 250                 255

Gly Gly His Trp Val Glu Ala Leu Lys Ser Pro Ser Arg Arg Asn
            260                 265                 270

Val Gly Asn Ala Leu Lys Ile Ile Gln Cys Asp Tyr Val Arg Asp Val
        275                 280                 285

Cys Met Ala Glu Leu Ala Arg Ser Gly Ala Pro Val Lys Glu Trp Leu
    290                 295                 300

Lys Leu Trp Lys Arg Glu Glu Lys Leu Asp Leu Lys Ala
305                 310                 315

<210> SEQ ID NO 45
<211> LENGTH: 1559
<212> TYPE: DNA
<213> ORGANISM: Penicillium paxilli

<400> SEQUENCE: 45
ttaaacttga agaaaataaa acttcagggc accctcgagg tcgaacatca ttgtaagaga    60

| | |
|---|---|
| ggtatagaca atggttagtc caaatagata gatcataagt tgagtcaaat aactccagct | 120 |
| tcgcccctgt ttgctatact tctcccatcc accaccactt cgctttggcg tagggaggaa | 180 |
| atcacacatt gtgccatcag caatcgtttt tgacgccata tcagcaggca ggtcaccagc | 240 |
| gtatggtgcc caataccggc ttagcaggct atagattatg ccatcacgaa cctgaaaacg | 300 |
| aaccaagaat cgagagctct ggtagatagt attgacgcgc tcatatcgaa ggtcgcgata | 360 |
| tttttgcaaa aggaactcca tttgtgagga ggtgggaaag tatggtccag aggaaatccg | 420 |
| catctttcga aggagatttg ccagagcagc ggcatcctca atggccatat tagccccttg | 480 |
| accaacattg ggagtcattt tgtggacact gtctcctaag agcacgcagc ggccatggtg | 540 |
| ccagactttg aatgtatttt cttccagagc agtcattgaa gatgtctctc ttttgtccca | 600 |
| gagctcgcca aaagtaatgt tttcgtaaaa cttgacatcc ctgatctctt ctgccgcaat | 660 |
| agatgtttca tgggacgtgt agcgggggct gtcaggatac acgtatttct tgcccagctt | 720 |
| ttgaatgacg aaccaatata tgcgaccgtc ttttccatgg attgtgacaa tagtgagacc | 780 |
| atcgaataaa gcgttgactt gctcgccaag ttttaatccc ggcatcgccg atgaaatgcc | 840 |
| gaaaatacag cgaaactcga ccgtaagctc ttcgtacttg ttagcatgaa tgcaaagaca | 900 |
| tgaggcctgt tgatgctatc cactcactgg aactatcttt tttgatcttt gatacccgtc | 960 |
| tggcaattcc ccttgccttc catatctctc tgcggacgat gctgtggact ccatctgcgc | 1020 |
| cgacaagaag atccccacga taaacgtgtc cagttgtggt ggtaattagc actccatcat | 1080 |
| ccaatgattc aattgatgta actctttggc ccagacgtat tttgctggga tctggatacc | 1140 |
| ctttgtagag aatttcgagc atcttctgtc gatctagaaa cgctatagga aaaccgaacc | 1200 |
| tgttgcctca cgggtgccat tttagatgat aatgcaaaac tgtataagat caagataatt | 1260 |
| actgaccttt gatcgatgat ctttggatat gagctgctga agttgaaccc atcaggaagc | 1320 |
| ccaattgtag ctttgcttag cggttcgata tgctcttcaa cttgatcata gagctgaagc | 1380 |
| tgatccagca cgcgagctcc attcggcaga atgccgatgg atgctccaat ctgtggtgct | 1440 |
| ggatcgctgg cctttccag acaacatgt tttattcccg cacgatgtag acaatgtgcc | 1500 |
| aatgtcaatc ctccgatcga cccgcccaca atgataactt gaaactcggc cttttccat | 1559 |

<210> SEQ ID NO 46
<211> LENGTH: 1434
<212> TYPE: DNA
<213> ORGANISM: Penicillium paxilli

<400> SEQUENCE: 46

| | |
|---|---|
| ttaaacttga agaaaataaa acttcagggc accctcgagg tcgaacatca ttgtaagaga | 60 |
| ggtatagaca atggttagtc caaatagata gatcataagt tgagtcaaat aactccagct | 120 |
| tcgcccctgt ttgctatact tctcccatcc accaccactt cgctttggcg tagggaggaa | 180 |
| atcacacatt gtgccatcag caatcgtttt tgacgccata tcagcaggca ggtcaccagc | 240 |
| gtatggtgcc caataccggc ttagcaggct atagattatg ccatcacgaa cctgaaaacg | 300 |
| aaccaagaat cgagagctct ggtagatagt attgacgcgc tcatatcgaa ggtcgcgata | 360 |
| tttttgcaaa aggaactcca tttgtgagga ggtgggaaag tatggtccag aggaaatccg | 420 |
| catctttcga aggagatttg ccagagcagc ggcatcctca atggccatat tagccccttg | 480 |
| accaacattg ggagtcattt tgtggacact gtctcctaag agcacgcagc ggccatggtg | 540 |
| ccagactttg aatgtatttt cttccagagc agtcattgaa gatgtctctc ttttgtccca | 600 |
| gagctcgcca aaagtaatgt tttcgtaaaa cttgacatcc ctgatctctt ctgccgcaat | 660 |

-continued

```
agatgtttca tgggacgtgt agcgggggct gtcaggatac acgtatttct tgcccagctt    720
ttgaatgacg aaccaatata tgcgaccgtc ttttccatgg attgtgacaa tagtgagacc    780
atcgaataaa gcgttgactt gctcgccaag ttttaatccc ggcatcgccg atgaaatgcc    840
gaaaatacag cgaaactcga ccgtaagctt ggaactatct tgtttgatct ttgatacccg    900
tctggcaatt ccccttgcct tccatatctc tctgcggacg atgctgtgga ctccatctgc    960
gccgacaaga agatccccac gataaacgtg tccagttgtg gtggtaatta gcactccatc    1020
atccaatgat tcaattgatg taactctttg gcccagacgt attttgctgg gatctggata    1080 cccttgtag agaatttcga gcatcttctg tcgatctaga aacgctatag gaaaaccgaa    1140
cctttgatcg atgatctttg gatatgagct gctgaagttg aacccatcag gaagcccaat    1200
tgtagctttg cttagcggtt cgatatgctc ttcaacttga tcatagagct gaagctgatc    1260
cagcacgcga gctccattcg gcagaatgcc gatggatgct ccaatctgtg gtgctggatc    1320
gctggccttt tccaggacaa catgttttat tcccgcacga tgtagacaat gtgccaatgt    1380
caatcctccg atcgacccgc ccacaatgat aacttgaaac tcggccttt ccat    1434
```

<210> SEQ ID NO 47
<211> LENGTH: 477
<212> TYPE: PRT
<213> ORGANISM: Penicillium paxilli

<400> SEQUENCE: 47

```
Met Glu Lys Ala Glu Phe Gln Val Ile Ile Val Gly Gly Ser Ile Gly
1               5                   10                  15

Gly Leu Thr Leu Ala His Cys Leu His Arg Ala Gly Ile Lys His Val
            20                  25                  30

Val Leu Glu Lys Ala Ser Asp Pro Ala Pro Gln Ile Gly Ala Ser Ile
        35                  40                  45

Gly Ile Leu Pro Asn Gly Ala Arg Val Leu Asp Gln Leu Gln Leu Tyr
    50                  55                  60

Asp Gln Val Glu Glu His Ile Glu Pro Leu Ser Lys Ala Thr Ile Gly
65                  70                  75                  80

Leu Pro Asp Gly Phe Asn Phe Ser Ser Ser Tyr Pro Lys Ile Ile Asp
                85                  90                  95

Gln Arg Phe Gly Phe Pro Ile Ala Phe Leu Asp Arg Gln Lys Met Leu
            100                 105                 110

Glu Ile Leu Tyr Lys Gly Tyr Pro Asp Pro Ser Lys Ile Arg Leu Gly
        115                 120                 125

Gln Arg Val Thr Ser Ile Glu Ser Leu Asp Asp Gly Val Leu Ile Thr
    130                 135                 140

Thr Thr Thr Gly His Val Tyr Arg Gly Asp Leu Leu Val Gly Ala Asp
145                 150                 155                 160

Gly Val His Ser Ile Val Arg Arg Glu Ile Trp Lys Ala Arg Gly Ile
                165                 170                 175

Ala Arg Arg Val Ser Lys Ile Lys Gln Asp Ser Ser Lys Leu Thr Val
            180                 185                 190

Glu Phe Arg Cys Ile Phe Gly Ile Ser Ser Ala Met Pro Gly Leu Lys
        195                 200                 205

Leu Gly Glu Gln Val Asn Ala Leu Phe Asp Gly Leu Thr Ile Val Thr
    210                 215                 220

Ile His Gly Lys Asp Gly Arg Ile Tyr Trp Phe Val Ile Gln Lys Leu
225                 230                 235                 240
```

Gly Lys Lys Tyr Val Tyr Pro Asp Ser Pro Arg Tyr Thr Ser His Glu
                245                 250                 255

Thr Ser Ile Ala Ala Glu Ile Arg Asp Val Lys Phe Tyr Glu Asn
        260                 265                 270

Ile Thr Phe Gly Glu Leu Trp Asp Lys Arg Glu Thr Ser Met Thr
    275                 280                 285

Ala Leu Glu Glu Asn Thr Phe Lys Val Trp His His Gly Arg Cys Val
        290                 295                 300

Leu Leu Gly Asp Ser Val His Lys Met Thr Pro Asn Val Gly Gln Gly
305                 310                 315                 320

Ala Asn Met Ala Ile Glu Asp Ala Ala Leu Ala Asn Leu Leu Arg
            325                 330                 335

Lys Met Arg Ile Ser Ser Gly Pro Tyr Phe Pro Thr Ser Ser Gln Met
            340                 345                 350

Glu Phe Leu Leu Gln Lys Tyr Arg Asp Leu Arg Tyr Glu Arg Val Asn
        355                 360                 365

Thr Ile Tyr Gln Ser Ser Arg Phe Leu Val Arg Phe Gln Val Arg Asp
    370                 375                 380

Gly Ile Ile Tyr Ser Leu Leu Ser Arg Tyr Trp Ala Pro Tyr Ala Gly
385                 390                 395                 400

Asp Leu Pro Ala Asp Met Ala Ser Lys Thr Ile Ala Asp Gly Thr Met
            405                 410                 415

Cys Asp Phe Leu Pro Thr Pro Lys Arg Ser Gly Gly Gly Trp Glu Lys
            420                 425                 430

Tyr Ser Lys Gln Gly Arg Ser Trp Ser Tyr Leu Thr Gln Leu Met Ile
        435                 440                 445

Tyr Leu Phe Gly Leu Thr Ile Val Tyr Thr Ser Leu Thr Met Met Phe
    450                 455                 460

Asp Leu Glu Gly Ala Leu Lys Phe Tyr Phe Leu Gln Val
465                 470                 475

<210> SEQ ID NO 48
<211> LENGTH: 1681
<212> TYPE: DNA
<213> ORGANISM: Hypoxylon pulicicidum

<400> SEQUENCE: 48
atggacaagc taccacagga atcgtggac atcatcgtct tctttgccaa ctccaacgag   60
caagggaacc aatatcacat gcacggcccc gatgctaagc atcttgcgag acaattagtc  120 actgttttcca agaaattcca gcgcgccatc gagtgtgata cattcaaggt acttcatctc  180
gacttggacc gggctcgtga tgctcgtgat atcctttccc ggttctctag atggtcgcat  240
ctgagactac tagaatttac tgctatcctg cccgactatg acgaagttgc gtgcactcga  300
tatgagaacg ctgcagagaa agcagagaat tcgcgggtgt ttacggaaaa catcacagag  360
ttgttccacc ttctctctca atgcccagtt gcatgtgctt ctagacctgt ggtattgagg  420
gtagagatat attccaagac ggatcgcatc tgtgtcagcc acagtcttca aggccgtgtg  480
actcaaaagg agacgcacgc caagccagtg tctggtgaca taaggaggtg gaggtggaag  540
cggtcaaaac tacagcttga caagtcagtt cgtcttgcct caatcaaaca cctaaatata  600
cctgtcttcc agatgcaaag gcgcccgtta ttattccgac atgttgctgc tgatagcatt  660
atgcgattaa tatcagcaat gcctcccctcc ctcaagttta ccgtcaaccg gttttcagat  720
accgaaaaga cgatcttgc tcatcgaatt gcacatcgtg agggtaagcg ttagggtctc  780

```
accattgatc gattaatatt cccacccatg cgttctctaa actaacatat ttccagatat    840
cgccaatgca atcgactctc ttcctaagct gatctcccca tactttcatg tggaatactt    900
gccccccctg gatcacaact tccaaccacc cgtactccac aatcacgata cgcagagcga    960
ttcggtctcc tgtgcaatac gcaggatcac ccagagatgc aaaagggtat tcgtcacagg   1020
tgtcctaggc tcaactgagc tgttctggcc aaatgtaaat tcggcccctg acccatactg   1080
gcactcgttg gaatttctgg atatttggta ccatcccatt accccgggtg caagtggct    1140
atttggatta gacccatttc tccatttcgg gtcggcgcga atgcaggctc gcgatctcta   1200
ttcgcgtcct gagccagtag aggggcgtgc ggatgaagat caacaagcat gtcaatttcg   1260
ctatacagca atccagcaac tcatggatga gttctatgta gcggcagcac gagctgcggc   1320
aaatatgcca agttgaaga ggttggcttt ggtggtaacc caccaaccga gttggagaat    1380
tgatggtgct ccctacacc atttcgagtt ccggcgtcc aaagacaatc atgcctcaat     1440
tacttggacc tcctcaccag tatttactcc tagtcaggct gttatcgatg cctggatgcg   1500
tgtatcctgc attcgcggct tgtctatgcg agtaaggcta accggacgtc cattcaacga   1560
cagaggtaat acgcgctatg tggatcccac cgatgatgac cctgatagtg tgcatgaaga   1620
ggaggaggat gacgaggagt atgacgaggg ggatagcgag gaggatgaag gggaggaatg   1680
a                                                                  1681

<210> SEQ ID NO 49
<211> LENGTH: 1608
<212> TYPE: DNA
<213> ORGANISM: Hypoxylon pulicicidum

<400> SEQUENCE: 49
atggacaagc taccacagga atcgtggac atcatcgtct tctttgccaa ctccaacgag       60
caagggaacc aatatcacat gcacggcccc gatgctaagc atcttgcgag acaattagtc     120
actgttccca agaaattcca gcgcgccatc gagtgtgata cattcaaggt acttcatctc     180
gacttggacc gggctcgtga tgctcgtgat atcctttccc ggttctctag atggtcgcat     240
ctgagactac tagaatttac tgctatcctg cccgactatg acgaagttgc gtgcactcga     300
tatgagaacg ctgcagagaa agcagagaat tcgcgggtgt ttacggaaaa catcacagag     360
ttgttccacc ttctctctca atgcccagtt gcatgtgctt ctagacctgt ggtattgagg     420
gtagagatat attccaagac ggatcgcatc tgtgtcagcc acagtcttca aggccgtgtg     480
actcaaaagg agacgcacgc caagccagtg tctggtgaca taaggaggtg gaggtggaag     540
cggtcaaaac tacagcttga caagtcagtt cgtcttgcct caatcaaaca cctaaatata     600
cctgtcttcc agatgcaaag gcgcccgtta ttattccgac atgttgctgc tgatagcatt     660
atgcgattaa tatcagcaat gcctccctcc ctcaagttta ccgtcaaccg gttttcagat     720
accgaaaaga acgatcttgc tcatcgaatt gcacatcgtg aggatatcgc caatgcaatc     780
gactctcttc ctaagctgat ctccccatac tttcatgtgg aatacttgcc cccctggat     840
cacaacttcc aaccacccgt actccacaat cacgatacgc agagcgattc ggtctcctgt     900
gcaatacgca ggatcaccca gagatgcaaa agggtattcg tcacaggtgt cctaggctca    960
actgagctgt tctggccaaa tgtaaattcg gcccctgacc catactggca ctcgttggaa   1020
tttctggata tttggtacca tcccattacc ccgggtggca agtggctatt tggattagac   1080
ccatttctcc atttcgggtc ggcgcgaatg caggctcgcg atctctattc gcgtcctgag   1140
```

-continued

| | | | | |
|---|---|---|---|---|
| ccagtagagg | ggcgtgcgga | tgaagatcaa | caagcatgtc | aatttcgcta tacagcaatc | 1200 |
| cagcaactca | tggatgagtt | ctatgtagcg | gcagcacgag | ctgcggcaaa tatgccaaag | 1260 |
| ttgaagaggt | tggctttggt | ggtaacccac | caaccgagtt | ggagaattga tggtgctccc | 1320 |
| ctacaccatt | tcgagttccg | ggcgtccaaa | gacaatcatg | cctcaattac ttggacctcc | 1380 |
| tcaccagtat | ttactcctag | tcaggctgtt | atcgatgcct | ggatgcgtgt atcctgcatt | 1440 |
| cgcggcttgt | ctatgcgagt | aaggctaacc | ggacgtccat | tcaacgacag aggtaatacg | 1500 |
| cgctatgtgg | atcccaccga | tgatgaccct | gatagtgtgc | atgaagagga ggaggatgac | 1560 |
| gaggagtatg | acgaggggga | tagcgaggag | gatgaagggg | aggaatga | 1608 |

<210> SEQ ID NO 50
<211> LENGTH: 535
<212> TYPE: PRT
<213> ORGANISM: Hypoxylon pulicicidum

<400> SEQUENCE: 50

Met Asp Lys Leu Pro Gln Glu Ile Val Asp Ile Ile Val Phe Phe Ala
1               5                   10                  15

Asn Ser Asn Glu Gln Gly Asn Gln Tyr His Met His Gly Pro Asp Ala
            20                  25                  30

Lys His Leu Ala Arg Gln Leu Val Thr Val Ser Lys Lys Phe Gln Arg
        35                  40                  45

Ala Ile Glu Cys Asp Thr Phe Lys Val Leu His Leu Asp Leu Asp Arg
    50                  55                  60

Ala Arg Asp Ala Arg Asp Ile Leu Ser Arg Phe Ser Arg Trp Ser His
65                  70                  75                  80

Leu Arg Leu Leu Glu Phe Thr Ala Ile Leu Pro Asp Tyr Asp Glu Val
                85                  90                  95

Ala Cys Thr Arg Tyr Glu Asn Ala Ala Glu Lys Ala Glu Asn Ser Arg
            100                 105                 110

Val Phe Thr Glu Asn Ile Thr Glu Leu Phe His Leu Leu Ser Gln Cys
        115                 120                 125

Pro Val Ala Cys Ala Ser Arg Pro Val Val Leu Arg Val Glu Ile Tyr
    130                 135                 140

Ser Lys Thr Asp Arg Ile Cys Val Ser His Ser Leu Gln Gly Arg Val
145                 150                 155                 160

Thr Gln Lys Glu Thr His Ala Lys Pro Val Ser Gly Asp Ile Arg Arg
                165                 170                 175

Trp Arg Trp Lys Arg Ser Lys Leu Gln Leu Asp Lys Ser Val Arg Leu
            180                 185                 190

Ala Ser Ile Lys His Leu Asn Ile Pro Val Phe Gln Met Gln Arg Arg
        195                 200                 205

Pro Leu Leu Phe Arg His Val Ala Ala Asp Ser Ile Met Arg Leu Ile
    210                 215                 220

Ser Ala Met Pro Pro Ser Leu Lys Phe Thr Val Asn Arg Phe Ser Asp
225                 230                 235                 240

Thr Glu Lys Asn Asp Leu Ala His Arg Ile Ala His Arg Glu Asp Ile
                245                 250                 255

Ala Asn Ala Ile Asp Ser Leu Pro Lys Leu Ile Ser Pro Tyr Phe His
            260                 265                 270

Val Glu Tyr Leu Pro Pro Leu Asp His Asn Phe Gln Pro Pro Val Leu
        275                 280                 285

His Asn His Asp Thr Gln Ser Asp Ser Val Ser Cys Ala Ile Arg Arg

```
        290                 295                 300
Ile Thr Gln Arg Cys Lys Arg Val Phe Val Thr Gly Val Leu Gly Ser
305                 310                 315                 320

Thr Glu Leu Phe Trp Pro Asn Val Asn Ser Ala Pro Asp Pro Tyr Trp
                325                 330                 335

His Ser Leu Glu Phe Leu Asp Ile Trp Tyr His Pro Ile Thr Pro Gly
                340                 345                 350

Gly Lys Trp Leu Phe Gly Leu Asp Pro Phe Leu His Phe Gly Ser Ala
            355                 360                 365

Arg Met Gln Ala Arg Asp Leu Tyr Ser Arg Pro Glu Pro Val Glu Gly
        370                 375                 380

Arg Ala Asp Glu Asp Gln Gln Ala Cys Gln Phe Arg Tyr Thr Ala Ile
385                 390                 395                 400

Gln Gln Leu Met Asp Glu Phe Tyr Val Ala Ala Arg Ala Ala Ala
                405                 410                 415

Asn Met Pro Lys Leu Lys Arg Leu Ala Leu Val Val Thr His Gln Pro
                420                 425                 430

Ser Trp Arg Ile Asp Gly Ala Pro Leu His His Phe Glu Phe Arg Ala
            435                 440                 445

Ser Lys Asp Asn His Ala Ser Ile Thr Trp Thr Ser Ser Pro Val Phe
        450                 455                 460

Thr Pro Ser Gln Ala Val Ile Asp Ala Trp Met Arg Val Ser Cys Ile
465                 470                 475                 480

Arg Gly Leu Ser Met Arg Val Arg Leu Thr Gly Arg Pro Phe Asn Asp
                485                 490                 495

Arg Gly Asn Thr Arg Tyr Val Asp Pro Thr Asp Asp Pro Asp Ser
                500                 505                 510

Val His Glu Glu Glu Asp Asp Glu Glu Tyr Asp Gly Asp Ser
            515                 520                 525

Glu Glu Asp Glu Gly Glu Glu
    530                 535

<210> SEQ ID NO 51
<211> LENGTH: 819
<212> TYPE: DNA
<213> ORGANISM: Penicillium paxilli

<400> SEQUENCE: 51
tcaatttgct tttttcggcc cgcttatgcc aagtgacttt tcgttacggt cgacgtacca    60
gaaacaaatt ccataaaacc catcgattga taaaaacacc acaagactcc acagtaccaa   120
aggactattc agccaaccga atgcttccga ccaatacatc caacgtaagc cggcaaaccc   180
aactgtacat gttgatccta agaagcggga agccctatag tacagaagat gagtacttgt   240
atttctgtca ctttggggaa gaaattccga ttcatcgggc atgaaatgag atcagacata   300
ccatagagta taggatgcgc cacgcgtact gcctcgacac aacagttgac tcaatccacc   360
aacgcttaga agaagttgac aaatgacggc ccccatgaa tatgccagcg caggcccgat   420
ttcaagggcc aatgcaacat gcccagagag aaagcccatg gtcgcgacga aaaatatcaa   480
ggaaatattg cgctcaacaa gcggcgcatg cccccactct cgggatgaaa acgttattgc   540
tgcgtacatg acaccaaagt tgatgaggag gcccatccag aatacacccc tctccaccgg   600
gcttttcgag ggaaagacca gacagtagac cagttcccac gcgatgttgc aacagagggg   660
cataatcgac attccgtaag tttcatgttt gaacgagatg tagaccattc cgatgtagtt   720
```

```
tatgatccat cctactccca tgccaacaac aaaaagatca gccaatggct taatcgcctg      780
gtactccgga ggagcttggg aaacatcaaa accgtccat                            819
```

<210> SEQ ID NO 52
<211> LENGTH: 732
<212> TYPE: DNA
<213> ORGANISM: Penicillium paxilli

<400> SEQUENCE: 52

```
tcaatttgct tttttcggcc cgcttatgcc aagtgacttt tcgttacggt cgacgtacca      60
gaaacaaatt ccataaaacc catcgattga taaaaacacc acaagactcc acagtaccaa     120
aggactattc agccaaccga atgcttccga ccaatacatc caacgtaagc cggcaaaccc     180
aactgtacat gttgatccta agaagcggga agcccataga gtataggatg cgccacgcgt     240
actgcctcga cacaacagtt gactcaatcc accaacgctt agaagaagtt gacaaatgac     300 ggcccccat gaatatgcca gcgcaggccc gatttcaagg ccaatgcaa catgcccaga      360 gagaaagccc atggtcgcga cgaaaaatat caaggaaata ttgcgctcaa caagcggcgc     420
atggccccac tctcgggatg aaaacgttat tgctgcgtac atgacaccaa agttgatgag     480
gaggcccatc cagaatacac ccctctccac cgggcttttc gagggaaaga ccagacagta     540
gaccagttcc cacgcgatgt tgcaacagag gggcataatc gacattccgt aagtttcatg     600
tttgaacgag atgtagacca ttccgatgta gtttatgatc catcctactc ccatgccaac     660
aacaaaaaga tcagccaatg gcttaatcgc ctggtactcc ggaggagctt gggaaacatc     720
aaaaccgtcc at                                                         732
```

<210> SEQ ID NO 53
<211> LENGTH: 243
<212> TYPE: PRT
<213> ORGANISM: Penicillium paxilli

<400> SEQUENCE: 53

```
Met Asp Gly Phe Asp Val Ser Gln Ala Pro Glu Tyr Gln Ala Ile
1               5                  10                  15

Lys Pro Leu Ala Asp Leu Phe Val Val Gly Met Gly Val Gly Trp Ile
            20                  25                  30

Ile Asn Tyr Ile Gly Met Val Tyr Ile Ser Phe Lys His Glu Thr Tyr
        35                  40                  45

Gly Met Ser Ile Met Pro Leu Cys Cys Asn Ile Ala Trp Glu Leu Val
    50                  55                  60

Tyr Cys Leu Val Phe Pro Ser Lys Ser Pro Val Glu Arg Gly Val Phe
65                  70                  75                  80

Trp Met Gly Leu Leu Ile Asn Phe Gly Val Met Tyr Ala Ala Ile Thr
                85                  90                  95

Phe Ser Ser Arg Glu Trp Gly His Ala Pro Leu Val Glu Arg Asn Ile
            100                 105                 110

Ser Leu Ile Phe Phe Val Ala Thr Met Gly Phe Leu Ser Gly His Val
        115                 120                 125

Ala Leu Ala Leu Glu Ile Gly Pro Ala Leu Ala Tyr Ser Trp Gly Ala
    130                 135                 140

Val Ile Cys Gln Leu Leu Leu Ser Val Gly Gly Leu Ser Gln Leu Leu
145                 150                 155                 160

Cys Arg Gly Ser Thr Arg Gly Ala Ser Tyr Thr Leu Trp Ala Ser Arg
                165                 170                 175
```

```
Phe Leu Gly Ser Thr Cys Thr Val Gly Phe Ala Gly Leu Arg Trp Met
            180                 185                 190

Tyr Trp Ser Glu Ala Phe Gly Trp Leu Asn Ser Pro Leu Val Leu Trp
        195                 200                 205

Ser Leu Val Val Phe Leu Ser Ile Asp Gly Tyr Gly Ile Cys Phe
    210                 215                 220

Trp Tyr Val Asp Arg Asn Glu Lys Ser Leu Gly Ile Ser Gly Pro Lys
225                 230                 235                 240

Lys Ala Asn

<210> SEQ ID NO 54
<211> LENGTH: 5083
<212> TYPE: DNA
<213> ORGANISM: Hypoxylon pulicicidum

<400> SEQUENCE: 54
```

| | |
|---|---|
| atgggatatg gaccaggtac aagagcctct gcaggcgttt ctgattccgc attgaggggc | 60 |
| atgcaagaac tgacagcatt tttttcacca gagcttcata agacattaac tcgcgtacta | 120 |
| tctagctcta gatctgatgg cacgtcatta tttcacggtc gttcattgat ctctgaatcg | 180 |
| actcccgtaa cctccgataa tgagactcac ggcgttcttg cctatcaac tctttacgaa | 240 |
| ccctcatttc ctactagcgc tacggccgat atcgtcttcg tccatggatt aggcggaggt | 300 |
| agtcgaaaaa catggtccta ttcccccgac cggtaccact actggcctca gcatggcttt | 360 |
| gcgaacgact cggacttcgc agatatgcgc atccactcct tcggctataa gtccgactgg | 420 |
| gctgagcgac agcaaagcat cctcaatatt cgcgacttcg ccgaatcgtt agtcggagag | 480 |
| ctgaagaaca atcccggcat acgacgtagt aatacacgca tcatattcgt ttgccatagt | 540 |
| atgggcggat gcgtcgccaa aaaggcctac attatatcac gccaggatcc gacctgcaag | 600 |
| gacttagctg acagagtcca ctcgatattc tttctaggca ctccacacag gggcagtgat | 660 |
| cttgcagtga tcctgaagag gttgtctgtc atcgcttggg gctccaagcc gttcgtctcc | 720 |
| gacctcctgc ccgaatcgtc tacattgaga gatatcaacg acacatttcg tcactatgcg | 780 |
| tcggatctgc gcctctggtc cttttacgag acgattcccg ccaagcccag gattttgaac | 840 |
| aaaatcgtgg ttgagaggca ctcggcaacg cttggttacc aaacgaaga gattgttgct | 900 |
| atgaacgctg accaccgcca gttgtgcaaa ttcaaaagtc cggctgaccc taattacaag | 960 |
| atattacgaa atgccctcca cacggctgcc gatatgctaa ggtcattacc acctttggcc | 1020 |
| ttagccccct tagaacctcg tatcaacttg gcttccacac aacagcattc gaaccaagag | 1080 |
| aacgcaagcc aacgcttgag gtcctttcta ggcgtcgttg atacgccaga ggatgaactc | 1140 |
| catattcttc aactgtttca ggagccggga tcttgccggt ggttctcgga atcgaaagac | 1200 |
| ttcgtgtctt gggaatcgga agggtccccg agcatactgt ggctcacggg agaccagcg | 1260 |
| tccggtaaat ccgtccttc tagccacgtc atagagcaag tgaagtctct aggtgccttt | 1320 |
| tgcagttact ttttcttcaa gcaaagggag gctagcaagt ctacgctgag cgattgtttc | 1380 |
| cgctccattg cctttcagat ggccatacaa gatagtgaag tgatgaataa gctacttcaa | 1440 |
| ctcgaaggcg aatggatgac ctgggatatg agcgacgagc tgagcgtctg gagaaggctt | 1500 |
| ttcgtcaatg ggatcttcaa gctgccatcc atctcacagc acttctggat aatcgacggt | 1560 |
| gtcgatgaat gttctaattt caactcccct tttactaaga gaatcctcgc tacgcttcct | 1620 |
| agaggtattc gccttttcgc cagcagccgc catctagaaa aaatccggcg cggtttggca | 1680 |
| cctcttgagt cgcgtgtgaa cctgcagtcc gtgtctgaaa ccgacactct tggtgatatg | 1740 |

```
cggattttcg tgacttcgaa gctcagaggg ctagatcgcc ttgaaaatga tgacagtatc    1800
aatacaatgt gcgagaaaat ccttgggaag gcatccggtt ctttcttatg ggtccgactc    1860
gtacttcaag agttcgaaaa tgcttggact agcgaagcca tggatgctgt cttggatgaa    1920
atacctgtag atcttcaaga catgtatcgc cggatgcttc tgttaatgga aaggatacg    1980 cgtacaatca agctcgccaa atccatcctg acgtgggccg ttctggcatg ccgaccgctc    2040
accgttgacg agctacgtct tgctgtgaag ctcgacgtta atgagacgct gcagagtgta    2100
agcaaggcga ttcctagttt atgccaccaa ctagtctttg tcgacagcgc taatagggtg    2160
cacatcttac atgcaaccgc ccgggaattt cttctcgacg aaactcttca gtcagagttt    2220
gctcttcatg gtgttgagaa gcacgcctct cttggctctc tactgcttcg gtatctcacc    2280
aacaccgcct ttaagttccg tgcgccaccg cggcggcagg gctcaggatt cgcggtttt     2340 gcgaagcccg ttcatagtgt ttctcctgat ctatccctat ggactacgc agcttgcttc     2400 ttctctgagc acatataccg aggcgcctcg agagatgata ccttgatggc cgaactgtgt    2460
gccttcctaa agggcagaac tatcctctca tggattgaac acatcgctag aaatggagat    2520
cttggaggta ttaccaggac ggcgacagac ttacgtggat atctcggccg gaaactggaa    2580
catcttcctc ccacagatcc ctcggcctac cttgttgact gctgggtggc tgatctaatc    2640
cgggttgctg ccaagtttcg atttcagttg ctgacctgtc catcgtctat tcattacatt    2700
atcccatcat tctgtccatc agacactatt atctcgagga cctttgccaa tggtactcga    2760
ccttcgacaa taacagtcaa gggtatccct caagccacgt gggacgactg cttaacccgt    2820
atcgattttg agcgaggtcg agctaccgcc ttgagctatg gtacccaatt cttcgctgtt    2880
ggtttgtcga ccgggcagat ttcgctcttc gatccgcact ctgtccagcc cgtggcgaac    2940
cttgtccatc ctgaaagggt caagatgctg gagtttagct ccgacggaga atatcttgcc    3000
tcctctggca ctagaacttt gcttgtttgg cagccgaaat gtgggatgca gaagttgtca    3060
ttcccattgc agtcggagct tatcgctttt gttttcttaa gcggtgacga atttctttgt    3120
gctttcgcat ctggtgagct aactaaatgg taagatcacc tattcagacc tcacgaatca    3180
caacgccgcc tttcaaagct tcgtctttag atacagtact gattcttgac aacttaggcg    3240
tcttgacacg ggcgaacatg aaacaatctc ctggagaagc atgtgtgata cggatattac    3300
cggtactctg gatattcctg agcagccgcc aagctgcgcg gcgttctcta caggggggtga    3360 gactgtgctg cttgctgtgg gttaccgaaa atacccccata ttcatctggg acgcattgga    3420
gctacaattg ctgggacaat gcggagctga cgaaaacaat gggatagatg acatgacatt    3480
taatccaaac cctgagatat ctgcgctagt ggtctcctac aatgacggca ggttatgcct    3540
cttcgattac acgaccatga tgccgacgtt tactcgacaa agcgtattcg cgaacagtat    3600
tgcctgttcc ccggacggtc gaagtctcgt taccggcagt gtcagggggta tcattgaggt    3660 attcaaattc gaccaggacc ataccgggaa cacggtgcta gtccctatat acaatatcca    3720
agctttagat gactcgatcc gcagcgtagc ctttagcgct gatggcctgc gcttcgttga    3780
ccttcacgac caacaatgcc gcatttgggc acccgtgtct ctgatgcgga aggataacga    3840
actggagagc gtaagtggca ttgcgccgct tcctgccaaa atagtcacca tggccgacga    3900
ctccaatatc acagaaatca cgagtgcctt agctgtgtcc tctaacggcg ccgcgtcat    3960 tgcaggtaag agtaacggcg aggtctccg gttttcggct gtcgatggga aagaattagg    4020
agtgctctat tcgcatggac gttgcgtatc cgttgtcaac gtcaccctag gagaagctcg    4080
```

```
taatttagtc atctcagcgg atgatgctgg cagggtgcta gtggtggaac tgacaacgtg    4140
cctgccagcc tcctcggccg cacagaagct gccagcggct catgttattc tagagcgccg    4200
attcggtgct gctgttgttg gtctactcgt taaccccctcg gtggaccgcc ttctaattag    4260
tgggcgacat gtggatgaac tctgtgatct gccgtcgggc cgggttttgg gttcgatatc    4320
tcatgtcgtc ggtaccgcta catcgacaag agccgtagcc ttccagcatc cagccaacga    4380
ggcctggatc gtcttgatgc tcactaatac cgctcgggtt ttccgctggt ccgatttcca    4440
ggagttgact accgtgaacg gcatcctcct tcggaaacct tcgacagccg tagaggctcc    4500 tctcccacg cattcccggg ctttgaaaac accaaccacg ctcagctcat cgtatcattt    4560
taggcaagat tttgtcctcg agttgctcag aatatcgccc tccgtagctc cacgactcta    4620
cgtttggccg gtgtcagcat ttgatccggc aacagcacag ccggatcacc gagcgcaggt    4680
tcctagggaa gtgaatcttg acgccatcaa tgccggaatc ttggctgtgc ttggaatcgt    4740
aggtcagtct acggttctcc ttatggacgc caatctttgg gtatacagca tggagctccg    4800
cccaacgcaa gccacaccac aggcccaccc tggctttccc cctgaaacga cgatagttca    4860
ggacggacct gagccaatca cgcaacaaat tctgccggtg tttacaagga gacactttt    4920 cgccctgagc gagtggcgca cagccggcga agagttgagg tgcgcggtag cgcagcattc    4980
tggtggcccg agtttcattt ttgccagtag gcagtacatc gtcgtcgttc aaggcggttt    5040
ggagttttcc gaggacatgg ctgtcggcca gcagagtgcg tag                      5083

<210> SEQ ID NO 55
<211> LENGTH: 4995
<212> TYPE: DNA
<213> ORGANISM: Hypoxylon pulicicidum
<400> SEQUENCE: 55
atgggatatg gaccaggtac aagagcctct gcaggcgttt ctgattccgc attgaggggc     60
atgcaagaac tgacagcatt tttttcacca gagcttcata agacattaac tcgcgtacta    120
tctagctcta gatctgatgg cacgtcatta tttcacggtc gttcattgat ctctgaatcg    180
actcccgtaa cctccgataa tgagactcac ggcgttcttg gcctatcaac tctttacgaa    240
ccctcatttc ctactagcgc tacggccgat atcgtcttcg tccatggatt aggcggaggt    300
agtcgaaaaa catggtccta ttcccccgac cggtaccact actggcctca agcatggctt    360
gcgaacgact cggacttcgc agatatgcgc atccactcct tcggctataa gtccgactgg    420
gctgagcgac agcaaagcat cctcaatatt cgcgacttcg ccgaatcgtt agtcggagag    480
ctgaagaaca atcccggcat acgacgtagt aatacacgca tcatattcgt ttgccatagt    540
atgggcggat gcgtcgccaa aaaggcctac attatatcac gccaggatcc gacctgcaag    600
gacttagctg acagagtcca ctcgatattc tttctaggca ctccacacag gggcagtgat    660
cttgcagtga tcctgaagag gttgtctgtc atcgcttggg gctccaagcc gttcgtctcc    720
gacctcctgc ccgaatcgtc tacattgaga gatatcaacg acacatttcg tcactatgcg    780
tcggatctgc gcctctggtc cttttacgag acgattcccg ccaagcccag gattttgaac    840
aaaatcgtgg ttgagaggca ctcggcaacg cttggttacc caaacgaaga gattgttgct    900
atgaacgctg accaccgcca gttgtgcaaa ttcaaaagtc cggctgaccc taattacaag    960
atattacgaa atgccctcca cacggctgcc gatatgctaa ggtcattacc accttttggcc   1020 ttagccccct tagaacctcg tatcaacttg gcttccacac aacagcattc gaaccaagag   1080
aacgcaagcc aacgcttgag gtcctttcta ggcgtcgttg atacgccaga ggatgaactc   1140
```

```
catattcttc aactgtttca ggagccggga tcttgccggt ggttctcgga atcgaaagac    1200
ttcgtgtctt gggaatcgga agggtccccg agcatactgt ggctcacggg agaccagcg    1260 tccggtaaat ccgtcctttc tagccacgtc atagagcaag tgaagtctct aggtgccttt    1320
tgcagttact ttttcttcaa gcaaagggag gctagcaagt ctacgctgag cgattgtttc    1380
cgctccattg cctttcagat ggccatacaa gatagtgaag tgatgaataa gctacttcaa    1440
ctcgaaggcg aatggatgac ctgggatatg agcgacgagc tgagcgtctg gagaaggctt    1500
ttcgtcaatg ggatcttcaa gctgccatcc atctcacagc acttctggat aatcgacggt    1560
gtcgatgaat gttctaattt caactccctt tttactaaga gaatcctcgc tacgcttcct    1620
agaggtattc gccttttcgc cagcagccgc catctagaag aaatccggcg cggtttggca    1680
cctcttgagt cgcgtgtgaa cctgcagtcc gtgtctgaaa ccgacactct tggtgatatg    1740
cggattttcg tgacttcgaa gctcagaggg ctagatcgcc ttgaaaatga tgacagtatc    1800
aatacaatgt gcgagaaaat ccttgggaag gcatccggtt cttccttatg ggtccgactc    1860
gtacttcaag agttcgaaaa tgcttggact agcgaagcca tggatgctgt cttggatgaa    1920
atacctgtag atcttcaaga catgtatcgc cggatgcttc tgttaatgga aaggatacg     1980 cgtacaatca agctcgccaa atccatcctg acgtgggccg ttctggcatg ccgaccgctc    2040
accgttgacg agctacgtct tgctgtgaag ctcgacgtta atgagacgct gcagagtgta    2100
agcaaggcga ttcctagttt atgccaccaa ctagtctttg tcgacagcgc taatagggtg    2160
cacatcttac atgcaaccgc ccgggaattt cttctcgacg aaactcttca gtcagagttt    2220
gctcttcatg gtgttgagaa gcacgcctct cttggctctc tactgcttcg gtatctcacc    2280
aacaccgcct ttaagttccg tgcgccaccg cggcggcagg gctcaggatt tcgcggtttt    2340
gcgaagcccg ttcatagtgt ttctcctgat ctatccctat tggactacgc agcttgcttc    2400
ttctctgagc acatataccg aggcgcctcg agagatgata ccttgatggc cgaactgtgt    2460
gccttcctaa agggcagaac tatcctctca tggattgaac acatcgctag aaatggagat    2520
cttggaggta ttaccaggac ggcgacagac ttacgtggat atctcggccg gaaactggaa    2580
catcttcctc ccacagatcc ctcggcctac cttgttgact gctgggtggc tgatctaatc    2640
cgggttgctg ccaagtttcg atttcagttg ctgacctgtc catcgtctat tcattacatt    2700
atcccatcat tctgtccatc agacactatt atctcgagga ccttgccaa tggtactcga     2760 ccttcgacaa taacagtcaa gggtatccct caagccacgt gggacgactg cttaacccgt    2820
atcgattttg agcgaggtcg agctaccgcc ttgagctatg gtacccaatt cttcgctgtt    2880
ggtttgtcga ccgggcagat ttcgctcttc gatccgcact ctgtccagcc cgtggcgaac    2940
cttgtccatc ctgaaagggt caagatgctg gagtttagct ccgacggaga atatcttgcc    3000
tcctctggca ctagaacttt gcttgtttgg cagccgaaat gtgggatgca gaagttgtca    3060
ttcccattgc agtcggagct tatcgctttt gttttcttaa gcggtgacga atttctttgt    3120
gctttcgcat ctggtgagct aactaaatgg cgtcttgaca cgggcgaaca tgaaacaatc    3180
tcctggagaa gcatgtgtga tacgatatt accggtactc tggatattcc tgagcagccg    3240
ccaagctgcg cggcgttctc tacagggggt gagactgtgc tgcttgctgt gggttaccga    3300
aaatacccca tattcatctg ggacgcattg gagctacaat tgctgggaca atgcggagct    3360
gacgaaaaca atgggataga tgacatgaca tttaatccaa accctgagat atctgcgcta    3420
gtggtctcct acaatgacgg caggttatgc ctcttcgatt acacgaccat gatgccgacg    3480
```

-continued

```
tttactcgac aaagcgtatt cgcgaacagt attgcctgtt ccccggacgg tcgaagtctc    3540
gttaccggca gtgtcagggg tatcattgag gtattcaaat tcgaccagga ccataccggg    3600
aacacggtgc tagtccctat atacaatatc caagctttag atgactcgat ccgcagcgta    3660
gcctttagcg ctgatggcct gcgcttcgtt gaccttcacg accaacaatg ccgcatttgg    3720
gcacccgtgt ctctgatgcg gaaggataac gaactggaga gcgtaagtgg cattgcgccg    3780
cttcctgcca aaatagtcac catggccgac gactccaata tcacagaaat cacgagtgcc    3840
ttagctgtgt cctctaacgg cggccgcgtc attgcaggta agagtaacgg cgaggtctcc    3900
gcgttttcgg ctgtcgatgg gaaagaatta ggagtgctct attcgcatgg acgttgcgta    3960
tccgttgtca acgtcaccct aggagaagct cgtaatttag tcatctcagc ggatgatgct    4020
ggcagggtgc tagtggtgga actgacaacg tgcctgccag cctcctcggc cgcacagaag    4080
ctgccagcgg ctcatgttat tctagagcgc cgattcggtg ctgctgttgt tggtctactc    4140
gttaacccct cggtgaccg ccttctaatt agtgggcgac atgtggatga actctgtgat    4200
ctgccgtcgg gccgggtttt gggttcgata tctcatgtcg tcggtaccgc tacatcgaca    4260
agagccgtag ccttccagca tccagccaac gaggcctgga tcgtcttgat gctcactaat    4320
accgctcggg ttttccgctg gtccgatttc caggagttga ctaccgtgaa cggcatcctc    4380
cttcggaaac cttcgacagc cgtagaggct cctctcccca cgcattcccg ggctttgaaa    4440
acaccaacca cgctcagctc atcgtatcat tttaggcaag attttgtcct cgagttgctc    4500
agaatatcgc cctccgtagc tccacgactc tacgtttggc cggtgtcagc atttgatccg    4560
gcaacagcac agccggatca ccgagcgcag gttcctaggg aagtgaatct tgacgccatc    4620
aatgccggaa tcttggctgt gcttggaatc gtaggtcagt ctacggttct ccttatggac    4680
gccaatcttt gggtatacag catggagctc cgcccaacgc aagccacacc acaggcccac    4740
cctggctttc cccctgaaac gacgatagtt caggacggac ctgagccaat cacgcaacaa    4800
attctgccgg tgtttacaag gagacacttt ttcgccctga gcgagtggcg cacagccggc    4860
gaagagttga ggtgcgcggt agcgcagcat tctggtggcc cgagtttcat ttttgccagt    4920
aggcagtaca tcgtcgtcgt tcaaggcggt ttggagtttt ccgaggacat ggctgtcggc    4980
cagcagagtg cgtag                                                    4995
```

<210> SEQ ID NO 56
<211> LENGTH: 1664
<212> TYPE: PRT
<213> ORGANISM: Hypoxylon pulicicidum

<400> SEQUENCE: 56

```
Met Gly Tyr Gly Pro Gly Thr Arg Ala Ser Ala Gly Val Ser Asp Ser
1               5                   10                  15

Ala Leu Arg Gly Met Gln Glu Leu Thr Ala Phe Phe Ser Pro Glu Leu
            20                  25                  30

His Lys Thr Leu Thr Arg Val Leu Ser Ser Arg Ser Asp Gly Thr
        35                  40                  45

Ser Leu Phe His Gly Arg Ser Leu Ile Ser Glu Ser Thr Pro Val Thr
    50                  55                  60

Ser Asp Asn Glu Thr His Gly Val Leu Gly Leu Ser Thr Leu Tyr Glu
65                  70                  75                  80

Pro Ser Phe Pro Thr Ser Ala Thr Ala Asp Ile Val Phe Val His Gly
                85                  90                  95

Leu Gly Gly Gly Ser Arg Lys Thr Trp Ser Tyr Ser Pro Asp Arg Tyr
```

```
            100                 105                 110
His Tyr Trp Pro Gln Ala Trp Leu Ala Asn Asp Ser Asp Phe Ala Asp
            115                 120                 125

Met Arg Ile His Ser Phe Gly Tyr Lys Ser Asp Trp Ala Glu Arg Gln
            130                 135             140

Gln Ser Ile Leu Asn Ile Arg Asp Phe Ala Glu Ser Leu Val Gly Glu
145                 150                 155                 160

Leu Lys Asn Asn Pro Gly Ile Arg Arg Ser Asn Thr Arg Ile Ile Phe
                165                 170                 175

Val Cys His Ser Met Gly Gly Cys Val Ala Lys Lys Ala Tyr Ile Ile
                180                 185                 190

Ser Arg Gln Asp Pro Thr Cys Lys Asp Leu Ala Asp Arg Val His Ser
            195                 200                 205

Ile Phe Phe Leu Gly Thr Pro His Arg Gly Ser Asp Leu Ala Val Ile
        210                 215                 220

Leu Lys Arg Leu Ser Val Ile Ala Trp Gly Ser Lys Pro Phe Val Ser
225                 230                 235                 240

Asp Leu Leu Pro Glu Ser Ser Thr Leu Arg Asp Ile Asn Asp Thr Phe
                245                 250                 255

Arg His Tyr Ala Ser Asp Leu Arg Leu Trp Ser Phe Tyr Glu Thr Ile
            260                 265                 270

Pro Ala Lys Pro Arg Ile Leu Asn Lys Ile Val Val Glu Arg His Ser
            275                 280                 285

Ala Thr Leu Gly Tyr Pro Asn Glu Glu Ile Val Ala Met Asn Ala Asp
        290                 295                 300

His Arg Gln Leu Cys Lys Phe Lys Ser Pro Ala Asp Pro Asn Tyr Lys
305                 310                 315                 320

Ile Leu Arg Asn Ala Leu His Thr Ala Ala Asp Met Leu Arg Ser Leu
                325                 330                 335

Pro Pro Leu Ala Leu Ala Pro Leu Glu Pro Arg Ile Asn Leu Ala Ser
            340                 345                 350

Thr Gln Gln His Ser Asn Gln Glu Asn Ala Ser Gln Arg Leu Arg Ser
            355                 360                 365

Phe Leu Gly Val Val Asp Thr Pro Glu Asp Glu Leu His Ile Leu Gln
        370                 375                 380

Leu Phe Gln Glu Pro Gly Ser Cys Arg Trp Phe Ser Glu Ser Lys Asp
385                 390                 395                 400

Phe Val Ser Trp Glu Ser Glu Gly Ser Pro Ser Ile Leu Trp Leu Thr
                405                 410                 415

Gly Arg Pro Ala Ser Gly Lys Ser Val Leu Ser Ser His Val Ile Glu
            420                 425                 430

Gln Val Lys Ser Leu Gly Ala Phe Cys Ser Tyr Phe Phe Lys Gln
            435                 440                 445

Arg Glu Ala Ser Lys Ser Thr Leu Ser Asp Cys Phe Arg Ser Ile Ala
450                 455                 460

Phe Gln Met Ala Ile Gln Asp Ser Glu Val Met Asn Lys Leu Leu Gln
465                 470                 475                 480

Leu Glu Gly Glu Trp Met Thr Trp Asp Met Ser Asp Glu Leu Ser Val
                485                 490                 495

Trp Arg Arg Leu Phe Val Asn Gly Ile Phe Lys Leu Pro Ser Ile Ser
            500                 505                 510

Gln His Phe Trp Ile Ile Asp Gly Val Asp Glu Cys Ser Asn Phe Asn
        515                 520                 525
```

```
Ser Leu Phe Thr Lys Arg Ile Leu Ala Thr Leu Pro Arg Gly Ile Arg
    530                 535                 540

Leu Phe Ala Ser Ser Arg His Leu Glu Glu Ile Arg Arg Gly Leu Ala
545                 550                 555                 560

Pro Leu Glu Ser Arg Val Asn Leu Gln Ser Val Ser Glu Thr Asp Thr
                565                 570                 575

Leu Gly Asp Met Arg Ile Phe Val Thr Ser Lys Leu Arg Gly Leu Asp
            580                 585                 590

Arg Leu Glu Asn Asp Asp Ser Ile Asn Thr Met Cys Glu Lys Ile Leu
        595                 600                 605

Gly Lys Ala Ser Gly Ser Phe Leu Trp Val Arg Leu Val Leu Gln Glu
    610                 615                 620

Phe Glu Asn Ala Trp Thr Ser Glu Ala Met Asp Ala Val Leu Asp Glu
625                 630                 635                 640

Ile Pro Val Asp Leu Gln Asp Met Tyr Arg Arg Met Leu Leu Leu Met
                645                 650                 655

Glu Lys Asp Thr Arg Thr Ile Lys Leu Ala Lys Ser Ile Leu Thr Trp
            660                 665                 670

Ala Val Leu Ala Cys Arg Pro Leu Thr Val Asp Glu Leu Arg Leu Ala
        675                 680                 685

Val Lys Leu Asp Val Asn Glu Thr Leu Gln Ser Val Ser Lys Ala Ile
    690                 695                 700

Pro Ser Leu Cys His Gln Leu Val Phe Val Asp Ser Ala Asn Arg Val
705                 710                 715                 720

His Ile Leu His Ala Thr Ala Arg Glu Phe Leu Leu Asp Glu Thr Leu
                725                 730                 735

Gln Ser Glu Phe Ala Leu His Gly Val Glu Lys His Ala Ser Leu Gly
            740                 745                 750

Ser Leu Leu Leu Arg Tyr Leu Thr Asn Thr Ala Phe Lys Phe Arg Ala
        755                 760                 765

Pro Pro Arg Arg Gln Gly Ser Gly Phe Arg Gly Phe Ala Lys Pro Val
    770                 775                 780

His Ser Val Ser Pro Asp Leu Ser Leu Leu Asp Tyr Ala Ala Cys Phe
785                 790                 795                 800

Phe Ser Glu His Ile Tyr Arg Gly Ala Ser Arg Asp Asp Thr Leu Met
                805                 810                 815

Ala Glu Leu Cys Ala Phe Leu Lys Gly Arg Thr Ile Leu Ser Trp Ile
            820                 825                 830

Glu His Ile Ala Arg Asn Gly Asp Leu Gly Gly Ile Thr Arg Thr Ala
        835                 840                 845

Thr Asp Leu Arg Gly Tyr Leu Gly Arg Lys Leu Glu His Leu Pro Pro
    850                 855                 860

Thr Asp Pro Ser Ala Tyr Leu Val Asp Cys Trp Val Ala Asp Leu Ile
865                 870                 875                 880

Arg Val Ala Ala Lys Phe Arg Phe Gln Leu Leu Thr Cys Pro Ser Ser
                885                 890                 895

Ile His Tyr Ile Ile Pro Ser Phe Cys Pro Ser Asp Thr Ile Ile Ser
            900                 905                 910

Arg Thr Phe Ala Asn Gly Thr Arg Pro Ser Thr Ile Thr Val Lys Gly
        915                 920                 925

Ile Pro Gln Ala Thr Trp Asp Asp Cys Leu Thr Arg Ile Asp Phe Glu
    930                 935                 940
```

```
Arg Gly Arg Ala Thr Ala Leu Ser Tyr Gly Thr Gln Phe Phe Ala Val
945                 950                 955                 960

Gly Leu Ser Thr Gly Gln Ile Ser Leu Phe Asp Pro His Ser Val Gln
            965                 970                 975

Pro Val Ala Asn Leu Val His Pro Glu Arg Val Lys Met Leu Glu Phe
            980                 985                 990

Ser Ser Asp Gly Glu Tyr Leu Ala Ser Ser Gly Thr Arg Thr Leu Leu
        995                 1000                1005

Val Trp Gln Pro Lys Cys Gly Met Gln Lys Leu Ser Phe Pro Leu
    1010                1015                1020

Gln Ser Glu Leu Ile Ala Phe Val Phe Leu Ser Gly Asp Glu Phe
    1025                1030                1035

Leu Cys Ala Phe Ala Ser Gly Glu Leu Thr Lys Trp Arg Leu Asp
    1040                1045                1050

Thr Gly Glu His Glu Thr Ile Ser Trp Arg Ser Met Cys Asp Thr
    1055                1060                1065

Asp Ile Thr Gly Thr Leu Asp Ile Pro Glu Gln Pro Pro Ser Cys
    1070                1075                1080

Ala Ala Phe Ser Thr Gly Gly Glu Thr Val Leu Leu Ala Val Gly
    1085                1090                1095

Tyr Arg Lys Tyr Pro Ile Phe Ile Trp Asp Ala Leu Glu Leu Gln
    1100                1105                1110

Leu Leu Gly Gln Cys Gly Ala Asp Glu Asn Asn Gly Ile Asp Asp
    1115                1120                1125

Met Thr Phe Asn Pro Asn Pro Glu Ile Ser Ala Leu Val Val Ser
    1130                1135                1140

Tyr Asn Asp Gly Arg Leu Cys Leu Phe Asp Tyr Thr Thr Met Met
    1145                1150                1155

Pro Thr Phe Thr Arg Gln Ser Val Phe Ala Asn Ser Ile Ala Cys
    1160                1165                1170

Ser Pro Asp Gly Arg Ser Leu Val Thr Gly Ser Val Arg Gly Ile
    1175                1180                1185

Ile Glu Val Phe Lys Phe Asp Gln Asp His Thr Gly Asn Thr Val
    1190                1195                1200

Leu Val Pro Ile Tyr Asn Ile Gln Ala Leu Asp Asp Ser Ile Arg
    1205                1210                1215

Ser Val Ala Phe Ser Ala Asp Gly Leu Arg Phe Val Asp Leu His
    1220                1225                1230

Asp Gln Gln Cys Arg Ile Trp Ala Pro Val Ser Leu Met Arg Lys
    1235                1240                1245

Asp Asn Glu Leu Glu Ser Val Ser Gly Ile Ala Pro Leu Pro Ala
    1250                1255                1260

Lys Ile Val Thr Met Ala Asp Asp Ser Asn Ile Thr Glu Ile Thr
    1265                1270                1275

Ser Ala Leu Ala Val Ser Ser Asn Gly Gly Arg Val Ile Ala Gly
    1280                1285                1290

Lys Ser Asn Gly Glu Val Ser Ala Phe Ser Ala Val Asp Gly Lys
    1295                1300                1305

Glu Leu Gly Val Leu Tyr Ser His Gly Arg Cys Val Ser Val Val
    1310                1315                1320

Asn Val Thr Leu Gly Glu Ala Arg Asn Leu Val Ile Ser Ala Asp
    1325                1330                1335

Asp Ala Gly Arg Val Leu Val Val Glu Leu Thr Thr Cys Leu Pro
```

```
        1340                1345                1350
Ala Ser Ser Ala Ala Gln Lys Leu Pro Ala Ala His Val Ile Leu
    1355                1360                1365
Glu Arg Arg Phe Gly Ala Ala Val Val Gly Leu Leu Val Asn Pro
    1370                1375                1380
Ser Val Asp Arg Leu Leu Ile Ser Gly Arg His Val Asp Glu Leu
    1385                1390                1395
Cys Asp Leu Pro Ser Gly Arg Val Leu Gly Ser Ile Ser His Val
    1400                1405                1410
Val Gly Thr Ala Thr Ser Thr Arg Ala Val Ala Phe Gln His Pro
    1415                1420                1425
Ala Asn Glu Ala Trp Ile Val Leu Met Leu Thr Asn Thr Ala Arg
    1430                1435                1440
Val Phe Arg Trp Ser Asp Phe Gln Glu Leu Thr Thr Val Asn Gly
    1445                1450                1455
Ile Leu Leu Arg Lys Pro Ser Thr Ala Val Glu Ala Pro Leu Pro
    1460                1465                1470
Thr His Ser Arg Ala Leu Lys Thr Pro Thr Thr Leu Ser Ser Ser
    1475                1480                1485
Tyr His Phe Arg Gln Asp Phe Val Leu Glu Leu Leu Arg Ile Ser
    1490                1495                1500
Pro Ser Val Ala Pro Arg Leu Tyr Val Trp Pro Val Ser Ala Phe
    1505                1510                1515
Asp Pro Ala Thr Ala Gln Pro Asp His Arg Ala Gln Val Pro Arg
    1520                1525                1530
Glu Val Asn Leu Asp Ala Ile Asn Ala Gly Ile Leu Ala Val Leu
    1535                1540                1545
Gly Ile Val Gly Gln Ser Thr Val Leu Leu Met Asp Ala Asn Leu
    1550                1555                1560
Trp Val Tyr Ser Met Glu Leu Arg Pro Thr Gln Ala Thr Pro Gln
    1565                1570                1575
Ala His Pro Gly Phe Pro Pro Glu Thr Thr Ile Val Gln Asp Gly
    1580                1585                1590
Pro Glu Pro Ile Thr Gln Gln Ile Leu Pro Val Phe Thr Arg Arg
    1595                1600                1605
His Phe Phe Ala Leu Ser Glu Trp Arg Thr Ala Gly Glu Glu Leu
    1610                1615                1620
Arg Cys Ala Val Ala Gln His Ser Gly Gly Pro Ser Phe Ile Phe
    1625                1630                1635
Ala Ser Arg Gln Tyr Ile Val Val Val Gln Gly Gly Leu Glu Phe
    1640                1645                1650
Ser Glu Asp Met Ala Val Gly Gln Gln Ser Ala
    1655                1660
```